(12) United States Patent
Reichardt et al.

(10) Patent No.: US 10,001,488 B2
(45) Date of Patent: Jun. 19, 2018

(54) SYNTHESIS AND USE OF ISOTOPICALLY-LABELLED GLYCANS

(71) Applicant: Asociación Centro de Investigación Cooperativa en Biomateriales, Gipuzkoa (ES)

(72) Inventors: Niels-Christian Reichardt, Gipuzkoa (ES); Begoña-Maria Echeverría Beistegui, Gipuzkoa (ES); Juan Etxebarria, Gipuzkoa (ES); Javier Calvo, Gipuzkoa (ES); Nerea Ruiz, Gipuzkoa (ES)

(73) Assignee: Asocación Centro de Investigación Cooperativa en Biomaterials, San Sebastian, Gipuzkoa (ES)

( * ) Notice: Subject to any disclaimer, the term of this patent is extended or adjusted under 35 U.S.C. 154(b) by 5 days.

(21) Appl. No.: 14/781,692

(22) PCT Filed: Apr. 3, 2014

(86) PCT No.: PCT/EP2014/056737
§ 371 (c)(1),
(2) Date: Oct. 1, 2015

(87) PCT Pub. No.: WO2014/161960
PCT Pub. Date: Oct. 9, 2014

(65) Prior Publication Data
US 2016/0025742 A1    Jan. 28, 2016

(30) Foreign Application Priority Data

Apr. 3, 2013 (GB) .................................. 1305986.0

(51) Int. Cl.
| | | |
|---|---|---|
| *C07H 15/203* | (2006.01) | |
| *C07H 5/04* | (2006.01) | |
| *G01N 33/68* | (2006.01) | |
| *C07H 13/00* | (2006.01) | |
| *G01N 33/50* | (2006.01) | |
| *C08B 37/00* | (2006.01) | |
| *C12P 19/04* | (2006.01) | |
| *C12P 19/18* | (2006.01) | |
| *H01J 49/00* | (2006.01) | |

(52) U.S. Cl.
CPC .......... *G01N 33/6848* (2013.01); *C07H 5/04* (2013.01); *C07H 13/00* (2013.01); *C07H 15/203* (2013.01); *C08B 37/0063* (2013.01); *C12P 19/04* (2013.01); *C12P 19/18* (2013.01); *G01N 33/50* (2013.01); *H01J 49/0036* (2013.01); *G01N 2400/00* (2013.01); *G01N 2458/15* (2013.01); *G01N 2458/20* (2013.01)

(58) Field of Classification Search
CPC . G01N 33/6848; G01N 2458/20; C12P 19/18; C12P 19/04; C07H 5/04; C07H 15/203; H01J 49/0036

USPC .......................................................... 514/27
See application file for complete search history.

(56) References Cited

U.S. PATENT DOCUMENTS

2010/0081150 A1* 4/2010 Liu ..................... C07K 16/18
435/7.21

FOREIGN PATENT DOCUMENTS

| EP | 0 244 932 A2 | 11/1987 |
|---|---|---|
| WO | 2008/130924 A2 | 10/2008 |

OTHER PUBLICATIONS

Breidenbach, Mark A. et al., "Mapping Yeast N-Glycosites with Isotopically Recoded Glycans", Molecular & Cellular Proteomics, 11(6): M111.015339. DOI: 10.1074/mcp.M111.015339 (2012).

Yuan, Jin et al., "Isotope tag method for quantitative analysis of carbohydrates by liquid chromatography-mass spectrometry", Journal of Chromatography A, 1067: 145-152 (2005).

Yu, Fei et al., "Structural Monitoring of Oligosaccharides through 13C Enrichment and NMR Observation of Acetyl Groups", Biophysical Journal, 91: 1952-1959 (2006).

Becker, Hubert et al., "Chemoenzymatic synthesis of stable isotope labeled UDP-N-[2H]-acetyl-glucosamine and [2H]-acetyl-chitooligosaccharides", Glycoconj. J., 23: 687-692 (2006).

Bendiak, Brad et al., "An effective strategy for structural elucidation of oligosaccharides through NMR spectroscopy combined with peracetylation using doubly 13C-labeled acetyl groups", Can. J. Chem., 80: 1032-1050 (2002).

Schwarzmann, Gunter et al., "Synthesis of novel NBD-GM1 and NBD-GM2 for the transfer activity of GM2-activator protein by a FRET-based assay system", Glycobiology, 15(12): 1302-1311 (2005).

Chang, Robert et al., "Probing the mechanism of a fungal glycosyltransferase essential for cell wall biosynthesis. UDP—Chitobiose is not a substrate for chitin synthase", Org. Biomol.41 (2003).

Atwood, James A. et al., "Quantitation by Isobaric Labeling: Applications to Glycomics", Journal of Proteome Research, 7: 367-374 (2008).

Blixt, Ola et al., "Chemoenzymatic Synthesis of Glycan Libraries", Methods in Enzymology, 415: 137-153 (2006).

(Continued)

*Primary Examiner* — Shaojia Anna Jiang
*Assistant Examiner* — Michael C Henry
(74) *Attorney, Agent, or Firm* — Kathleen D. Rigaut; Dann, Dorfman, Herrell and Skillman, P.C.

(57) ABSTRACT

Isotopically-labelled glycans and their synthesis and use as internal standards in the analysis by mass spectrometry of glycan mixtures is described. The methods of synthesis described herein may be used conveniently to prepare libraries of heavy glycans for use in the qualitative and quantitative identification of glycans in natural samples.

18 Claims, 9 Drawing Sheets

(56) References Cited

OTHER PUBLICATIONS

Botelho, Julianne Cook et al., "Quantification by isobaric labeling (QUIBL) for the comparative glycomic study of O-linked glycans", International Journal of Mass Spectrometry, 278: 137-142 (2008).

Bowman, Michael J. et al., "Tags for the Stable Isotopic Labeling of Carbohydrates and Quantitative Analysis by Mass Spectrometry", Anal. Chem., 79: 5777-5784 (2007).

Bowman, Michael J. et al., "Comparative Glycomics Using a Tetraplex Stable-Isotope Coded Tag", Anal. Chem., 82 (7): 3023-3031 (2010).

Hitchcock, Alicia M. et al., "Glycoform Quantification of Chondroitin/Dermatan Sulfate Using a Liquid Chromatography—Tandem Mass Spectrometry Platform", Biochemistry, 45: 2350-2361 (2006).

Hsu, Joanne et al., "MALDI-TOF and ESI-MS Analysis of Oligosaccharides Labeled with a New Multifunctional Oligosaccharide Tag", J. Am. Soc. Mass Spectrom., 17: 194-204 (2006).

Kang, Pilsoo et al., "Comparative Glycomic Mapping through Quantitative Permethylation and Stable-Isotope Labeling", Anal. Chem., 79: 6064-6073 (2007).

Lawrence, Roger et al., "Evolutionary Differences in Glycosaminoglycan Fine Structure Detected by Quantitative Glycan Reductive Isotoipe Labeling", Journal of Biological Chemistry, 283(48): 33674-33684 (2008).

Ridlova, Gabriela et al., "Oligosaccharide relative quantitation using isotope tagging and normal-phase liquid chromatography/mass spectrometry", Rapid Commun. Mass Spectrom., 22: 2723-2730 (2008).

Rising, Thomas W.D.F. et al., "Endohexosaminidase-Catalysed Glycosylation with Oxazoline Donors: Fine Tuning of Catalytic Efficiency and Reversibility", Chem. Eur. J., 14: 6444-6464 (2008).

Ruiz, Nerea et al., "Experimental observations on the regioselectivity of glycosylation of a 4,6-diol system in the beta-D-mannopyranosyl unit of a N-glycan pentasaccharide core structure", Carbohydrate Research, 346: 1581-1591 (2011).

Serna, Sonia et al., "Construction of N-Glycan Microarrays by Using Modular Synthesis and On-Chip Nanoscale Enzymatic Glycosylation", Chem. Eur. J., 16: 13163-13175 (2010).

Xia, Baoyun et al., "Glycan reductive isotope labeling for quantitative glycomics", Analytical Biochemistry, 387: 162-170 (2009).

Zhang, Hui et al., "Identification and quantification of N-linked glycoproteins using hydrazide chemistry, stable isotope labeling and mass spectrometry", Nature Biotechnology, 21(6): 660-666 (2003).

Zou, Guozhang et al., "Chemoenzymatic Synthesis and Fcγ Receptor Binding of Homogeneous Glycoforms of Antibody Fc Domain", J. Am. Chem. Soc., 133: 18975-18991 (2011).

International Search Report/Written Opinion, dated May 20, 2014, issued in corresponding International Application No. PCT/EP2014/056737, filed Apr. 3, 2014.

Search Report, dated Oct. 16, 2013, issued in corresponding GB Application No. 1305986.0, filed Apr. 3, 2013.

* cited by examiner $^{13}C_8$-G0(Bn$_5$)

$^{13}C_4$-Man3(Bn$_5$)

$^{13}C_6$-MGn 3(Bn$_5$)

$^{13}C_6$-MGn 6(Bn$_5$)

SYNTHESIS AND USE OF ISOTOPICALLY-LABELLED GLYCANS

CROSS-REFERENCE TO RELATED APPLICATIONS

This application is a 371 of International Application No. PCT/EP2014/056737, filed Apr. 3, 2014, which claims priority from Great Britain Patent Application No. 1305986.0, filed Apr. 3, 2013. The entire disclosure of each of the aforesaid applications is incorporated by reference in the present application.

FIELD OF THE INVENTION

The present invention relates to isotopologues of oligosaccharides and polysaccharides. In particular, the present invention relates to the synthesis of isotopically-labelled glycans and their use as standards in the analysis by mass spectrometry of glycan mixtures.

BACKGROUND OF THE INVENTION

Glycosylation is one of the most common post-translational protein modifications in eukaryotic systems. It has been estimated that over half of all mammalian proteins are glycosylated at some point during their existence and virtually all membrane and secreted proteins are glycosylated. Glycosylation is a non-template-driven process and is believed to introduce the high level of variability necessary for complex processes in higher organisms. In addition to participating in key macromolecular interactions, glycans have been shown to contribute to protein folding, trafficking, and stability.

N-glycans are linked to the protein backbone via asparagine residues that are part of the tripeptide sequences Asn-X-Ser or Asn-X-Thr, with X being any amino acid except proline. Depending on the terminal sugar residues, N-glycans are classified into complex, high-mannose, and hybrid N-glycans. This classification is based on the common pentasaccharide motif shared by most N-glycans. O-glycans are linked via serine or threonine residues to the protein. There are a number of O-glycan core structures, with the most common being Core 1, Core 2, Core 3, and Core 4.

Numerous diseases are known to involve acquired changes in glycosylation and/or in the recognition of glycans. For example, altered glycosylation is a universal feature of cancer cells and some glycan structures are well-known markers for tumours and tumour progression. As a result, methods for the comprehensive analysis of protein glycosylation and glycan composition are of interest to the scientific community.

For most glycol-profiling methods, the glycans are removed from the protein either by hydrazinolysis or treatment with a specific peptide glycosidase (e.g. PNGase F). Owing to its high sensitivity at low concentrations, mass spectrometry is often used in the analysis of the resulting complex mixtures. However, the signal intensity of particular analytes is dependent, amongst many other factors, on the physical properties (likelihood of ionisation, tendency to fragment, etc.) of the analyte, making any relative quantification, and sometimes even identification, very difficult.

Identification of glycans common to two samples and their relative quantification may be facilitated by use of derivatisation of the glycan mixtures to incorporate isotopic tags. The two samples are labelled with the light and heavy form of the labelling reagent and then mixed prior to analysis using mass spectrometry. Derivatisation to incorporate isotopic tags into glycan mixtures isolated from glycoproteins has been accomplished using permethylation techniques or glycan reductive isotope labelling, in which the tag is introduced using reductive amination (Atwood, 2007; Bowman, 2007, 2010; Botelho, 2008; Hitchcock, 2006; Hsu, 2006; Kang, 2007; Lawrence, 2008; Ridlova, 2008; Yuan, 2005; Zhang, 2003).

Reductive amination typically occurs at the reducing end of the glycans and may use isotopically-labelled aniline, aminopyridine or anthranilic acid. For example, Xia et al. (2009) have demonstrated the use of isotopically-labelled aniline tags to compare the differences in mixtures of glycans released from human and mouse sera. The glycans were released by PNGase F, then the resulting mixtures separately derivatised by reductive amination with $^{12}C_6$-aniline or $^{13}C_6$-aniline. By analysing an equimolar combination of the $^{12}C_6$-aniline-derivatised mixture of glycans from mouse serum and the $^{13}C_6$-aniline-derivatised mixture of glycans from human serum, the authors reported that they were able to identify paired mass peaks separated by a mass difference of 6 Da and assign plausible structures for glycans common to both samples. The authors reported that a comparison of the relative intensities of these peaks enabled a determination of the amount of a particular common glycan present in one sample compared to the other.

However, these methods provide only semi-quantitative results. Furthermore, the results are affected by the reproducibility of the tagging procedures and problems caused by side reactions, oxidative degradation and "peeling reactions" (which may occur due to certain reaction conditions in aqueous solutions), and important functionalization may be lost during the derivatisation step.

Isotopic tags have also been used in proteomics. Breidenbach et al. (2012) have demonstrated the metabolic incorporation of isotopically-labelled GlcNAc into yeast N-glycans using filter aided sample preparation methodology. A GlcNAc isomix was used comprising natural isotope abundance GlcNAc, $^{13}C_2$-GlcNAc and $^{13}C_4{}^{15}N_1$-GlcNAc in a 1:2:1 ratio to mimic the dibromide isotope triplet pattern. The resulting glycol conjugates containing the isomix underwent FASP digestion and EndoH deglycosylation and were analysed using an automated isotopic envelope pattern search (in LC-MS/MS experiments) to facilitate glycoside identification. The method enabled the authors to place fragmentation priority on glycopeptides ions regardless of their relative intensities to other ions in the sample.

There exists an unmet need for improved methods for rapidly and easily analysing the content of released glycan mixtures, and in particular one which does not suffer from the disadvantages of the described prior art.

SUMMARY OF THE INVENTION

The present invention is based on the inventors' insight that stable isotopologues of individual glycans and glycoconjugates used as standards in mass spectrometry may have utility in the qualitative and quantitative analysis of complex mixtures. In particular, the present invention addresses the problems of reproducibility and loss of functional information associated with the isotopic glycan-tagging procedures known in the art, in which glycan mixtures are derivatised to incorporate the tag either during or following removal from the protein. The present inventors have provided methods for the synthetic generation of isotopically-labelled glycans then may then be doped into an analyte sample and analysed by mass spectrometry. These methods allow for the identification of glycans of known structure in analyte sample through comparison of the mass spectrometry envelope(s) associated with the remaining mass spectrometry peaks (associated with the sample).

Furthermore, the present invention allows quantification of particular glycans within the sample in absolute terms through addition of a known amount of the standard, representing a significant advantage over the methods known in the art which provide only semi-quantitative data. The present invention provides libraries of isotopically-labelled glycan standards (so-called "tagged standards") for use in the qualitative and quantitative analysis of complex glycan mixtures using mass spectrometry. Further provided are methods for using these standards to analyse qualitatively and/or quantitatively the composition of complex glycan mixtures. These methods of analysis may have utility in the identification of glycan markers associated with particular disorders and disease states and other biological processes.

Broadly, the present invention includes methods for the synthesis of isotopically-labelled glycans (including glycoconjugates) comprising treating a glycan comprising at least two sugar units with an isotopically-labelled acylating agent to incorporate isotopic labels into glycan structures.

These isotopically-labelled oligosaccharides are oligosaccharide core structures which may then be used to synthesise libraries of isotopically-labelled glycan standards through enzymatic derivatisation steps, that is, diversification by one or more enzyme-catalysed steps. This represents a significant advance in methods for the qualitative (and quantitative) detection of particular glycans.

Accordingly, in a first aspect, the present invention relates to a method for the synthesis of an isotopically-labelled oligosaccharide, the method comprising:
  acylating an oligosaccharide with an isotopically-labelled acylating agent, wherein the oligosaccharide is optionally protected with one or more protecting groups.

In a first aspect, the present invention provides a method for the synthesis of an isotopically-labelled glycan for use as a mass spectrometry internal standard, the method comprising:
  acylating an oligosaccharide core structure with an isotopically-labelled acylating agent, wherein the oligosaccharide core structure is optionally protected with one or more protecting groups, to obtain an isotopically-labelled oligosaccharide core structure; and
  enzymatically derivatising the resultant isotopically-labelled oligosaccharide to obtain the isotopically-labelled glycan.

Enzymatic derivatisation, which may also be referred to as enzymatic diversification, as used herein, refers to subjecting an oligosaccharide as described herein to an enzyme-catalysed reaction. Suitable enzymatic derivitisation/diversification reactions include:
  Elongation: the addition of (a) further sugar unit(s) to the oligosaccharide, typically via a condensation reaction with a suitable sugar donor using a glycosyltransferase. Elongation may occur at a terminus of the oligosaccharide, or on an intermediate sugar unit.
  Truncation: the removal of (a) sugar unit(s) from a terminus of the oligosaccharide. This is typically via a hydrolysis reaction with a hydrolase.
  Epimerisation: the total or partial inversion of a stereocentre in the molecule. This is typically catalysed by an epimerase.
  Transglycosylation (glycosyl transfer reactions): the transfer of a sugar unit from a donor to an acceptor; that is, one oligosaccharide loses a sugar unit, i.e. is truncated, while another oligosaccharide gains a sugar unit (i.e. is elongated). These reactions may be catalysed by a synthetase or transglycosidase.
  Post-translation modification: other functionalization may be incorporated during enzymatic derivatisation. Common post-translational modifications are known in the art, and may include, without limitation, phosphorylation, sulfation and acylation.

Typically, such enzyme-catalysed derivatisation steps are chemo-selective. It will be appreciated that the first aspect of the present invention provides methods for the convenient generation of vast numbers of isotopically-labelled glycan structures for use as mass spectrometry internal standards starting from relatively small "core" oligosaccharides, as described herein.

In some embodiments, the enzymatic derivatisation step comprises a step of enzymatic hydrolysis to remove a terminal sugar unit. This allows access to asymmetric standards derived from, for example, the biantennary heptasaccharide N-glycan core, synthesised as described herein.

In some embodiments, the enzymatic derivatisation step comprises a step of enzymatic elongation of the resultant glycan with a glycosyltransferase and a suitable sugar donor. Suitable methods of enzymatic elongation are known in the art (Blixt, 2006; Ruiz, 2001; Serna, 2010, Zou, 2011) and are further described below. Suitable sugar donors may be mono-, oligo- or poly-saccharides. In some embodiments, the step of enzymatic elongation is repeated one or more times. In embodiments in which the step of enzymatic elongation is repeated, preferably the sugar donor in each step is a suitable monosaccharide sugar donor.

In some embodiments, the sugar donor in the enzymatic elongation step is isotopically-labelled. In embodiments in which the step of enzymatic elongation is repeated, the sugar donor in an enzymatic elongation step may be isotopically-labelled independent of whether or not the sugar donor in any other enzymatic elongation step is or is not isotopically-labelled. The sugar donor may be isotopically-labelled with any suitable isotopic form of an atom at any suitable position. In this way, additional isotopically-labelled monosaccharide units may be incorporated into the isotopically-labelled oligosaccharide. This may have utility in the analysis of glycans using fragmentation patterns obtained in MS-MS methods and for generating different isotopologues of a particular glycan structure to aid accurate quantitative analysis as described below.

It will be appreciated that the enzymatic derivatisation step may comprise a single enzyme-catalysed step, or may include more than one enzyme-catalysed step in sequence. For example, the enzymatic derivatisation step may be a single hydrolysis or elongation step, or may include more than more one hydrolysis and/or elongation step to generate the desired glycan structures. For example, an isotopically-labelled oligosaccharide core may be sequentially elongated, or truncated and then (sequentially) elongated. An isotopically-labelled oligosaccharide may also be elongated and then truncated at a different position. Different ordering of the steps may be desirable to suit the specificity of the enzymes used. Representative non-limiting examples are provided herein.

As used herein, the term oligosaccharide pertains to saccharide polymers comprising at least two simple sugars (monosaccharide units). In some embodiments, the oligosaccharide is a disaccharide. In some embodiments, the oligosaccharide is a trisaccharide. In some embodiments, the oligosaccharide is a tetrasaccharide. In some embodiments, the oligosaccharide is a pentasaccharide. In some embodiments, the oligosaccharide is a hexasaccharide. In some embodiments, the oligosaccharide is a heptasaccharide. In some embodiments, the oligosaccharide is a higher oligomer. The oligosaccharide may be linear or branched (also referred to as antennary).

The oligosaccharide may comprise one or more hydroxyl or amino groups, each of which may independently be protected with a protecting group. In some embodiments, free hydroxyl and/or amino groups are not protected. In other embodiments, some or all of the hydroxyl groups present are protected. In some embodiments, at least one protected primary and/or secondary amino group is present.

Suitable protecting groups for hydroxyl and amino groups are known in the art. Purely by way of example, and without limitation, suitable protecting groups for use in the present invention are discussed below. In some embodiments, protecting groups are selected to be orthogonal to each other to facilitate selective deprotection and chemical manipulation at desired positions on the oligosaccharide.

Preferably, the oligosaccharide comprises at least one free —NH$_2$ group and acylation occurs at the free —NH$_2$ group. Where more than one free —NH$_2$ group is present, acylation may occur at each free —NH$_2$ group.

The present inventors have found that semi-protected core motifs are suitable substrates for chemoselective enzymatic derivatisation. Furthermore, the presence of the protecting groups may have particular advantages. For example, as described herein, benzylic groups may act as chromophores for peak detection during HPLC analysis and purification, and may aid separation of different products, for example, isomeric glycans.

Accordingly, in some methods described herein, the isotopically-labelled core oligosaccharides are partially protected during the enzymatic derivatisation step. Suitably, the protecting groups are optionally substituted benzyl groups, preferably —CH$_2$Ph groups, present on one or more hydroxyl groups.

For example, the methods described herein may include at least one enzymatic derivatisation step on an isotopically-labelled partially protected oligosaccharide, followed by a deprotection step. Further enzymatic derivatisation step(s) may then follow. For example, the partially protected oligosaccharide may be partially benzylated. Suitably, when the oligosaccharide has one or more benzyl groups, the deprotection step may be hydrogenation.

In some embodiments, the oligosaccharide comprises a disaccharide motif, the disaccharide motif comprising a first monosaccharide unit and a second monosaccharide unit, wherein at least one of the first monosaccharide unit and/or second monosaccharide unit comprises an amino group and acylation occurs at the amino group(s). In embodiments in which the oligosaccharide comprises more than two monosaccharide units, the disaccharide motif may be located at a terminus of the saccharide chain, which may be a reducing or non-reducing end. In embodiments in which the oligosaccharide comprises more than four monosaccharide units, the disaccharide motif may be located at a terminus or an intermediate position within the saccharide chain.

The monosaccharide comprising an amino group is preferably an amino sugar monosaccharide. Broadly, any amino sugar monosaccharide having at least one —NH$_2$ group may be suitable as at least one of the first monosaccharide unit and/or second monosaccharide unit in methods of the first aspect of the present invention. Examples of suitable amino sugars include, but are not limited to, hexosamines and derivatives thereof. Examples of suitable amino sugar monosaccharidees include, but are not limited to, glucosamine (GlcN), galactosamine (GalN), mannosamine (ManN), fructosamine (FruN), fucosamine (FucN), muramic acid (Mur), neuraminic acid (Neu), daunosamine, and perosamine.

Other amino sugars derivatives may also be suitable for use according to the present invention. Accordingly, in some embodiments, the first monosaccharide unit and/or second monosaccharide unit is a des-acetyl derivative of an N-acetyl amino sugar. Suitable examples, in addition to those listed above, include, for example, des-acetyl aspartyl-glucosamine. Monosaccharide units may also be further substituted and comprise a part of, for example, a glycoside.

The second monosaccharide unit may be a second amino sugar, an acetyl amino sugar, or other sugar unit. For example, and not by way of limitation, the second monosaccharide unit may be a hexose or pentose or amino sugar thereof, and may be further substituted with, for example, fatty acid chains (for example, the second monosaccharide unit may be lipid A).

In some embodiments in which the oligosaccharide comprises a disaccharide motif, the first monosaccharide unit is selected from:
GlcN, GalN, ManN, FruN, FucN, Mur, or Neu;
and the second monosaccharide unit is selected from:
Glc, Gal, Man, Rha, Fru, Fuc, GlcN, GalN, ManN, FruN, FucN, Mur, Neu, GlcNAc, GalNAc, ManNAc, FruNAc, FucNAc, MurNAc, NeuNAc, sialic acid, or inositol.

The first monosaccharide sugar and the second monosaccharide sugar unit may be arranged in the sequences, from reducing end to non-reducing end, first monosaccharide unit followed by second monosaccharide unit, or second monosaccharide unit followed by first monosaccharide unit.

In one embodiment, the sequence is:
first monosaccharide-second monosaccharide.
In one embodiment, the sequence is:
second monosaccharide-first monosaccharide.

In some preferred embodiments, the first and second monosaccharide units of the disaccharide motif of the oligosaccharide are selected from the monosaccharide units associated with N- and O-glycan cores and des-acetyl forms thereof. Accordingly, in some embodiments, the first monosaccharide unit is glucosamine or galactosamine and the second monosaccharide unit is selected from mannose, galactose, glucosamine, galactosamine, N-acetyl-glucosamine, or N-acetyl-galactosamine. In some embodiments, the first monosaccharide unit is glucosamine and the second monosaccharide unit is selected from mannose, galactose, glucosamine, galactosamine, N-acetyl-glucosamine, or N-acetyl-galactosamine, preferably from mannose or glucosamine. In some embodiments, the first monosaccharide unit is galactosamine and the second monosaccharide unit is selected from mannose, galactose, glucosamine, galactosamine, N-acetyl-glucosamine, or N-acetyl-galactosamine, preferably from mannose or glucosamine.

In some embodiments, the method comprises reacting an oligosaccharide comprising a motif selected from:
GlcN-GlcN
Gal-GalN
GalN-GlcN
with an isotopically-labelled acylating agent. Further monosaccharide units may be present at the reducing and/or non-reducing ends.

In some embodiments, the method comprises reacting an oligosaccharide comprising the motif:
Man-GlcN-GlcN
with an isotopically-labelled acylating agent. Further monosaccharide units may be present at the reducing and/or non-reducing ends.

In a preferred embodiment, the method comprises reacting an oligosaccharide comprising the motif:

Man-GlcN-GlcN with an isotopically-labelled acetylating agent to obtain an oligosaccharide comprising the motif:

Man-GlcNAc*-GlcNAc* wherein Ac* is an isotopically-labelled acetyl group.

In some embodiments, the method comprises reacting an oligosaccharide of formula (A) with an isotopically-labelled acetylating agent under conditions suitable to form an oligosaccharide of formula (B):

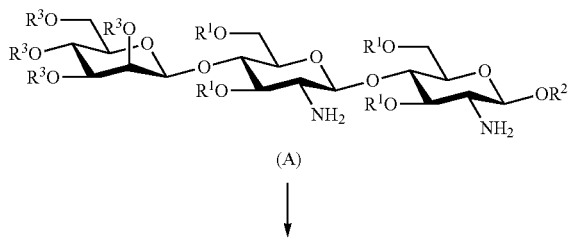

(A)

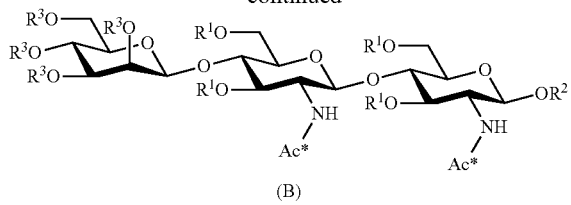

(B)

wherein:

each $R^1$ is independently H or a protecting group;

$R^2$ is independently H or a protecting group;

each $R^3$ independently is H, a protecting group, or (Sac), wherein each

Sac is a monosaccharide unit and m is a number between 1 and 50.

In some embodiments, the method comprises reacting an oligosaccharide of formula (C) with an isotopically-labelled acetylating agent under conditions suitable to form an oligosaccharide of formula (D):

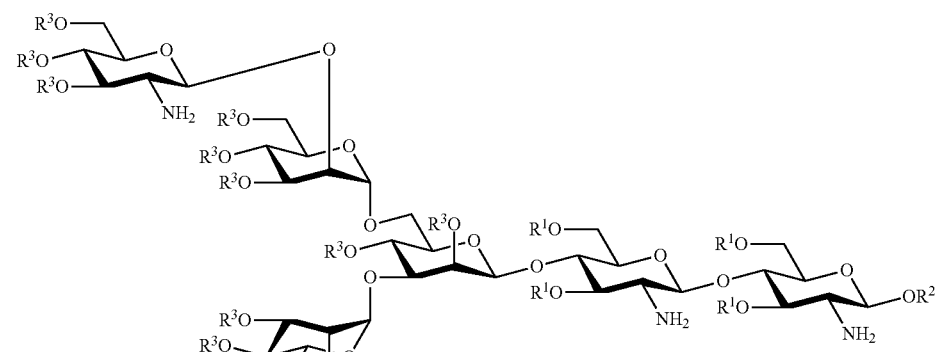

(C)

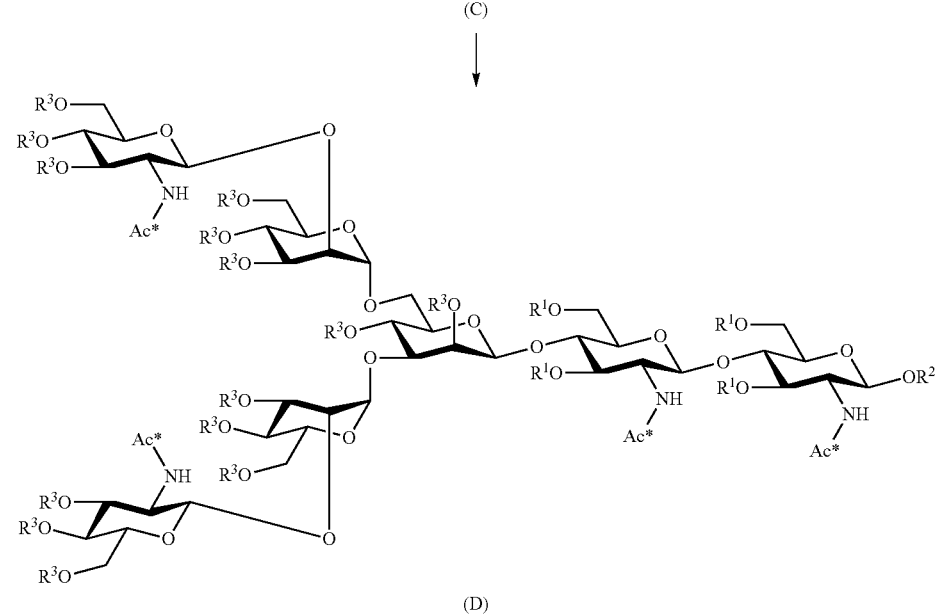

(D)

wherein:
each $R^1$ is independently H or a protecting group;
$R^2$ is independently H or a protecting group;
each $R^3$ is independently H, a protecting group, or $(Sac)_m$ wherein each Sac is a monosaccharide unit and m is a number between 1 and 50.

As defined above, in some embodiments, each $R^1$, $R^2$ and $R^3$ may independently be a protecting group. The protecting groups may be the same or different. For example, if more than one $R^3$ is a protecting group, each $R^3$ may be the same as, or different to, any other protecting group. In some embodiments, at least one $R^3$ is $(Sac)_m$, wherein m is a number between 1 and 50. In embodiments in which more than one $R^3$ is $(Sac)_m$, each $(Sac)_m$ may independently be the same or different to any other $(Sac)_m$ in the molecule.

In some embodiments, m is a number between 1 and 20.
In some embodiments, m is a number between 1 and 10.
In some embodiments, m is a number between 1 and 5.
In some embodiments, m is 1 or 2.
In some embodiments, $R^2$ is H. In some embodiments, each $R^3$ is H. In a preferred embodiment, each $R^1$ is benzyl, $R^2$ is H, and each $R^3$ is H.

In some embodiments, the method comprises:
glycosylating an oligosaccharide of formula (I):

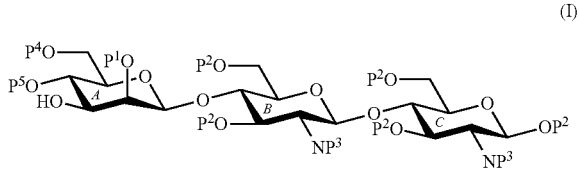

(I)

wherein each of $P^1$, $P^2$, $P^3$, $P^4$, and $P^5$ is independently a protecting group, or optionally $P^4$ and $P^5$ together form an acetal group;
with a sugar donor of general formula (II):

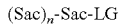   (II)

wherein each Sac is a monosaccharide unit, n is a number between 0 and 50, and -LG represents the non-glycosylated anomeric position of the donor-sugar primed with a suitable leaving group;
to give an oligosaccharide of formula (III):

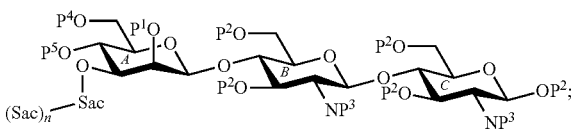

(III)

removing $P^4$ to reveal a hydroxyl group and glycosylating the resulting hydroxyl group with a sugar donor of general formula (II);
removing each $P^3$ group to reveal a free amino group and acetylating each resultant free amino group with an isotopically-labelled acetylating agent.

In some embodiments, n is a number between 0 and 20.
In some embodiments, n is a number between 0 and 10.
In some embodiments, n is a number between 0 and 5.
In some embodiments, n is 0 or 1.

Suitable sugar donors are known in the art and may include, without limitation, glycosyl halides, for example, glycosyl fluorides and bromides; glycosyl phosphates, glycosyl trihaloacetimidates, n-pentenyl glycosides (and more generally, suitable hemiacetals, orthoesters and 1-oxygen substituted glycosyl donors) and thio-glycosides. The reactivity of a sugar donor may depend upon the nature of any protecting groups present. Sugar donors may be disarmed (for example, by protection with acetyl groups), armed (for example, by protection with benzyl groups) or super-armed (for example, by protection with bulky silyl groups).

In some preferred embodiments, the sugar donor leaving group comprises a trihaloacetimidate group, preferably a trifluoroacetimidate group, such as, for example:

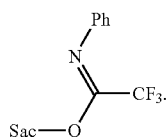

In some embodiments, the method comprises the step of glycosylating the $C_2$-position of monosaccharide unit A to obtain a bi-antennary glycan. In some embodiments, the method comprises the step of glycosylating the C4-position of monosaccharide unit A. Glycosylation at the C4-position may follow glycosylation at the C2-position to yield a tri-antennary glycan, or may occur without a prior C2-glycosylation step to yield a bi-antennary glycan. In embodiments in which the method comprises glycosylation at both C2 and C4 of monosaccharide unit A, the glycosylation steps may occur in either order.

Chemo-selective glycosylation may be enzymatically-catalysed and/or may be facilitated by selective protection and/or protecting group strategies.

Preferably, the oligosaccharide core used for the enzymatic derivatisation is comprises 3 to 9 monosaccharide units.

In some embodiments of the methods of the present invention, the isotopically-labelled acylating agent may be an acyl halide or an anhydride of a suitable carboxylic acid. In some preferred embodiments, the isotopically-labelled acylating agent is isotopically-labelled acetic anhydride, preferably $(^{13}CH_3^{13}C=O)_2$, $(^{13}CH_3C=O)_2$, $(CH_3^{13}C=O)_2$, $(CD_3C=O)_2$, $(^{13}CD_3^{13}C=O)_2$, $(^{13}CD_3C=O)_2$, or $(CD_3^{13}C=O)_2$. In some embodiments, the isotopically-labelled acylating agent is $(^{13}CH_3^{13}C=O)_2$.

In some embodiments of the present invention, each Ac*, if present, is selected from $-(^{13}C=O)^{13}CH_3$, $-(C=O)^{13}CH_3$, $-(^{13}C=O)CH_3$, $-(C=O)CD_3$, $-(^{13}C=O)^{13}CD_3$, $-(C=O)^{13}CD_3$, $-(^{13}C=O)CD_3$, $-(^{14}C=O)^{14}CH_3$, $-(C=O)^{14}CH_3$, $-(^{14}C=O)CH_3$, $-(C=^{17}O)$ $CH_3$, $-(^{13}C=^{17}O)$ $CH_3$, $-(C=^{17}O)^{13}CH_3$, $-(^{13}C=^{17}O)$ $^{13}CH_3$, $-(C=^{18}O)CH_3$, $-(^{13}C=^{18}O)$ $CH_3$, $-(C=^{18}O)$ $^{13}CH_3$, $-(^{13}C=^{18}O)^{13}CH_3$.

In some embodiments of the present invention, each Ac*, if present, is selected from $-(^{13}C=O)^{13}CH_3$, $-(C=O)$ $^{13}CH_3$, $-(^{13}C=O)CH_3$, $-(C=O)CD_3$, $-(^{13}C=O)^{13}CD_3$, $-(C=O)^{13}CD_3$, $-(^{13}C=O)CD_3$, $-(^{14}C=O)^{14}CH_3$, $-(C=O)^{14}CH_3$, $-(^{14}C=O)CH_3$, $-(C=^{17}O)$ $CH_3$, or $-(C=^{18}O)CH_3$.

In some embodiments of the present invention, each Ac*, if present, is selected from $-(^{13}C=O)^{13}CH_3$, $-(C=O)$ $^{13}CH_3$, $-(^{13}C=O)CH_3$, $-(C=O)CD_3$, $-(^{13}C=O)^{13}CD_3$, $-(C=O)^{13}CD_3$ or $-(^{13}C=O)CD_3$. In some embodiments the present invention, each Ac*, if present, is selected from —($^{13}$C═O)$^{13}$CH$_3$, —(C═O)$^{13}$CH$_3$, or —($^{13}$C═O)CH$_3$. In some embodiments of the methods, each Ac*, if present, is —($^{13}$C═O)$^{13}$CH$_3$.

In some embodiments, methods according to the first aspect further comprise forming an oxazoline at a free anomeric position of an acetyl-hexosamine unit in the isotopically-labelled oligosaccharide. The resultant isotopically-labelled glycan oxazoline may then be used to prepare an isotopically-labelled glycoconjugate.

In some embodiments, methods according to the first aspect further comprise glycosylating a peptide, lipid or protein to obtain an isotopically-labelled glycopeptide, peptidoglycan, glycolipid, glycoprotein comprising the isotopically-labelled oligosaccharide.

In a further aspect, the present invention provides an isotopically-labelled oligosaccharide or glycoconjugate obtainable by a method according to the first aspect.

In a further aspect, the present invention provides a glycan comprising a motif selected from:

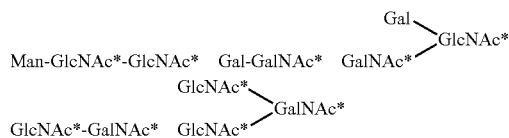

wherein each Ac* is isotopically-labelled. The term glycan, as used herein, refers to any saccharide in free form or forming a carbohydrate portion of a glycoconjugate.

In some embodiments, the motif is:

wherein each Ac* is isotopically-labelled.

In some embodiments, the glycan comprises the motif:

wherein each Ac* is isotopically-labelled.

In some embodiments, each Ac* if present, is selected from —($^{13}$C═O)$^{13}$CH$_3$, —(C═O)$^{13}$CH$_3$, —($^{13}$C═O)CH$_3$, —(C═O)CD$_3$, —($^{13}$C═O)$^{13}$CD$_3$, —(C═O)$^{13}$CD$_3$, —($^{13}$C═O)CD$_3$, —($^{14}$C═O)$^{14}$CH$_3$, —(C═O)$^{14}$CH$_3$, —($^{14}$C═O)CH$_3$, —(C═$^{17}$O)CH$_3$, or —(C═$^{18}$O)CH$_3$ In some embodiments, the glycan comprises one or more further monosaccharide units, wherein each further monosaccharide, if present, may be independently isotopically-labelled.

In some embodiments, the number of further monosaccharide units is greater than 10.

In some embodiments, the number of further monosaccharide units is greater than 30.

In some embodiments, the number of further monosaccharide units is greater than 50.

In some embodiments, the number of further monosaccharide units is greater than 100.

In some embodiments, the present invention provides a glycan that has the structure:

This structure is an especially suitable core oligosaccharide substrate for enzymatic derivatisation to afford a variety of isotopically-labelled N-glycans.

Where each Ac* is —($^{13}$C═O)$^{13}$CH$_3$, this structure is referred to herein as $^{13}$C$_8$-G0. As described herein, there may be advantages to using a semi-protected core oligosaccharide as a substrate for enzymatic derivatisation. Accordingly, in some embodiments, the five hydroxyl moieties at the GlcNAc*-GlcNAc* reducing end bear optionally-substituted benzyl groups. When each Ac* is —($^{13}$C═O)$^{13}$CH$_3$ and these five hydroxyl each bear a PhCH$_2$— moiety, the structure is referred to herein as $^{13}$C$_8$-G0(Bn$_5$).

In a further aspect, the present invention provides a method of identifying a glycan in a sample, the method comprising adding a tagged standard comprising an isotopically-labelled glycan to the sample to obtain a doped sample, and analysing the doped sample using mass spectrometry. In preferred embodiments, the isotopically-labelled glycan is an isotopically-labelled glycan according to the present invention and/or obtainable as described herein.

Preferably, the tagged standard comprises an isotopically-labelled glycan that is an isotopologue of a glycan suspected to be present in the sample. In some embodiments, the tagged standard comprises more than one isotopically-labelled glycan. In some embodiments more than one tagged standard may be added to the sample to obtain the doped sample. In some embodiments, more than one isotopically-labelled glycan may be added to facilitate simultaneous identification of multiple glycans in a sample.

An advantage of methods of the present invention over methods known in the prior art is that tagging of the glycan(s) in the sample to incorporate a tag is not necessary, avoiding issues of reproducibility of tagging procedures and side reactions. Furthermore, sources of experimental variability which may be present in methods known in the art are cancelled out as both the isotopically-labelled glycan(s) (in the tagged standard) and the analyte(s) are analysed in the same experiment and treated using the same procedures. Each isotopically-labelled glycan ionises with the same efficiency as the corresponding analyte but is easily identifiable by its fixed mass increment. In some embodiments, the tagged standard has a pre-determined mass spectrometry spectrum, which may aid in the analysis of the doped sample by enabling ion peaks associated with the isotopically-labelled glycan to be easily identified.

In preferred embodiments, a known amount of the isotopically-labelled glycan is added to the sample such that the glycan content of the sample can be quantified by comparison of the relative intensity of the ion peaks associated with the glycan and the isotopically-labelled glycan. Further details regarding the quantification of glycan content are provided below. Accordingly, through the addition of a known amount of the isotopically-labelled glycan, an analyte may be quantified in absolute terms even in a complex biofluid. In some embodiments, known amounts of more than one isotopically-labelled glycan may be added to facilitate simultaneous identification and quantification of multiple glycans in a sample.

In some embodiments, the method comprises:
 (i) selecting a tagged standard comprising one or more isotopically-labelled glycans;
 (ii) adding the tagged standard to the sample to obtain a doped sample;
 (iii) analysing the doped sample using mass spectrometry to obtain ion peaks;

(iv) comparing the identity and intensity of the ion peaks associated with the tagged standard with the additional ion peaks in the spectrum of the doped sample.

In some preferred embodiments, the tagged standard is selected to correspond to the suspected glycan content of the sample. For example, and not by way of limitation, if a sample is suspected to comprise a combination of three glycan species, a tagged standard comprising isotopologues of these three glycans may be selected.

The glycan(s) may be derivatised prior to analysing the doped sample. Derivatisation steps may include, for example, permethylation or derivatisation of sialic acid residues, if present, and may comprise a clean-up step. In some embodiments, the derivatisation comprises glycosidase treatment for removal of sialic acids or other terminal sugar units.

In some preferred embodiments, the mass spectrometry is MALDI-ToF, direct infusion ESI-ToF or LC-MS, and may further comprise fragmentation by tandem mass spectrometry (sometimes called MS-MS), which may facilitate analyte identification and enable isobaric analytes to be distinguished in complex mixtures. Fragmentation may be achieved using, for example, collision induced dissociation (CID), electron capture dissociation (ECD), electron transfer dissociation (ETD), infrared multiphoton dissociation (IRMPD), black body infrared radiative dissociation (BIRD), electron-detachment dissociation (EDD) or surface-induced dissociation (SID), or any other suitable method.

In some embodiments, the sample is a complex biofluid, and the glycan in the sample may, for example, be a glycan released from a recombinant glycoprotein or antibody. The glycan in the sample may a biomarker associated with a medical disease or disorder, or a biological process, and in some preferred embodiments, the method further comprises correlating the presence or amount of one or more of the glycans as an indicator of a medical disease or disorder, or a biological process. Without limitation, the medical disease or disorder may be selected from cancer, a cardiovascular disorder, an inflammatory skin disease, diabetes mellitus, a gastrointestinal disorder, a liver disorder, anaemia, an immunological disease or disorder, autoimmune disease, arthritis, including rheumatoid arthritis, an infectious disease, nephropathy, a neurological disorder, a pulmonary disorder or a congenital disorder of glycosylation.

These methods may be performed in vitro.

Accordingly, in a further aspect, the present invention provides a method for diagnosing a patient suspected of having a disease associated with a glycan, the method comprising:
(i) obtaining a sample suspected of containing the glycan;
(ii) selecting a tagged standard comprising an isotopically-labelled glycan corresponding to the glycan associated with the disease;
(iii) adding the tagged standard to the sample to obtain a doped sample;
(iv) analysing the doped sample using mass spectrometry to obtain ion peaks;
(v) comparing the identity and intensity of the ion peaks associated with the tagged standard with the additional ion peaks in the spectrum of the doped sample;
(vi) using the presence of said glycan to assist diagnosis of the disease or disorder.

In a further aspect, the present invention provides an isotopically-labelled glycan as described herein for use in a method of diagnosis, the method comprising:
(i) obtaining a sample suspected of containing a glycan associated with a disease or disorder from a patient;
(ii) selecting a tagged standard comprising an isotopically-labelled glycan corresponding to the glycan associated with the disease or disorder;
(iii) adding the tagged standard to the sample to obtain a doped sample;
(iv) analysing the doped sample using mass spectrometry to obtain ion peaks;
(v) comparing the identity and intensity of the ion peaks associated with the tagged standard with the additional ion peaks in the spectrum of the doped sample to identify, and optionally to quantify, the presence of one or more glycans in the sample;
(vi) using the presence of said one or more glycans to diagnose the disease or disorder.

In further aspects, the present invention provides an isotopically-labelled glycan as described herein for use in a method of diagnosis, and methods of diagnosis, the method comprising:
(i) selecting a tagged standard comprising an isotopically-labelled glycan corresponding to a glycan associated with a disease or disorder;
(iii) adding the tagged standard to a sample that has been obtained from a patient to obtain a doped sample;
(iv) analysing the doped sample using mass spectrometry to obtain ion peaks;
(v) comparing the identity and intensity of the ion peaks associated with the tagged standard with the additional ion peaks in the spectrum of the doped sample to identify, and optionally to quantify, the presence of one or more glycans in the sample;
(vi) using the presence of said one or more glycans to diagnose the disease or disorder.

Samples obtained from patients may be obtained using methods known in the art. Suitably, as the glycan(s) in the biological material taken from the patient may be conjugated to a protein backbone, the sample may be obtained by taking biological material from a patient and removing glycan material from the protein backbone enzymatic or chemical (hydrazinolysis) treatment. Suitably, the resultant material may be purified.

In a further aspect, the present invention provides a kit for identifying a glycan in a sample, the kit comprising:
(a) a tagged standard, the tagged standard comprising one or more isotopically-labelled glycans;
(b) instructions for doping a sample suspected of containing a glycan with the tagged standard to obtain a doped sample and analysing the doped sample using mass spectrometry.

Optionally, the kit may include mass spectrometry data for the tagged standard which may facilitate identification of analytes in the sample through easy identification of the ion peaks associated with the tagged standard.

The instructions may further comprise the step of comparing the ion peaks associated with the tagged standard with the additional ion peaks in the mass spectrum.

In some embodiments, the tagged standard is a mixture of isotopically-labelled glycans known to be a combination associated with a particular disease, disorder or biological process.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

Definitions

Isotopically-Labelled

Figure 1:
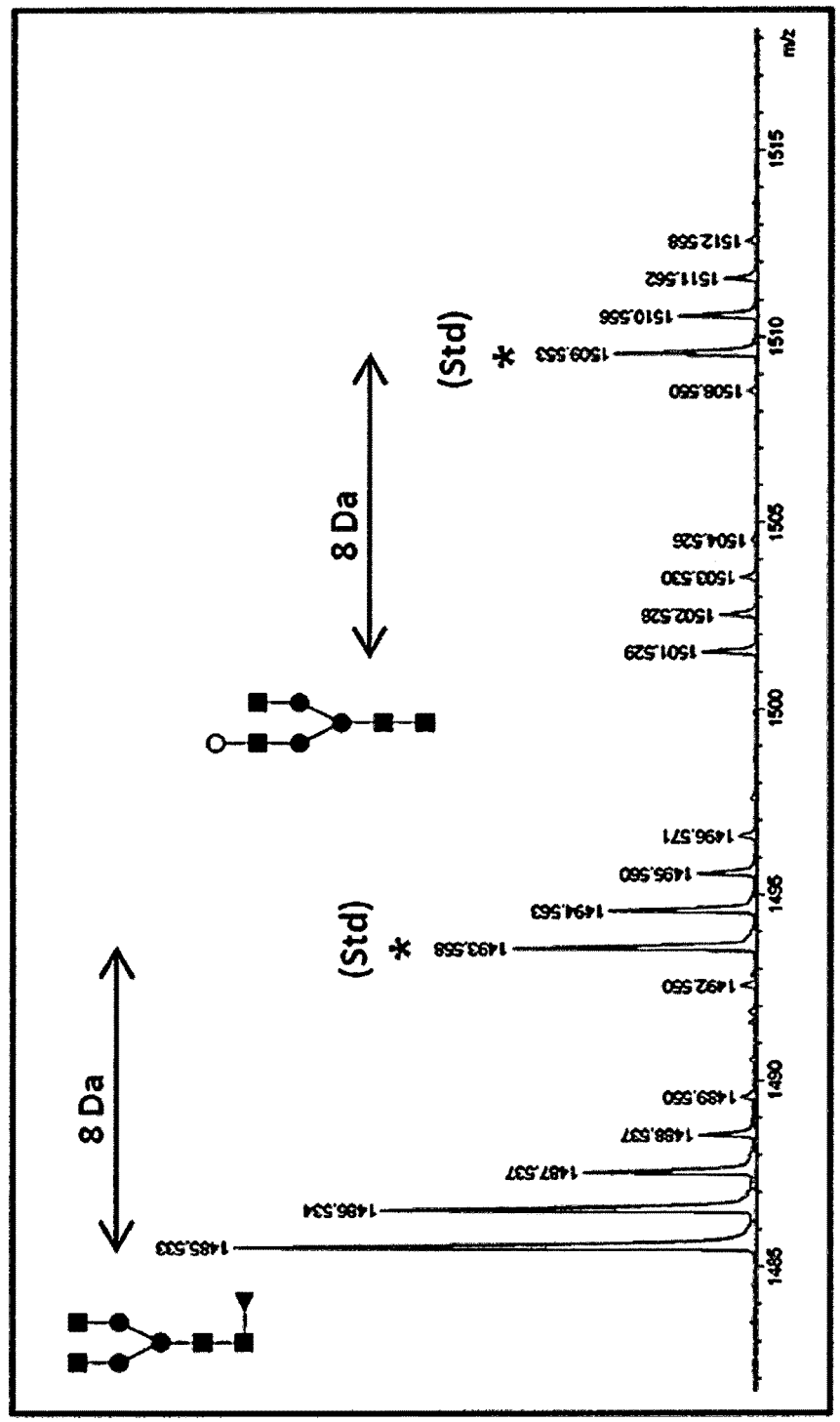
FIG. 1. A representative portion of a mass spectrum of a doped sample showing the ion peaks associated with an isotopically-labelled glycan and a corresponding analyte. The peaks indicates show the measured intensity of the ion peaks associated with the isotopically-labelled glycans of the tagged standard and the corresponding analyte glycans of the sample.

As used herein, isotopic labelling, isotopically-labelled, and other similar terms are used as is understood in the art. Specifically, an isotopically-labelled compound is a compound in which at least one atom of known position is enriched with an isotope other than the most abundant naturally-occurring isotope for that element. For example, methane may be $^{13}C$-isotopically-labelled, and have the structure $^{13}CH_4$, or deuterium-labelled. Deuterium-labelled methane may refer to a compound in which one or more of the four hydrogen atom positions associated with methane are enriched with $^2H$ (D). Common deuterium-labelled methane structures include $CDH_3$ and $CD_4$.

Isotopic-labelling refers to isotopic enrichment above natural abundance. Preferably, the isotopic purity at the enriched position is greater than 50%. For example, in $^{13}C$-isotopically-labelled methane, this means that 50% or more of the individual molecules comprise a $^{13}C$ atom. In embodiments of the present invention, the isotopic purity at the enriched position(s) is preferably greater than 80%.

More preferably, the isotopic purity at the enriched position(s) is greater than 90%.

In some preferred embodiments, the isotopic purity at the enriched position(s) is greater than 95%.

In some preferred embodiments, the isotopic purity at the enriched position(s) is greater than 97%.

In some preferred embodiments, the isotopic purity at the enriched position(s) is greater than 98%.

In some preferred embodiments, the isotopic purity at the enriched position(s) is greater than 99%.

Acyl Group

As used herein, an acyl group is a functional group derived by the removal of a hydroxyl group from a carboxylic acid. Common acyl groups include formyl (methanoyl), acetyl (ethanoyl), propionyl (propanoyl), benzoyl, and acrylyl (propenoyl). Other acyl groups of biological relevance include, but are not limited to, hydroxyethanoyl (glycolyl) and acyl groups derived from $C_{4-18}$-fatty acids (for example, butanoyl, hexanoyl, octanoyl, decanoyl, etc.) and hydroxylated fatty acids.

Acylation is the process of adding an acyl group to a compound using an acylating agent. In the context of the present invention, acylation occurs at a nucleophilic functional group, for example, an amino group or a hydroxyl group. Where more than one nucleophilic group is present, the order in which groups are acylated is determined by nucleophilicity and steric factors. Common acylating agents include acyl chlorides and acid anhydrides.

Isotopically-labelled acyl groups are those in which at least one atom of known position is enriched with an isotope other than the most abundant naturally-occurring isotope for that element, as defined herein. Examples include, but are not limited to, all combinations of $^{12}C$, $^{13}C$, $^{14}C$, $^{16}O$, $^{18}O$, H and D of formyl, acetyl, propionyl, benzoyl, and acrylyl groups available. Other isotopically-labelled acyl groups may also be used in methods of the present invention as appropriate. For example, an isotopically-labelled hydroxyethanoyl group (such as, for example, 1-$^{13}C_1$- or $^{13}C_2$-hydroxylethanolyl) may be used to provide an isotopologue of a glycan containing an N-glycolylneuramic acid unit. Similarly, isotopically-labelled acyl groups derived from fatty acids may be used to provide isotopologues of, for example, Lipid A.

In some embodiments, the isotopically-labelled acyl group is an isotopically-labelled acetyl group. Preferred isotopically-labelled acetyl groups Ac* include:
—($^{13}C$=O)$^{13}CH_3$, —(C=O)$^{13}CH_3$, —($^{13}C$=O)$CH_3$,
—(C=O)$CD_3$, —($^{13}C$=O)$^{13}CD_3$, —(C=O)$^{13}CD_3$,
—($^{13}C$=O)$CD_3$,
—($^{14}C$=O)$^{14}CH_3$, —(C=O)$^{14}CH_3$, —($^{14}C$=O)$CH_3$,
—(C=$^{17}O$)$CH_3$, or —(C=$^{18}O$)$CH_3$.

In preferred embodiments of the present invention, the isotopically-labelled acetyl group Ac* is selected from:
—($^{13}C$=O)$^{13}CH_3$, —(C=O)$^{13}CH_3$, or —($^{13}C$=O)$CH_3$. In particularly preferred embodiments of the present invention, the isotopically-labelled acetyl group Ac* is —($^{13}C$=O)$^{13}CH_3$.

Acylating agent as used herein is used as is understood in the art, that as, as a chemical reagent that provides an acyl group. Commonly used acylating agents include acyl chloride and anhydrides of carboxylic acids, although other acylating agents and methods will be apparent to one skilled in the art and may include, for example, the product of a reaction between a carboxylic and a suitable coupling reagent. In some embodiments, the isotopically-labelled acylating agent is an acyl chloride. Suitable acyl chlorides may be commercially available, or may be obtained using methods known in the art, for example through treatment of the corresponding carboxylic acid with thionyl chloride or oxalyl chloride.

In other embodiments, the isotopically-labelled acylating agent is an anhydride of a carboxylic acid, preferably an anhydride of acetic acid. In some embodiments, the isotopically-labelled acetylating agent is selected from: $(^{13}CH_3{}^{13}C=O)_2$, $(^{13}CH_3C=O)_2$, $(CH_3{}^{13}C=O)_2$, $(CD_3C=O)_2$, $(^{13}CD_3{}^{13}C=O)_2$, $(^{13}CD_3C=O)_2$, or $(CD_3{}^{13}C=O)_2$. In some preferred embodiments, the isotopically-labelled acetylating agent is $(^{13}CH_3{}^{13}C=O)_2$.

In some embodiments, a $^{14}C$-acylating agent, preferably a $^{13}C$-labelled acetic anhydride, may be used. The resultant glycans, labelled with $^{14}C$, may have utility as standards for glycan quantification using autoradiography.

Protecting Group

As used herein, protecting group refers to a moiety that is introduced into a molecule by chemical modification of a functional group in order to obtain chemo-selectivity during a subsequent reaction or to prevent unwanted degradation or side-reactions during subsequent reaction. A protecting group may also be referred to as a masked or masking group or a blocked or blocking group. By protecting a reactive functional group, reactions involving other unprotected reactive functional groups can be performed, without affecting the protected group; the protecting group may be removed, usually in a subsequent step, without substantially affecting the remainder of the molecule. See, for example, 'Protective Groups in Organic Synthesis' (T. Green and P. Wuts, Wiley, 1999).

Examples of protecting groups are well-known in the art, and the following examples are provided for illustration and not by way of limitation.

For example, a hydroxy group may be protected as an ether (—OR) or an ester (—OC(=O)R), for example, as: a t-butyl ether; a methoxymethyl (MOM) or methoxyethoxymethyl (MEM) ether; a benzyl (Bn), benzhydryl (diphenylmethyl), or trityl (triphenylmethyl) ether; a trimethylsilyl or t-butyldimethylsilyl ether; or an acetyl ester (—OC(=O)CH$_3$, —OAc) or benzoyl ester (—OC(=O)Ph, Bz).

For example, an aldehyde or ketone group may be protected as an acetal or ketal, respectively, in which the carbonyl group (>C=O) is converted to a diether (>C(OR)$_2$), by reaction with, for example, a primary alcohol. Thio-acetals and thio-ketals are also known in the art.

For example, a polyhydric moiety may be protected as an acetal group, in which for example two hydroxyl groups on carbon atoms adjacent to each other (HO—CR$_2$CR$_2$—OH; often called a glycol group) react with an aldehyde or ketone to from a ring comprising an —O—CR$_2$—O— linkage, as shown below.

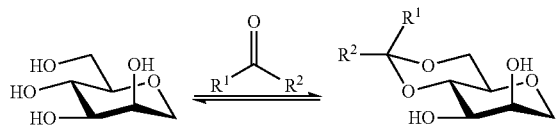

Acetals are typically formed under dehydrating conditions (for example, under Dean-Stark conditions or using a Soxhlet extractor) with acid catalysis and may be removed by acid catalysis and an excess of water, or by other methods known in the art.

For example, an amine group may be protected as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO$^-$) or azide.

In some embodiments of the present invention, amine functions in hexosamine sugar donors are protected by phthalimide, TRoc, trichloroacetyl, dimethylacetyl groups. This facilitates β-selective formation of glycosidic bonds and prevents unwanted oxazoline formation in these reactions. In some embodiments, amine functions may be protected as azides, which may facilitate the stereoselective formation of α-glycosidic linkages.

For example, a carboxylic acid group may be protected as an ester, for example, as: a C$_{1-7}$ alkyl ester (e.g. a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

In some embodiments, the present invention uses orthogonal protecting group strategies to assemble oligosaccharides and oligosaccharide-containing structures. Orthogonal protection is a strategy known in the art, and involves judicious selection of multiple protecting groups to enable deprotection of one or more functional groups of a molecule using a dedicated set of reaction conditions with affecting other protecting groups elsewhere in the molecule. For example, one protecting group used may be acid labile (e.g. an acetal), another protecting group used may be base labile (e.g. an FMOC group), while a further protecting group used may be removed using hydrogenation conditions (e.g. a benzyl ether). As described herein, where multiple positions within a structure may each independently be a protecting group, said protecting groups may be the same or different. Different protecting groups may be orthogonal to each other and consequently facilitate chemo-selective reaction through selective deprotection of one protecting group in the presence of another. Purely by way of example, in an oligosaccharide comprising the motif

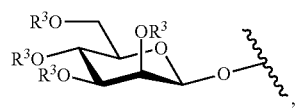

wherein each R$^3$ is independently a protecting group, each R$^3$ may be a protecting group of the same type, or each R$^3$ may be independently the same or different to any other R$^3$ group. Through use of R$^3$ protecting groups that are orthogonal, selective deprotection and reaction can occur at C2, C3, C4 or C6.

Calculation of Concentrations Using Isotopic Dilution

Methods according to the present invention and isotopically-labelled glycans provided by the present invention can be used to determine the concentration of an analyte of interest, for example, a natural glycan, in a sample. Suitable samples may include glycans released from proteins, natural glycoconjugates, and the products of recombinant protein production.

In some methods according to the present invention, a sample suspected to contain at least one glycan is obtained following, for example, release from a protein by hydrazinolysis or enzymatic cleavage with peptide glycosidase. To this sample, a known amount of a "tagged standard" is added to obtain a doped sample. The tagged standard comprises at least one isotopically-labelled glycan of known concentration, and in some embodiments comprises a mixture of isotopically-labelled glycans with known concentrations of all components.

The doped sample is then analysed using mass spectrometry to acquire spectra. Optionally, during the analysis and acquisition, information regarding fragmentation of selected ions may be obtained. This fragmentation analysis may aid determination of both the overall structure of the glycan of interest and of the relative and absolute weaknesses of bonds present. This is of especial relevance to methods and embodiments of the present invention in which isotopically-labelled monosaccharide units have been introduced into the isotopically-labelled glycan at one or more pre-determined positions in the oligosaccharide sequence, for example, using chemo-enzymatic methods as described herein.

Ion peaks in the acquired spectra are then assigned (being identifiable owing to fixed mass increments) and may be quantified through comparison with the ion peaks known to be associated with the tagged standard.

For example, a particular natural N-glycan having a [(2-acetamido-2-deoxy-β-D-glucopyranosyl-(1→2)-α-D-mannopyranosyl)-(1→6)]-[2-acetamido-2-deoxy-β-D-glucopyranosyl-(1→2) -α-D-mannopyranosyl-(1→3)]-β-D-mannopyranosyl-(1→4)-2-acetamido-2-deoxy-β-D-glucopyranosyl-(1→4)-2-acetamido-2-deoxy-α,β-D-glucopyranose motif may be identified through use of a tagged standard comprising an isotopologue in which the acetyl groups in this heptasaccharide motif are each $^{13}C_2$-isotopically-labelled, which may be obtained as described herein. This results in an isotopically-labelled N-glycan having mass incremented 8 Da relative to the natural N-glycan, but with the corresponding associated mass spectrometry ion envelope (as shown in FIG. 1).

Furthermore, the amount of the analyte glycan may be quantified through comparison of the ion peak intensities, thereby allowing the amount of the analtye glycan to be quantified (the peak intensities of each isotopologue are proportional to their amounts in the sample). As the isotopically-labelled glycan ionises with the same efficiency as the corresponding analyte glycan, the relative intensities are proportional to their relative concentrations (Equation 1). The method further allows for the quantification of an analyte in complex mixtures comprising multiple glycans, both in terms of amount and relative abundance (Equations 2, 3, and 4). Using methods of the invention and these equations, analytes in complex mixtures can be quantified. It will be understood that use of Equations 1 to 4 is generally applicable to methods of the present invention, and that Equations 1 to 4 are explained without limitation with reference to this example method. For simplicity, "light" refers to non-isotopically-labelled glycans and "heavy" to the corresponding higher molecular weight isotopically-labelled glycans.

$I_i$ Peak intensity of the "light" isotopologue i
$I^*_j$ Peak intensity of the "heavy" isotopologue j
$m_i$ Amount of the "light" isotopologue i
$m^*_j$ Amount of the "heavy" isotopologue j
$m_T$ Total amount of the "light" glycan in the sample
$m^*_T$ Total amount of the "heavy" glycan in the sample
$X_i$ Relative abundance of the "light" isotopologue i in the non-isotopically analyte glycan
$X^*_j$ Relative abundance of the "heavy" isotopologue j in the isotopically labelled glycan $$\frac{I_i}{m_i} = \frac{I^*_j}{m^*_j} \quad \text{[Equation 1]}$$

$$m_i = m_T \times X_i \quad \text{[Equation 2]}$$

$$m^*_j = m^*_T \times X^*_j \quad \text{[Equation 3]}$$

$$m_t = \frac{I_i \times m^*_T \times x^*_j}{I^*_j \times X_i} \quad \text{[Equation 4]}$$

It will be appreciated that while the above equations provide reasonable quantification of the glycans in a sample by comparison to their "heavy" corresponding isotopologue standard, for complex mixtures and spectra in which certain peaks are detected at saturated concentration, more detailed methods may be desirable. For example, if the most abundant peak of a standard is saturated, simply using that peak in the above equations may give an inaccurate quantification. To address this problem, the following provides details of isotopic dilution analysis (study of linearity and selection of internal standard isotopologues for the calculation of the glycan concentration in a sample). This method uses the ion peaks associated with different "heavy" isotopologues to calculate a function. This function may be used to relate the peak intensity of the peak to be quantified to the amount of the isotopologue associated with that peak, thereby mitigating this potential inaccuracy. Once again, the following is provided for illustration and without limitation.

I. Linearity Determination

Knowing the total amount of "heavy" isotopologues for a given glycan ($m_T$*) added to the sample and the corresponding relative abundance ($X_j$*) of each of its constituent "heavy" isotopologues, it is possible to calculate the amount of each "heavy" isotopologue ($m_j$*) in the sample using equation 3. This may account for different synthetic "heavy" isotopologues, for example, having differently isotopically labelled acetyl groups, and/or the various peaks associated with the isotopic envelope for a given "heavy" glycan. Suitably, the various peaks associated with the isotopic envelope are used. The theoretical abundances of these isotopic envelope peaks may be derived from the known natural abundances of the various isotopes, calculated as a probability given the empirical formula of the molecule.

By using the ion peak intensities obtained for these different "heavy" isotopologues of a glycan in the isotopically-labelled standard ($I_j$*) and their relative abundances ($m_j$*), a function correlating peak intensities and glycan amount can be calculated by linear regression (I being a function of m):

$$I = bm + a \quad \text{[Equation 5]:}$$

where the coefficients b and a correspond to the slope and the intercept, respectively, which have been calculated by minimum least squares fit (Equations 6 and 7).

$$b = \frac{\sum (m_j^* - \overline{m_j^*})(I_j^* - \overline{I_j^*})}{\sum (m_j^* - \overline{m_j^*})^2}$$ [Equation 6]

$$a = \overline{I_j^*} - b\overline{m_j^*}$$ [Equation 7]

The coefficient of determination $R^2$ can be also calculated and used as a measure of the fitting quality. If $R^2$ is lower than a given value, for example, if $R^2$ is less than 0.99, the data point corresponding to the most abundant "heavy" isotopologue may be discarded and the function and $R^2$ are calculated again by linear regression. This process may be repeated until all the linearity conditions defined for $R^2$ are matched. This iterative process improves the accuracy of the function.

Once a function with the appropriate $R^2$ is obtained, the linearity range defined is the limits of the maximum and minimum peak intensity and the corresponding glycan isotopologue amount values. All the peaks within this linear range may be considered of sufficient quality to allow a very accurate quantification.

II. Calculation of the Amount of Non-Labelled Glycan in the Sample

As described, a linear function may be obtained using the known properties of a tagged standard "heavy" glycan isotopologue mixture. These "heavy" glycans must give peak intensities in the previously established linear range and with a suitable minimum signal to noise ratio, for example, higher than five.

This way, the amount of an individual "light" glycan isotopologue satisfying the above criteria (within the maximum and minimum peak intensities) ($m_i$) can be calculated from the function obtained as described above and improved by the by linear regression iterative improvement described above.

$$m_i = \frac{(I_i - a)}{b}$$ [Equation 8]

Because the "light" glycan itself has an isotopic envelope associated with its parent mass spectrometry peak (for example, the natural abundance of $^{13}C$) a more accurate analysis of the total amount of the analyte glycan corrects for this using the theoretical natural abundance of that "exact mass" isotopologue ($X_i$), which can be easily theoretically calculated using the statistical probability of these isotopes being present.

Thus, once the amount of an isotopologue of the "light" ($m_i$) has been calculated, and knowing the relative abundance of that isotopologue ($X_i$), the analyte glycan in the sample ($m_T$) can be calculated:

$$m_T = \frac{(I_i - a)}{b \times X_i}$$ [Equation 9]

Accordingly, in some embodiments, methods of quantitatively determining the analyte glycan content of a sample may use a tagged standard comprising a plurality of "heavy" isotopologues of said analyte glycan, the method including the steps of
(i) correlating the relative intensities of the ion peaks associated with each "heavy" isotopologue ($I_j^*$) with the known abundance of that glycan in the standard ($m_j^*$) to obtain $I_j$ as a linear function of $m_j$;
(ii) optionally calculating the coefficient of determination $R^2$ for the correlation and discounting the most abundant ion peak if the $R^2$ value is greater than a predetermined value;
(iii) optionally repeating step (ii) one or more times;
(iv) using said function to calculate the amount of a "light" isotopologue of the analyte glycan;
(v) optionally using the total amount of the "light" isotopologue of the analyte glycan to determine the total amount of analyte glycan present.

Suitably, the $R^2$ value may be great than or equal to 0.99.

Furthermore, the present invention further provides a method of identifying a "light" isotopologue in a sample, the method comprising adding a known amount of a tagged standard comprising a plurality of corresponding "heavy" isotopologues (said "heavy" isotopologues being isotopically labelled), analysing the mixture by mass spectrometry and quantifying the amount of "light" isotopologue by comparison of the relative intensity of the ion peaks associated with the "heavy" isotopologues and with the "light" isotopologue.

This quantification may include the steps of:
(a) correlating the relative intensities of the ion peaks associated with each "heavy" isotopologue (Ij*) with the known abundance of that isotopologues in the standard (mj*) to obtain Ij as a linear function of mj;
(b) optionally calculating the coefficient of determination $R^2$ for the correlation and discounting the most abundant ion peak if the $R^2$ value is greater than a predetermined value;
(c) optionally repeating step (ii) one or more times;
(d) using said function to calculate the amount of analyte "light" isotopologue in the analyte sample;
(v) optionally using the total amount of the "light" isotopologue to determine the total amount of analyte glycan present.

It will be appreciated that the method may be applied to any suitable molecules available in isotopically-labelled form, the method being suitable for the glycan standards described herein but not necessarily limited to glycan molecules.

Fragmentation

The generation and analysis of molecular fragment ions during mass spectrometry experiments is of considerable use in structural determination. Various techniques for the generation and detection of such fragment ions are known in the art and include, but are not limited to, collision-induced dissociation (CID) and tandem mass spectrometry (variously also called MS/MS and MS2). Analysis and quantification of these fragments may aid partial or complete structural determination, and may be especially useful for detecting a given molecule in the presence of other molecules of the same notional molecular weight. In the context of the field of the present invention, fragment analysis may also be used to identify weaker bond linkages in analytes and to discriminate between isobaric structures.

In some embodiments of the present invention, isotopically-labelled monosaccharide units are incorporated chemo-enzymatically into glycan structures, for example, using the enzymatic elongation methods described herein.

The use of these glycans for the generation of fragmentation patterns is of particular value for discriminating between isobaric glycan structures using mass spectrometry techniques.

This can be achieved through the identification and/or assignment of diagnostic fragments and/or determination of the weakest linkages in a particular isomer.

Sugar Abbreviations

As used herein, saccharide abbreviations are used as is commonly understood in the art. The suffix "N" indicates the corresponding amino sugar, while "NAc" indicates the corresponding N-acetyl amino sugar.

Glc—glucose
Gal—galactose
Man—mannose
Rha—rhamnose
Fru—fructose
Fuc—fucose
Mur—muramic acid
Neu—neuraminic acid
Kdo—keto-deoxyoctulosonate Glycans The term glycan can be used to refer to any saccharide (mono-, oligo- or poly-) in free form or forming a carbohydrate portion of a glycoconjugate molecule such as a glycoprotein, proteoglycan or glycolipid. Glycans are important molecules involved in virtually every biological structure and process. Constituent monosaccharides generate a much greater combinatorial diversity than nucleic or amino acids, and further diversity arises from covalent modification of glycans. The total glycan repertoire (glycome) of a given organism is thus much more complex and dynamic than the genome or proteome.

Linkages between monosaccharides can be in α- or β-form, chains can be linear or branched and glycan modifications can include acetylation and sulfation. Glycoproteins carry one or more glycans covalently attached to a polypeptide via N or O linkages.

O-glycans are linked to hydroxyl groups of serine or threonine residues. N-glycans are sugar chains linked via a side-chain nitrogen (N) to an asparagine residue. They share a common pentasaccharide region of two mannose residues, linked separately by α1-3 and α1-6 linkages to a central mannose, which in turn is linked by a β1-4 linkage to a chitobiose core consisting of two β1-4-linked GlcNAc residues. Based on further processing of the pentasaccharide, N-glycans are divided into three main classes: (i) high-mannose complex (iii) hybrid types.

High-mannose N-glycans have only unsubstituted mannose residues (typically 5-9) attached to the chitobiose core. Hybrid N-glycans contain both unsubstituted terminal mannose residues and mannose residues with a GlcNAc, which initiate "antennae" to which additional monosaccharides may be added. Complex N-glycans have GlcNAc residues added at both α3 and α6 mannose sites, do not have extra-pentasaccharide mannose residues and are found in bi, tri and tetraantennary forms.

Proteoglycans have one or more glycosaminoglycan (GAG) chains attached through a core region ending with a xylose to the hydroxyl groups of a serine residue. The most important glycolipids are glycosphingolipids, which consist of a glycan usually linked via a glucose or galactose to the terminal hydroxyl group of a ceramide lipid moiety, which is composed of the long chain amino alcohol sphingosine and a fatty acid.

Glycan Binding Proteins

Many of the specific biological roles of glycans are mediated via recognition by glycan binding proteins (GBPs). GBPs include lectins, glycosaminoglycan binding proteins and glycan-specific antibodies. Lectins often bind to terminal regions of glycan chains through carbohydrate recognition domains. Due to low affinity binding, multivalent CRD-glycan interactions are often required for interactions with biological relevance.

Glycan Processing

Glycans are primarily synthesised by glycosyltransferase enzymes which assemble monosaccharide moieties into glycan chains.

Glycosyltransferase enzymes have in common the property of being able to catalyse transfer of a monosaccharide of a simple nucleotide sugar donor (for example, UDP-Gal, GDP-Fuc or CMP-Sia) to an acceptor substrate.

Glycoconjugate biosynthesis is initiated by glycosyltransferase enzymes which attach saccharides to a polypeptide side chain or sphingolipid base. For example, in the case of N-glycans, oligosaccharyltransferase transfers the glycan Glc3Man9GlcNAc2 to the side chain of asparagine.

The majority of glycosyltransferases elongate glycan chains. Linear or branched chains are built by sequential glycosylation, often by distinct glycosyltransferases. That is, the product of glycosylation by one enzyme produces the preferred substrate for another. Examples of glycosyltransferases include galactose-1-phosphate uridyl-transferase (GalT), N-acetylgalatosaminyl-transferase (GalNAcT), fucosyl transferase (FuT) and sialyltransferase (SialT, which catalyze the addition of galactose, N-acetylglucosamine, fucose and sialic acid residues, respectively.

Glycosidases are glycan processing enzymes which remove monosaccharide moieties to form intermediates which are then acted upon by glycosyltransferases. This type of processing is particularly important in the biosynthesis of N-glycans; action of glycosidase enzymes on the Glc3Man9GlcNAc2 allows formation of intermediates necessary for processing ultimately to high-mannose, complex and hybrid type N-glycans described above.

Chemo-Enzymatic Synthesis of Isotopically-Labelled Glycans

Advances in the exploration of microbial resources and improved production of mammalian enzymes have established the use of glycosyltransferases as an efficient tool for glycan synthesis (Blixt, 2006; Ruiz, 2001; Serna, 2010, Zou, 2011). Using the appropriate sequence of regio- and stereo-specific transferase enzymes and sugar donor building blocks, complex glycan structures can be assembled through sequential enzymatic elongation. Similarly, it may be desirable to first truncate a core motif, for example, to facilitate preparation of asymmetric isotopically-labelled glycan standards derived from the biantennary heptasaccharide 18 $^{13}C_8G0(Bn_5)$. This truncation may be achieved by enzymatic hydrolysis.

Accordingly, methods described herein for the synthesis of isotopically-labelled glycans for use as mass spectrometry standards include an enzymatic derivatisation step.

In some embodiments, methods for the synthesis of isotopically-labelled glycans include the use of an appropriate hydrolase on an isotopically-labelled oligosaccharide as described herein to truncate the isotopically-labelled oligosaccharide. In other words, the present invention may provide methods for the enzymatic truncation of one or more sugar units from an isotopically-labelled oligosaccharide core motif.

The resultant truncated oligosaccharide may then itself undergo enzymatic elongation to incorporate one or more further sugar units. In some embodiments of the present invention, appropriate transferases in combination with suitable sugar donors are used sequentially in a stepwise fashion to assemble isotopically-labelled glycans. The transferases may be recombinant glycosyltransferases, transglycosidases, endoglycosidases or mutated glycosidases. The resultant glycans may have utility in methods of the present invention described herein. In some embodiments, the enzymatic elongation step(s) occurs on an oligosaccharide comprising an isotopically-labelled motif as described herein, which may variously be termed a core oligosaccharide, a core motif, and an isotopically labelled starting oligosaccharide. In other words, in some methods of the present invention, an isotopically-labelled starting oligosaccharide is chemoselectively elongated to incorporate additional sugar units, thereby affording further isotopically-labelled glycan standards for use in mass spectrometry.

The sugar donor used in each elongation step may optionally be isotopically-labelled. In some embodiments, only the original isotopically-labelled motif is isotopically-labelled in the resultant glycan. In other embodiments, at least one isotopically-labelled sugar unit is incorporated during the enzymatic elongation step(s). As discussed above, the incorporation of specific isotopically-labelled sugar units at specific positions has utility in the analysis of fragmentation patterns in mass spectrometry.

Alternatively, the enzymatic elongation occurs on a motif that is not isotopically-labelled. Instead, one or more isotopically-labelled sugar units is incorporated during the enzymatic elongation step(s) to afford an isotopically-labelled glycan which may be used as appropriate in the methods of identifying a glycan in a sample as described herein.

The chemoenzymatic elongation step may be repeated multiple times. For example, using monosaccharide sugar donors, 20 cycles of chemo-enzymatic elongation may introduce an additional 20 monosaccharide units. It will be appreciated that further units may be incorporated at the termini of antennae, or may be incorporated onto one of the sugar units of the core oligosaccharide.

In some embodiments, the chemoenzymatic elongation step may utilise a sugar donor which is a disaccharide or oligosaccharide and/or which is conjugated to a lipid, peptide or protein.

In some embodiments, the enzymatic derivatisation step may comprise one or more of an epimerisation step, a transglycosylation step, or a post-translational modification step. These may be in addition to elongation or truncation.

Figure 2:
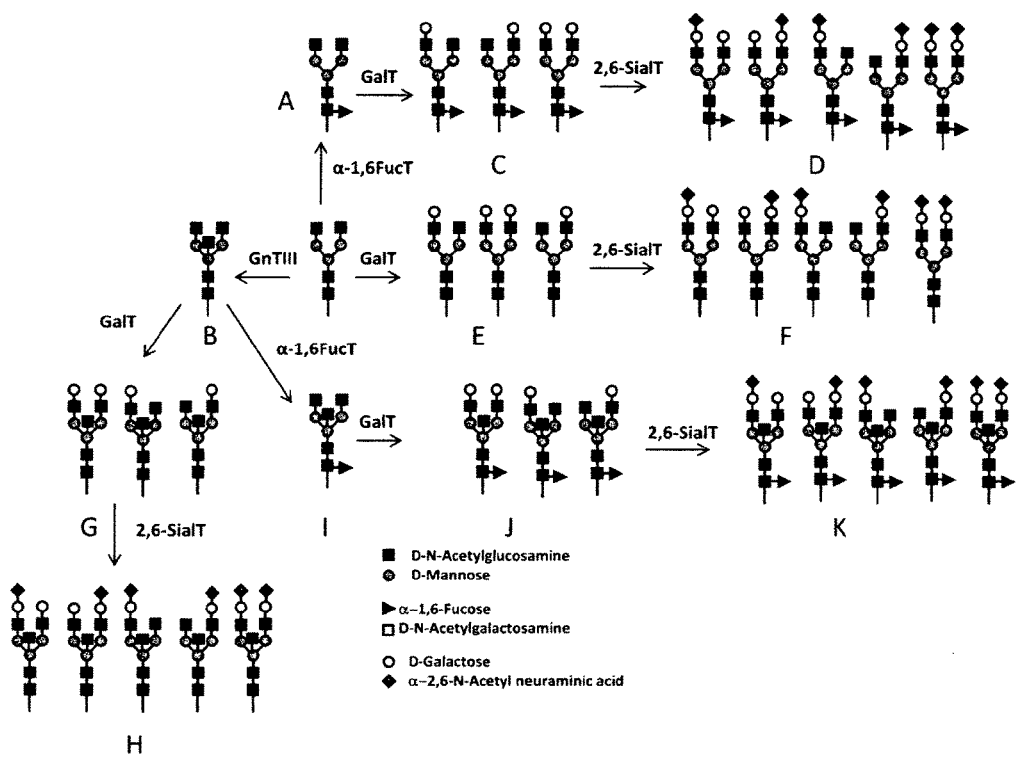
FIG. 2. A schematic representation of possible combinations of enzymatic elongation steps to afford isotopically-labelled N-glycans.

FIG. 2 demonstrates use of the method to assemble a variety of glycans and glycan mixtures. Any sugar unit may be isotopically-labelled. In some preferred embodiments, each acetyl group in the starting heptasaccharide, [(2-acetamido-2-deoxy-β-D-glucopyranosyl-(1→2)-α-D-mannopyranosyl)-(1→6)]-[2-acetamido-2-deoxy-β-D-glucopyranosyl-(1→2)-α-D-mannopyranosyl-(1→3)]-β-D-mannopyranosyl-(1→4)-2-acetamido-2-deoxy-β-D-glucopyranosyl-(1→4)-2-acetamido-2-deoxy-α,β-D-glucopyranose is isotopically-labelled. A chemical synthesis of this isotopically-labelled starting material is described below. This isotopically-labelled starting core oligosaccharide is referred to herein as $^{13}C_8$-G0.

FIG. 2 shows a series of sequences beginning with this starting heptasaccharide $^{13}C_8$-G0. Incubation with a recombinant core α1,6 fucosyltransferase furnishes core fucosylated structure A, which may be further galactosylated (panel C) and sialylated (panel D). Direct galactosylation of the starting heptasaccharide with a bovine milk galactosyltransferase in the presence of UDP-galactose accesses both mono-galactosylated isomers and the fully galactosylated N-glycan (panel E). Further treatment with a recombinant α2,6 SialylT furnishes compound panel F. A bisecting GlcNAc residue may be introduced by virtue of a recombinant GnTIII (compound B). Galactosylation of this product then leads to the panel G bisecting compounds, and subsequent sialylation affords compound panel H. α-1,6 fucosylation of bisecting compound A leads to bisecting and core fucosylated glycan I, which may be galactosyleted towards panel J and finally sialylated to afford compound (panel K).

The synthetically-provided isotopically-labelled core oligosaccharides may be protected during the enzymatic derivatisation step, that is, they may have one or more protecting groups. For example, as described herein, $^{13}C_8$-G0 may be obtained via $^{13}C_8$-benzyl [(2-acetamido-2-deoxy-β-D-glucopyranosyl-(1→2)-α-D-mannopyranosyl)-(1→6)]-[2-acetamido-2-deoxy-β-D-glucopyranosyl-(1→2)-α-D-mannopyranosyl-(1→3)]-β-D-mannopyranosyl-(1→4)-2-acetamido-3,6-di-O-benzyl-2-deoxy-β-D-glucopyranosyl-(1→4)-2-acetamido-3,6-di-O-benzyl-2-deoxy-β-D-glucopyranoside, referred to herein as $^{13}C_8$-G0(Bn$_5$). This benzylated heptasaccharide may itself be used as an isotopically-labelled core motif for the enzymatic derivatisation step(s). As described herein, semi-protected core motifs may be suitable substrates for chemoselective enzymatic elongation and the presence of the protecting groups may have particular advantages, for example, by acting as chromophores for peak detection during HPLC analysis and purification and by aiding separation of different products, for example, isomeric glycans.

It will be appreciated that other non-human e.g. plant or parasite specific glycans may be assessed in a similar fashion and, by starting with an isotopically-labelled motif as described above, obtained as isotopically-labelled compounds with a fixed mass increment which is easily detectable in mass spectrometry experiments. Likewise the chemosynthetic preparation of a larger library N-glycans including higher branched complex, hybrid and high mannose type glycans with systematic variations of the number of antennae, branching pattern and core modifications may be obtainable starting from a very reduced number of core structures, which are preferably isotopically-labelled and obtainable using methods according to the present invention. A library based on these core structures reflects the structural variation of N-glycans found in eukaryotic glycoproteins and the most common glycan structures presented on recombinant glycoproteins.

The following discussion relates to modification of the heptasaccharide N-glycan core referred to herein as $^{13}C_8$-G0. It is provided for illustration, and is not intended to limit the invention. Other glycan cores may equally be envisaged.

The partially deprotected $^{13}$C-labelled N-glycan $^{13}C_8$-G0 (Bn$_5$) (13) was evaluated as precursor for the preparation and isolation of asymmetric N-glycan structures. By taking advantage of the hydrophobicity and UV absorbance of the penta-benzylated glycans, the present inventors have found that the presence of these 5 benzyl groups in the core N-glycan structure facilitates the chromatographic separation of different glycans and even isomeric structures after a partial enzymatic elongation.

A series of experiments in order to control a partial galactosylation of the substrate with bovine milk β-1,4- galactosyltransferase were performed, showing not only that the semi-protected N-glycan $^{13}C_8$-G0(Bn$_5$) was a suitable substrate for the enzyme but also the possibility of obtaining a mixture of G0-G1-G2 structures, all of them $^{13}C$-labeled. The analysis of this mixture by UPLC-MS, in reverse phase using a C18 column, permitted the separation of the different compounds and also the two isomers of the mono-galactosylated N-glycan $^{13}C_8$-G1(Bn$_5$), and also quantify their relative composition by the use of the UV-detector. The use of proper conditions during the enzymatic transformation of $^{13}C_8$-G0(Bn$_5$) yielded the mono-galactosylated biantennary N-glycan $^{13}C_8$-G1(Bn$_5$) in more than 45% in the form of its two different isomers 3-LacNAc and 6-LacNAc.

The purification of both mono-galactosylated isomers separately by semipreparative-HPLC in miligram scale was achieved as confirmed by MALDI analysis and NMR analysis. The complete deprotection of the core by hydrogenolysis provided two isomeric $^{13}C$-labeled standards $^{13}C_8$-G1$^3$ and $^{13}C_8$-G1$^6$ for use in N-glycan quantitative analysis. The isomer $^{13}C_8$-G1$^6$ could also be enzymaticaly fucosylated for the preparation of the standard $^{13}C_8$-G1$^6$F, as confirmed by MALDI-Tof MS.

Another strategy to obtain isomeric asymmetric isotopically-labelled N-glycans for use as mass spectrometry standards consisted of the use a β-galactosidase from *Aspergillus oryzae* on the bis-galactosylated $^{13}C_8$-G2(Bn$_5$) compound (Table 1). A different distribution of glycans was observed during this transformation, in which the inventors could determine a different activity of the hydrolase on the two isomeric mono-galactosylated structures. This different specificity of the enzyme provided only one of the mono-galactosylated compound in near 50% yield and the non-galactosylated compound $^{13}C_8$-G0(Bn$_5$).

TABLE 1

| | BE4-61-G2 | Galase | Time | T (° C.) | G2 | G1 | G1(*) | G0 |
|---|---|---|---|---|---|---|---|---|
| 1 | 5 µg | 30 mU | 5 h | 30 | 14 | 9 | 44 | 33 |
| 2 | 5 µg | 15 mU | 5 h | 30 | 18 | 10 | 46 | 25 |
| 3 | 5 µg | 8 mU | 5 h | 30 | 35 | 10 | 43 | 12 |
| 4 | 5 µg | 15 mU | 18 h | 30 | 6 | 4 | 38 | 52 |

The same strategy was employed for the preparation of a variety of $^{13}C$-labelled sialylated standards from the bis-galactosylated $^{13}C_8$-G2(Bn$_5$) using a α-2,3-sialyltransferase from *Pasteurella multocida* expressed in *E. coli* to give the two mono-sialylated and the bis-sialylated glycans derived from the biantennary structure. This mixture of semi-protected compounds was resolved by UPLC-MS, which allowed the inventors to determine their relative composition (Table 2).

TABLE 2

| | G2(Bn$_5$) | CMP-NeuNAc | 2,3-SialT (new) | Time | T(° C.) | G2 | G2A1 | G2A1(*) | G2A2 |
|---|---|---|---|---|---|---|---|---|---|
| 1 | 10 µg/5 nmol | 4 eq | 5 mU | 30 min | 37 | 16 | 25 | 23 | 36 |
| 2 | 20 µg/10 nmol | 4 eq | 10 mU | 30 min | 37 | 22 | 23 | 23 | 32 |

This reaction was also applied to the mixture of partially galactosylated compounds G0/G1/G2 obtained previously. The partial α-2,3-sialylation of this mixture yielded a mixture of 9 structures which could be resolved by UPLC-MS, identifying the presence of $^{13}C_8$-G0(Bn$_5$) and $^{13}C_8$-G2(Bn$_5$), both isomers of the mono-galactosylated compound $^{13}C_8$-G1(Bn$_5$), both isomers of the mono-sialylated compound $^{13}C_8$-G1A1 (Bn$_5$), both isomers of the mono-sialylated compound $^{13}C_8$-G2A1(Bn$_5$) and the bis-sialylated biantennary structure $^{13}C_8$-G2A2(Bn$_5$). This strategy can therefore be used to obtain up to 5 new sialylated $^{13}C$-labeled N-glycans after purification and deprotection.

The sialylation reaction was then performed in the mg scale in order to obtain the corresponding sialylated standards. The previously prepared semiprotected $^{13}C_8$-G1$^3$Bn$_5$ was sialylated with α-2,3-sialyltransferase from *P multocida* obtaining the sialylated compound $^{13}C_8$-G1$^3$Bn$_5$. The reaction was not complete but the sialylated compound could be isolated by semipreparative-HPLC. Also, the sialylation of $^{13}C_8$-G2(Bn$_5$) in mg scale afforded a mixture of the sialylated standards $^{13}C_8$-G2A1$^3$(Bn$_5$), $^{13}C_8$-G2A1$^6$(Bn$_5$) and $^{13}C_8$-G2A2 (Bn$_5$) which could be separated by semipreparative-HPLC.

The sialylation reaction of $^{13}C_9$-G2(Bn$_5$) with a human α-2,6-sialyltransferase expressed in recombinant CHO cells was also controlled in order to obtain the corresponding mono- and bis-sialylated structures. The reaction using the partially protected $^{13}C_8$-G2(Bn$_5$) as substrate and only one equivalent of sialic acid donor yielded 26% of the mono-sialylated compound. By contrast, the use of an excess of donor gave the bis-sialylated compound as the only product. Both compounds, mono- and bis-sialylated, could be resolved by UPLC-MS. This reaction was also performed on the G0/G1/G2 mixture obtained previously by partial galactosylation. Analogous to the previous results with the α-2,3-sialyltransferase, the partial sialylation of the mixture containing 3 galactosylated compounds afforded a mixture of 4 new $^{13}C$-labeled 2,6-sialylated N-glycans, which could be resolved by UPLC-MS. The relative composition of the mixture was determined identifying the bis-2,6-sialylated biantennary N-glycan $^{13}C_8$-G2S2(Bn$_5$), the mono-2,6-sialylated compound $^{13}C_8$-G1S1(Bn$_5$) into its two isomeric forms separately and the other mono-sialylated compound $^{13}C_9$-G2S1(Bn$_5$) (Table 3).

TABLE 3

| | G2 (Bn$_5$) | CMP-NeuNAc | 2,6-SialT | time | G2S2 | G2S1 | G2 |
|---|---|---|---|---|---|---|---|
| 1 | 10 µg/5 mmol | 4 eq | 1 mU | 2 h | 98 | 1 | 1 |
| 2 | 10 µg/5 mmol | 1 eq | 0.25 mU (0.25 nmol/min) | 30 min | — | 10 | 90 |
| | | | | 1 h | — | 15 | 85 |
| | | | | 4 h | 2 | 26 | 72 |
| | | | | 24 h | 7 | 40 | 53 |

The core oliogsaccharide $^{13}C_8$-G0(Bn$_5$) can be also modified for the preparation of other asymmetric glycan standards derived from the biantennary structure but with only one terminal GlcNAc. These truncated mono-antennary structures can be obtained by enzymatic hydrolysis of the terminal glucosamines in $^{13}C_8$-G0(Bn$_5$). The benzyl groups present in the starting molecule again help in the purification of the resulting structures after the enzymatic hydrolysis. For this purpose, a N-acetyl glucosaminidase from *Conavalia ensiformis* was used over the partially protected substrate $^{13}C_8$-G0(Bn$_5$). The optimization of the reaction allowed the inventors to obtain a mixture of the starting material, the two isomers of the mono-antennary structure $^{13}C_6$MGn$^3$(Bn$_5$) and $^{13}C_6$-MGn$^6$(Bn$_5$) respectively and the product of double hydrolysis $^{13}C_4$-Man3(Bn$_5$). As the glucosaminidase removes $^{13}C$-labeled GlcNAc moieties, the resulting glycans have a different degree of labeling, obtaining the two isomeric mono-antennary structures bearing 6 $^{13}C$ atoms and the trimannose glycan with 4 $^{13}C$ atoms instead of the original 8 atoms.

Figure 5:
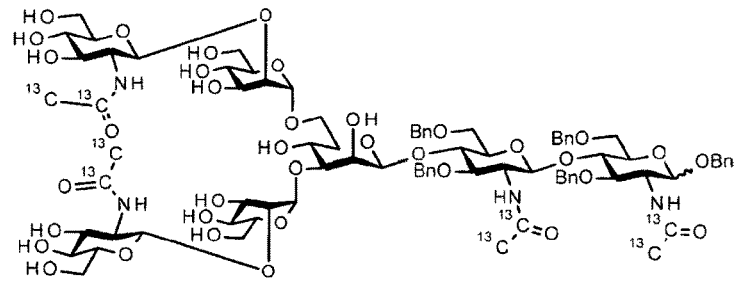
FIG. 5. Glycans obtained by chemo-enzymatic synthesis: enzymatic truncation of $^{13}C_8$-G0.
Figure 5:
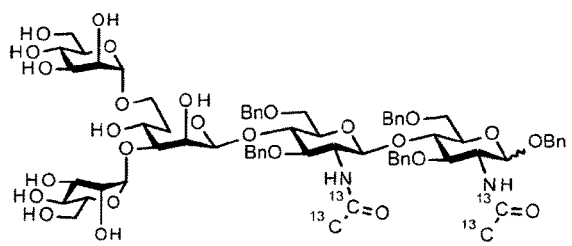
Figure 5:
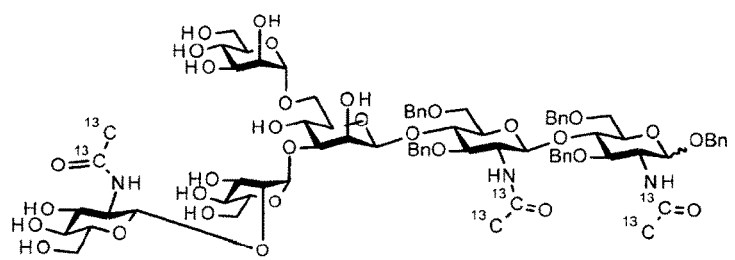
Figure 5:
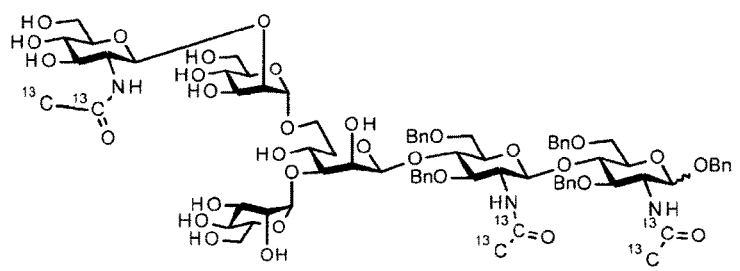
Figure 6:
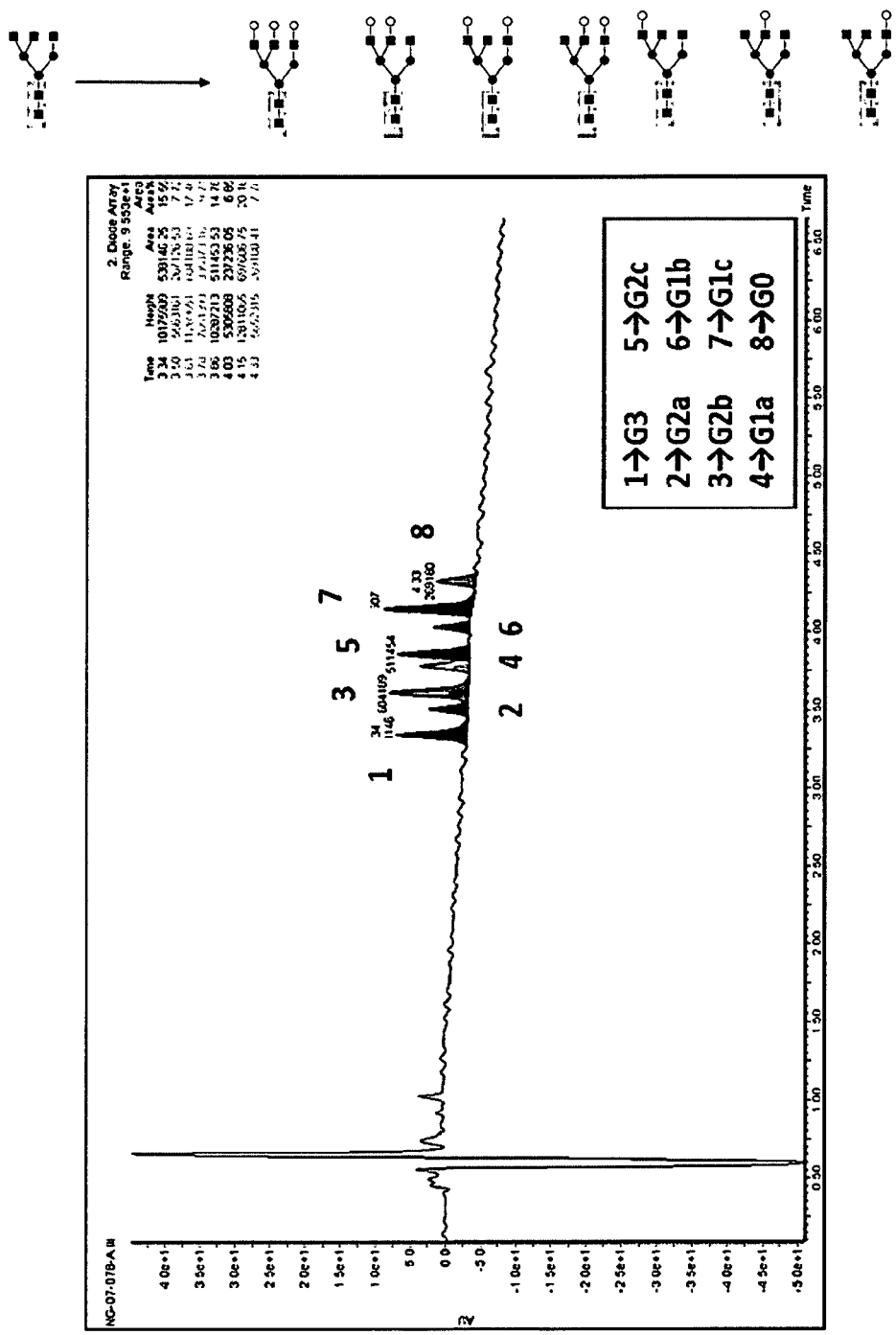
FIG. 6. Glycans obtained by chemo-enzymatic synthesis: fucosylation of $^{13}C_6$-MGn3.

The hydrolysis reaction was scaled up using 3 mg of $^{13}C_8$-G0(Bn$_5$). This mixture could be resolved by semi-preparative HPLC and the 3 new compounds were isolated in mg scale. These compounds were subjected to hydrogenolysis for the removal of the benzyl groups affording the corresponding $^{13}C$-labeled glycans $^{13}C_6$-MGn$^3$, $^{13}C_6$-MGn$^6$ and $^{13}C_4$-Man3 (FIG. 5). Also, the enzymatic fucosylation of $^{13}C_6$-MGn$^3$ yielded the standard $^{13}C_6$-MGn$^3$F quantitatively (FIG. 6).

As described previously, partially benzylated compounds can be derivatised by enzymatic reactions. This partial protection is especially useful when the corresponding reaction gives more than one product, for example, in a partial galactosylation, since this partial protection allow the separation of resultant mixtures by HPLC.

The triantennary N-glycan 22 has three different positions which can be galactosylated. A partial galactosylation produces seven new isotopically-labelled glycan standard in a single reaction: the N-glycan completely galactosylated (G3), three compounds with two galactose residues (G2a, G2b, G2c) and three compounds a single galactose residue (G1a, G1b, G1c).

Optional Oxazoline Formation

In some embodiments of the present invention, the method of synthesis further comprises the step of oxazoline formation at a free anomeric position of an acetylhexosamine unit in an oligosaccharide.

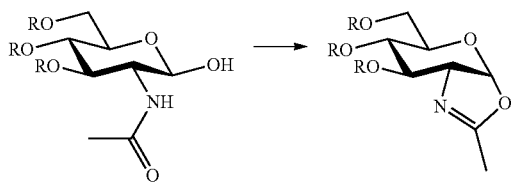

Suitable methods for this synthetic step are known in the art and include the use of coupling reagents such as CDI, DCC, EDC, and DMC; or the use of suitable Lewis acid reagents. Other dehydrating reagents or conditions may also be used, including, but not limited to, chloroformamidium-type reagents and acid combinations.

The resultant isotopically-labelled glycan oxazoline may then be used to prepare an isotopically-labelled glycoconjugate. Suitable protocols are known in the art (see, for example, Rising, 2008). Preferred glycoconjugates include glycoproteins, glycoforms, glycopeptides, peptidoglycans, glycolipids, glycosides and lipopolysaccharides.

In some embodiments, the method of synthesis involves a glycan comprising the motif [(2-acetamido-2-deoxy-β-D-glucopyranosyl-(1→2)-α-D-mannopyranosyl)-(1→6)]-(2-acetamido-2-deoxy-β-D-glucopyranosyl-(1→2)-α-D-mannopyranosyl-(1→3) -β-D-mannopyranosyl-(1→4)-2-acetamido-2-deoxy-β-D-glucopyranosyl-(1→4)-2-acetamido-2-deoxy-α,β-D-glucopyranose in which each acetyl group in the motif is isotopically-labelled. The glycan may comprise further antennary sugar units. Oxazoline formation at the free anomeric position of this glycan enables the preparation of glycoconjugate isotopologues having a fixed mass increment of at least 6 Da relative to the natural glycoconjugate. In some preferred embodiments, none of the further antennary sugar units are isotopically-labelled and the resultant isotopically-labelled glycoconjugate has a fixed mass increment of 8 Da relative to the natural glycoconjugate.

Glycan Markers in Diseases and Disorders

The biosynthesis of glycans relies on numerous highly-competitive processes involving glycosyltransferases. As a result, glycosylation is highly sensitive to the nature of the biochemical environment, and glycosylation and changes in glycosylation have been implicated in many diseases and disorders. Accordingly, in some aspects, the present invention is directed to methods for the convenient identification of so-called glycan markers (particular glycan structures known to be associated with a disease or disorder). While in some embodiments the present invention provides for the identification and quantification of a single glycan marker in a complex mixture, in other embodiments a number of glycan markers associated with one or more diseases or disorders may be identified and quantified in a single experiment.

In order to assist in the identification of signature combinations of glycan markers associated with a particular disease or disorder, in some preferred embodiments the tagged standard is a mixture comprising isotopically-labelled isotopologues of a combination, and optionally in the appropriate proportional amounts, known to be associated with a disease or disorder. In this way, pre-mixed tagged standards comprising one or more isotopically-labelled glycans may be used in methods of the invention for the determination of the presence of particular glycan signatures, and consequently in methods of diagnosis of diseases and disorders associated with those signatures.

Diseases and disorders for which suitable tagged standards comprising one or more isotopically-labelled glycans may be used include:
 cancer;
 cardiovascular disorders, for example, stroke, myocardial infarction, hypovolemic stroke, atherosclerosis;
 inflammatory skin diseases;
 diabetes mellitus;
 gastrointestinal disorders, including ulcerative colitis;
 liver disorders and diseases;
 anaemia;
 immunological diseases and disorders, for example, Wiskott-Aldrich syndrome;
 autoimmunological diseases;
 arthritis, including rheumatoid arthritis;
 infectious diseases;
 nephropathy;
 neurological disorders, including Alzheimer's disease;
 pulmonary disorders; and
 congenital disorders of glycosylation.

The above list is provided not by way of limitation and it will be understood that the methods described herein are of relevance to the detection, identification, and/or quantification of any glycan biomarker known to be associated with a disease or disorder.

It will be appreciated that the present invention provides for many useful applications in biopharmaceutical glycol-profiling. The following illustrative examples are provided to illustrate the variety of uses to which the isotopologues and methods described herein may be applied:

- Rapid identification of production batches and production sites via a quantitative singular glycan fingerprint for a given product. This could help to identify biosimilars packaged as originals and to track batch original and identity.
- Precise and quantitative detection of mAb glycans with known effector functions (influencing the binding of the Fc part to the Fc receptor) or important effects on the circulatory half-life. These include glycans with core fucose, terminal galactose, terminal sialic acid and high mannose glycans (the latter will be preferentially engage with mannose receptor of e.g. macrophages leading to the removal of the drug from circulation).
- General rapid and quantitative glycan profiling, and monosaccharide composition, degree of branching, sialylation, fucose content etc. in high-throughput applications in the biopharmaceutical industry like clone selection, process development, batch release through to IND filing.
- The particular use of fucosylated and sialylated glycans standards or any other labile glycan as internal standards in the glycan profiling by MALDI-Tof MS to quantify and monitor loss or migration of these monosaccharides and to optimize acquisition parameters to avoid the loss of these residues.
- The production of kits with the exact glycan composition of an originator therapeutic mAb or glycoproteins to guide the biosimilar producer in clone selection and process development.
- The use of internal standards for the absolute quantification of glycoforms within mixtures to aid in relating efficacy experiments to glycosylation, and in the last instance determine efficacy of a particular glycoform.

EXAMPLES

The following examples are set forth so as to provide those of ordinary skill in the art with a complete disclosure and description of how to practise the invention, and are not intended to limit the scope of the invention.

Synthesis of an N-Glycan Heptasaccharide Core

Figure 3A:
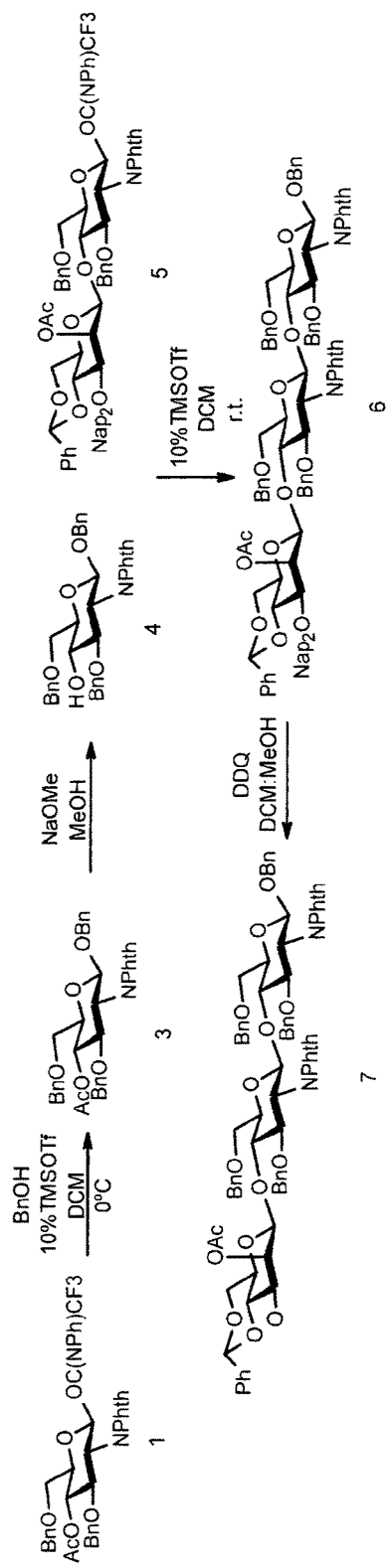
FIG. 3. The synthesis of isotopically labelled [(2-acetamido-2-deoxy-β-D-glucopyranosyl-(1→2)-α-D-mannopyranosyl)-(1→6)]-[2-acetamido-2-deoxy-β-D-glucopyranosyl-(1→2)-α-D-mannopyranosyl-(1→3)]-β-D-mannopyranosyl-(1→4)-2-acetamido-2-deoxy-β-D-glucopyranosyl-(1→4)-2-acetamido-2-deoxy-α,β-D-glucopyranose, wherein each acetyl group is $^{13}C_2$-isotopically-labelled.
Figure 3B:
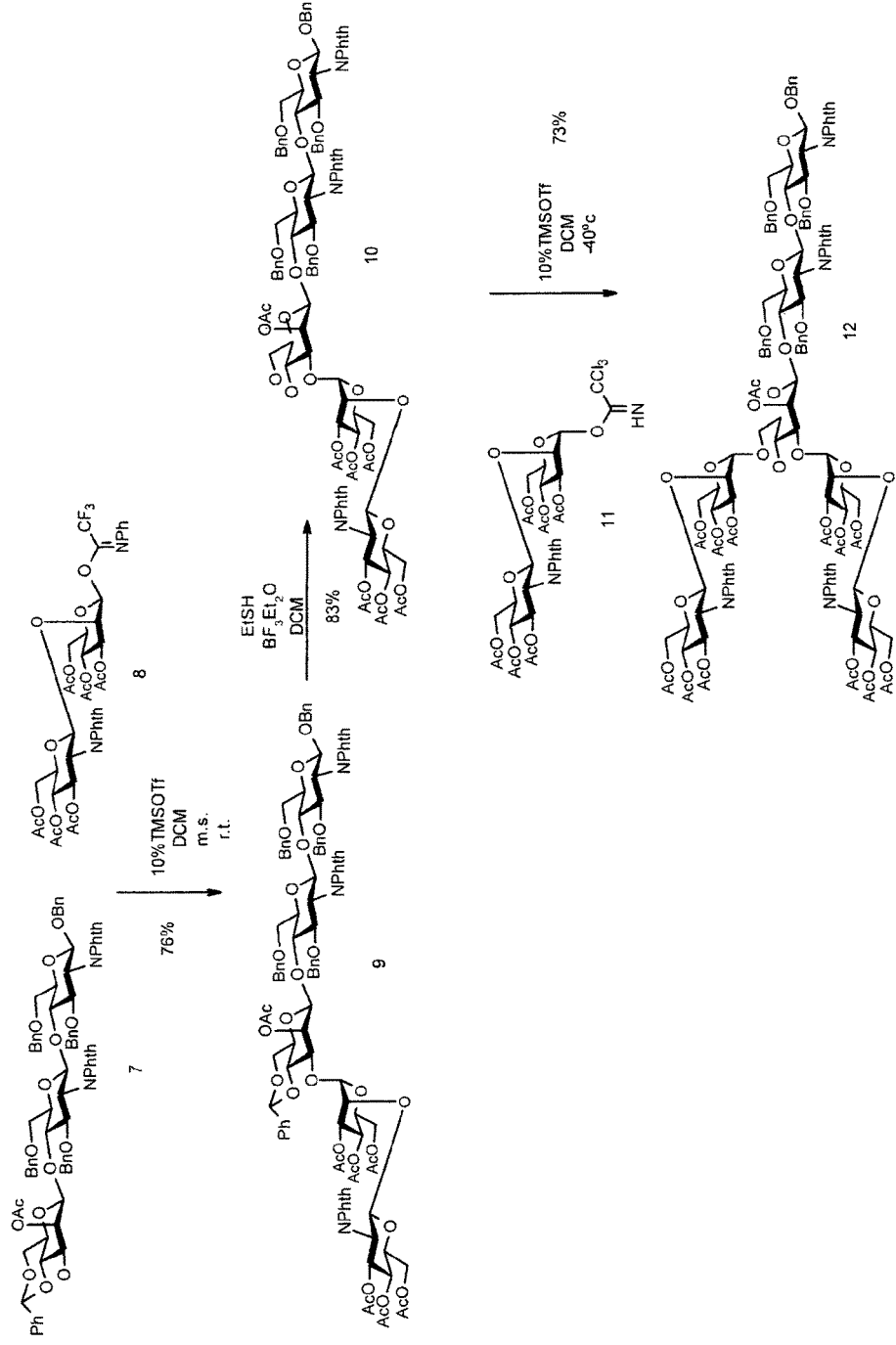
Figure 3C:
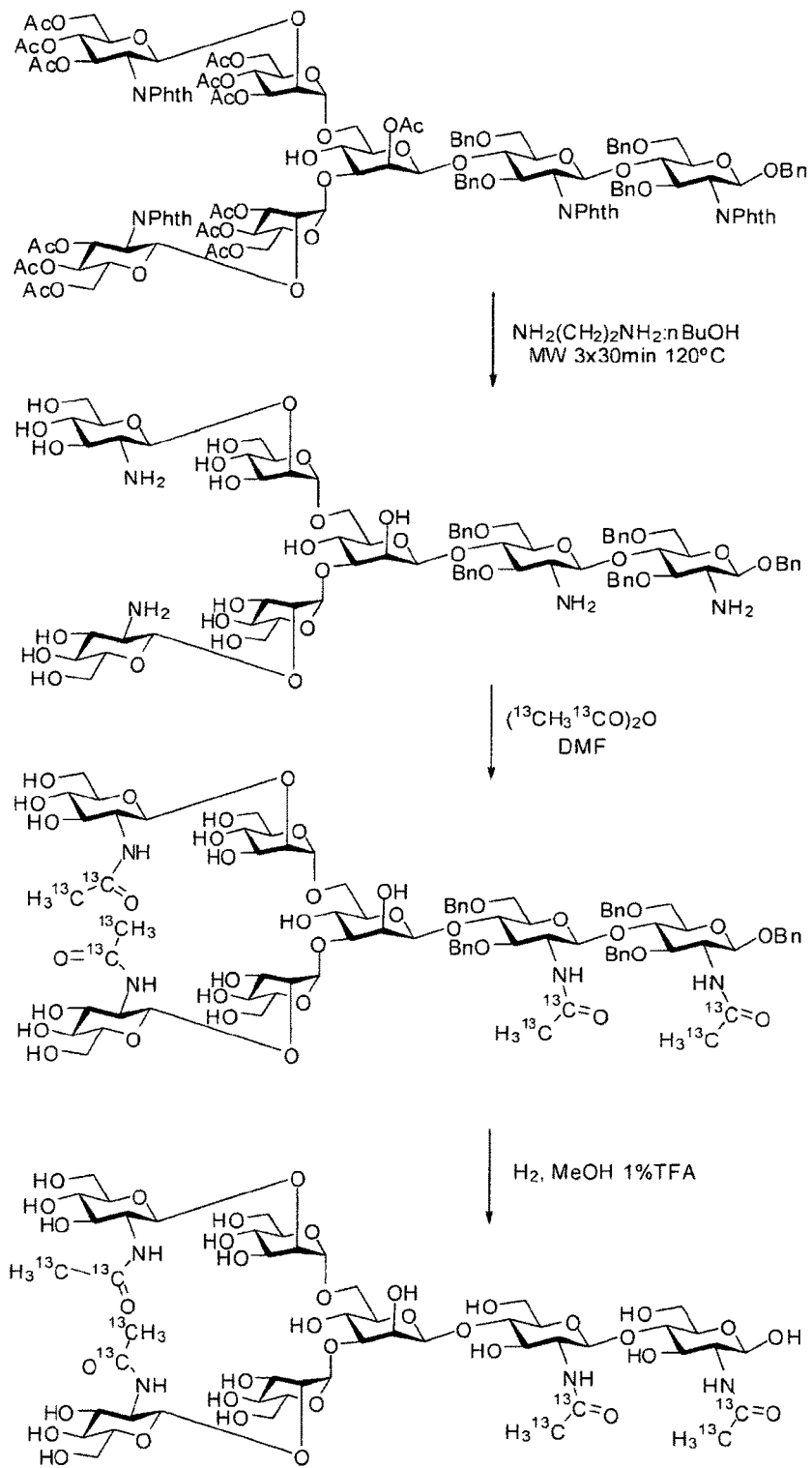

The following synthesis is numbered with respect to the corresponding chemicals structures shown in FIG. 3.

Benzyl 4-O-acetyl-3,6-di-O-benzyl-2-deoxy-2-phthalimido-β-D-glucopyranoside (2)

A solution of benzyl alcohol (54 µL, 0.525 mmol, 1.5 eq) and 1 (250 mg, 0.350 mmol, synthesized according to Serna S., Kardak B., Reichardt N., Martin-Lomas M., *Tetrahedron Asymmetry*, 2009, 20, 851-856) with molecular sieves in dry DCM was stirred for 45 min at room temperature. The mixture was cooled to 0° C. and TMSOTf (6 µL, 0.035 mmol, 0.1 eq) is added. After 1 h, the reaction was quenched with triethylamine, filtered through a plug of celite and concentrated. The crude residue was purified by flash chromatography hexane:EtOAc 9:1 to give the title compound (198 mg, 90%).

Rf 0.39 (toluene:EtOAc 9:1); $[\alpha]_D^{20}$=+9.2 (c=0.5, CHCl$_3$); $^1$HNMR (500 MHz, CDCl$_3$) δ 7.87-7.48 (m, 4H, Phth), 7.40-7.27 (m, 5H, Ph), 7.13-6.96 (m, 7H, Ph), 6.95-6.85 (m, 3H, Ph), 5.19-5.09 (m, 2H, H-1, H-4), 4.81 (d, J=12.3 Hz, 1H, CH$_2$ Bn), 4.61-4.54 (m, 3H, CH$_2$ Bn), 4.50 (d, J=12.4 Hz, 1H, CH$_2$ Bn), 4.42 (dd, J=10.7, 8.9 Hz, 1H, H-3), 4.34-4.27 (m, 2H, H-2, CH$_2$ Bn), 3.75 (dt, J=9.7, 4.6 Hz, 1H, H-5), 3.68-3.60 (m, 2H, h-6), 1.94 (s, 3H, CH$_3$ Ac); $^{13}$C NMR (CDCl$_3$) δ:169.8, 138.1, 137.9, 137.1, 133.9, 131.7, 128.5, 128.3, 128.2, 128.0, 127.9, 127.8, 127.8, 127.8, 127.5, 123.4, 123.4, 97.3(C-1), 73.9, 73.8, 73.6, 72.6, 71.0, 69.9, 55.6, 21.0; HRMS (ESI): m/z: calcd C$_{37}$H$_{35}$NO$_6$Na: 644.2260 (M+Na)$^+$, found 644.2294.

Benzyl 3,6-di-O-benzyl-2-deoxy-2-phthalimido-β-D-glucopyranoside (3)

To a solution of 2 (608 mg, 0.978 mmol) in MeOH:CH$_2$Cl$_2$ 2:1 (6 mL) NaOMe 0.25 M was added (300 µL, 20%). After stirring for 1 h, acidic ion exchange resin was added until pH 7. The solution was filtered, concentrated and purified by flash chromatography to give the title compound (430 mg, 76%).

Rf (hexane:EtOAc); $[\alpha]_D^{20}$=+9.4 (c=0.5, CHCl$_3$); $^1$H NMR (500 MHz, CDCl$_3$) δ 7.89-7.50 (m, 4H, Phth), 7.42-7.29 (m, 5H, Ph), 7.13-7.01 (m, 7H, Ph), 6.98-6.89 (m, 3H, Ph), 5.20-5.12 (m, 1H, H-1), 4.79 (d, J=12.3 Hz, 1H, CH$_2$ Bn), 4.73 (d, J=12.2 Hz, 1H, CH$_2$ Bn), 4.67 (d, J=11.9 Hz, 1H, CH$_2$ Bn), 4.61 (d, J=12.0 Hz, 1H, CH$_2$ Bn), 4.52 (d, J=12.3 Hz, 1H, CH$_2$ Bn), 4.48 (d, J=12.3 Hz, 1H, CH$_2$ Bn), 4.29-4.19 (m, 2H, H-2, H-3), 3.90-3.78 (m, 3H, H-6, H-6, H-4), 3.65 (dt, J=9.7, 4.9 Hz, 1H, H-5), 2.96 (br s, 1H, OH); $^{13}$C NMR (CDCl$_3$) δ:168.1, 167.8, 138.3, 137.8, 137.2, 133.8, 131.7, 128.6, 128.2, 128.0, 128.0, 127.9, 127.7, 127.7, 127.5, 123.4, 123.3, 97.5(C-1), 78.7, 74.4, 73.9, 73.7, 70.9, 70.8, 55.5; HRMS (ESI): m/z: calcd C$_{35}$H$_{33}$NO$_7$Na: 602.2155 [M+Na]$^+$, found 602.2128.

Benzyl 2-O-acetyl-4,6-O-benzylidene-3-O-(2-naphthylmethyl)-β-D-mannopyranosyl-(1→4)-3,6-di-O-benzyl-2-deoxy-2-phthalimido-β-D-glucopyranosyl-(1→4)-3,6-di-O-benzyl-2-deoxy-2-phthalimido-β-D-glucopyranoside (5)

A solution of 1 (400 mg, 0.69 mmol) and 4 (905 mg, 0.83 mmol, 1.2 eq, synthesized according to Serna S., Kardak B., Reichardt N., Martin-Lomas M., *Tetrahedron Asymmetry*, 2009, 20, 851-856) in dry CH$_2$Cl$_2$ with 3A molecular sieves was stirred for 1 h at room temperature. To this mixture TMSOTf (12 µL, 0.07 mmol, 10%) was added at room temperature and the reaction stirred until TLC showed complete conversion of the starting material (1h). The reaction was quenched by adding triethylamine (20 µL), filtered through a plug of celite and concentrated. The crude residue was purified by flash chromatography to obtain the title compound (750 mg, 73%).

Rf 0.17 (hexane:EtOAc 3:1); $[\alpha]_D^{20}$=−4.9 (c=0.5, CHCl$_3$); $^1$H NMR (500 MHz, CDCl$_3$) δ 7.91-7.58 (m, 10H), 7.57-7.28 (m, 12H), 7.23-7.13 (m, 4H), 7.12-6.87 (m, 13H), 6.81-6.68 (m, 3H), 5.53 (s, 1H, CHPh), 5.51 (dd, J=3.3, 1.3 Hz, 1H, H-2C), 5.27 (d, J=8.3 Hz, 1H, H-1B), 4.95 (d, J=8.4 Hz, 1H, H-1A), 4.88 (d, J=12.1 Hz, 1H, CH$_2$ Bn), 4.83 (d, J=12.8 Hz, 2H, 2×CH$_2$ Bn), 4.7-4.67 (m, 3H, 2×CH$_2$ Bn, H-1C), 4.57-4.47 (m, 4H, 2×CH$_2$ Bn), 4.42 (d, J=12.1 Hz, 1H, 1×CH$_2$ Bn), 4.40-4.35 (m, 2H, 2×CH$_2$ Bn), 4.29 (dd, J=10.7, 8.5 Hz, 1H, H-3B), 4.25-4.08 (m, 6H, H2A, H2B, H-4A, H-4B, H-3A, H-6Ca), 3.90 (t, J=9.6 Hz, 1H, H-4C), 3.68-3.59 (m, 2H, H-6Ba, H-6Bb), 3.59-3.50 (m, 3H, H-6Cb, H-6Aa, H-3C), 3.43 (dd, J=11.1, 3.8 Hz, 1H, H-6Ab), 3.30 (ddd, J=9.9, 3.9, 1.7 Hz, 1H, H-5A), 3.23 (dt, J=9.9, 2.2 Hz, 1H, H-5B), 3.13 (td, J=9.7, 4.9 Hz, 1H, H-5C), 2.22 (s, 3H, CH₃ Ac); ¹³C NMR (CDCl₃) δ:170.3, 168.6, 167.7, 167.6, 138.7, 138.7, 138.5, 137.9, 137.6, 137.3, 135.4, 134.1, 133.9, 133.5, 133.4, 133.1, 131.9, 131.8, 131.5, 129.1, 128.6, 128.4, 128.3, 128.2, 128.1, 128.1, 127.9, 127.8, 127.7, 127.7, 127.6, 127.6, 127.5, 127.3, 126.9, 126.3, 126.1, 126.0, 125.5, 123.8, 123.2, 101.7, 99.4(C-1C), 97.2(C-1A), 97.1(C-1B), 79.0, 77.9, 77.0, 76.6, 75.9, 75.8, 74.7, 74.6, 74.4, 74.3, 73.2, 72.9, 71.6, 70.6, 69.2, 68.5, 68.3, 67.9, 67.0, 56.6, 55.8, 21.2; HRMS (ESI): m/z: calcd C₈₉H₈₂N₂O₁₉Na: 1506.5443 [M+Na]⁺, found 1506.5481.

Benzyl 2-O-acetyl-4,6-O-benzylidene-β-D-mannopyranosyl-(1→4)-3,6-di-O-benzyl-2-deoxy-2-phthalimido-β-D-glucopyranosyl-(1→4)-3,6-di-O-benzyl-2-deoxy-2-phthalimido-β-D-glucopyranoside (6)

To a solution of 5 (300 mg, 0.202 mmol) in CH₂Cl₂:MeOH 4:1 (1→2 mL), DDQ (138 mg, 0.606 mmol, 3 eq) was added. After 2h, the mixture was diluted with EtOAc and washed with saturated NaHCO₃, water and brine. The solution was concentrated and purified by flash chromatography to give the title compound (176 mg, 65%).

Rf 0.37 (hexane:EtOAc 3:2); [α]$_D^{20}$=−4.6 (c=1, CHCl₃); ¹HNMR (500 MHz, CDCl₃) δ 7.94-7.57 (m, 8H, Phth), 7.50-7.27 (m, 15H, Ph), 7.11-6.88 (m, 12H, Ph), 6.82-6.68 (m, 3H, Ph), 5.47 (s, 1H, CHPh), 5.31 (dd, J=3.1, 1.2 Hz, 1H, H-2C), 5.26 (d, J=8.2 Hz, 1H, H-1B), 4.95 (d, J=8.4 Hz, 1H, H-1A), 4.85 (t, J=12.4 Hz, 2H, CH₂Ph), 4.76 (d, J=1.3 Hz, 1H, H-1C), 4.70 (d, J=12.4 Hz, 1H, CH₂Ph anomeric), 4.62 (d, J=12.0 Hz, 1H, CH₂Ph), 4.50 (d, J=13.3 Hz, 3H, CH₂Ph), 4.47 (d, J=12.0 Hz, 1H, CH₂Ph), 4.41 (d, J=12.1 Hz, 1H, CH₂Ph anomeric), 4.37 (d, J=12.4 Hz, 1H, CH₂Ph), 4.30-4.23 (m, 1H, H-3B), 4.23-4.08 (m, 6H, H-2B, H-4A, H-2A, H-4B, H-3A, H-6Ca), 3.75-3.67 (m, 2H, H-4C, H-3C), 3.63 (dd, J=7.2, 2.3 Hz, 2H, H-6Ba, H-ABb), 3.59-3.50 (m, 2H, H-6Cb, H-6Aa), 3.43 (dd, J=11.1, 3.8 Hz, 1H, H-6Ab), 3.33-3.27 (m, 1H, H-5A), 3.23-3.18 (m, 1H, H-5B), 3.15 (dd, J=15.0, 8.2 Hz, 1H, H-5C), 2.20 (s, 3H, CH₃ Ac); ¹³C NMR (CDCl₃) δ:170.6, 168.5, 167.7, 138.7, 138.4, 138.0, 137.3, 137.1, 134.1, 133.9, 133.5, 131.8, 131.5, 129.3, 128.6, 128.4, 128.4, 128.1, 128.1, 127.9, 127.9, 127.7, 127.6, 127.5, 127.3, 126.9, 126.3, 123.7, 123.2, 102.1, 99.3(C-1C), 97.2(C-1A), 97.0(C-1B), 79.1, 78.6, 76.6, 75.7, 74.6, 74.4, 74.4, 73.3, 72.9, 71.4, 70.5, 69.9, 68.5, 68.3, 67.8, 66.7, 56.6, 55.8, 21.1; HRMS (ESI): m/z: calcd C₇₈H₇₄N₂O₁₉Na: 1365.4784 [M+Na]⁺, found 1365.4840.

Benzyl (3,4,6-tri-O-acetyl-2-deoxy-2-phthalimido-β-D-glucopyranosyl-(1→2)-3,4,6-tri-O-acetyl-α-D-mannopyranosyl)-(1→3)-2-O-acetyl-4,6-O-benzylidene-β-D-mannopyranosyl-(1→4)-3,6-di-O-benzyl-2-deoxy-2-phthalimido-β-D-glucopyranosyl-(1→4)-3,6-di-O-benzyl-2-deoxy-2-phthalimido-β-D-glucopyranoside (8)

A solution of 6 (100 mg, 0.074 mmol) and 7 (80 mg, 0.089 mmol, 1.2 eq, synthesized according to Unverzagt, C.; Eller, S.; Mezzato, S.; Schuberth, R. *Chem. Eur. J.* 2007, 14, 1304-1311) in dry CH₂Cl₂ with molecular sieves was stirred at room temperature for 1 h. To this mixture, TMSOTf (1.6 μL, 0.007 mmol, 10%) was added and stirred until TLC showed complete conversion of the starting material (1h). The reaction was quenched by the addition triethylamine (20 μL), filtered through a plug of celite and the filtrate concentrated. The crude residue was purified by flash chromatography to give the title compound (116 mg, 76%).

Rf 0.13 (hexane:EtOAc 1:1); [α]$_D^{20}$=−15.8 (c=0.5, CHCl₃); ¹ NMR (500 MHz, CDCl₃) δ 7.95-7.51 (m, 16H), 7.51-7.27 (m, 11H), 7.08-6.89 (m, 12H), 6.84-6.68 (m, 3H), 5.48-5.40 (m, 2H, H-3E, CHPh), 5.23 (d, J=7.9 Hz, 1H, H-1B), 5.16 (d, J=4.0 Hz, 1H, H-2C), 5.02 (t, J=10.2 Hz, 1H, H-4D), 4.99-4.89 (m, 3H, H-4D, H-1A, H-1D), 4.89-4.77 (m, 4H, H-1E, 2×CH₂Ph, H-3D), 4.68 (d, J=12.2 Hz, 2H, CH₂Ph anomeric, CH₂Ph), 4.54-4.46 (m, 4H, 3×CH₂Ph, H-1C), 4.41-4.30 (m, 3H, CH₂Ph anomeric, 2×CH₂Ph), 4.28-4.05 (m, 8H, H-2E, H-3B, H-4A, H-2B, H-2A, H-3A, H-4B, H-6Ca), 4.00 (dd, J=3.0, 1.7 Hz, 1H, H-2D), 3.93 (dd, J=12.3, 3.3 Hz, 1H, H-6Ea), 3.83 (dt, J=9.8, 3.7 Hz, 1H, H-5D), 3.73 (t, J=9.6 Hz, 1H, H-4C), 3.70-3.62 (m, 4H, H-6Eb, H-6 Da, H-6Db, H-6Ba), 3.60-3.51 (m, 3H, H-6Bb, H-6Aa, H-3C), 3.48 (t, J=10.3 Hz, 1H, H-6Cb), 3.38 (dd, J=11.1, 3.6 Hz, 1H, H-6Ab), 3.29 (dd, J=9.8, 3.1 Hz, 1H, H-5A), 3.15 (dd, J=9.9, 2.1 Hz, 1H, H-5B), 3.00 (td, J=9.7, 5.0 Hz, 1H, H-5C), 2.15 (s, 4H, CH₃ Ac, H-5E), 2.05 (d, J=5.8 Hz, 6H, CH₃ Ac), 1.99 (d, J=11.5 Hz, 5H, CH₃ Ac), 1.86 (d, J=4.8 Hz, 6H, CH₃ Ac); ¹³C NMR (CDCl₃) δ:170.6, 170.6, 170.5, 170.2, 170.1, 169.5, 169.2, 167.7, 167.6, 138.8, 138.7, 138.5, 137.9, 137.4, 137.3, 134.3, 134.1, 133.9, 133.5, 131.8, 131.8, 131.5, 130.2, 129.0, 128.8, 128.6, 128.3, 128.1, 128.1, 127.9, 127.7, 127.6, 127.6, 127.6, 127.3, 127.0, 126.9, 123.8, 123.7, 123.2, 102.4, 98.5 (C-1C), 98.0 (C-1D), 97.2 (C-1A, C-1B), 95.8 (C-1E), 78.8, 78.3, 76.7, 76.5, 75.9, 75.3, 74.6, 74.5, 74.4, 74.3, 73.5, 72.9, 71.2, 70.6, 70.6, 70.5, 69.4, 68.9, 68.6, 68.5, 68.3, 67.5, 66.2, 65.5, 62.9, 61.1, 56.6, 55.8, 54.1, 20.9, 20.7, 20.6, 20.6; HRMS (ESI): m/z: calcd C₁₁₀H₁₀₉N₃O₃₆Na: 2070.6689 [M+Na]⁺, found 2070.6689.

Benzyl (3,4,6-tri-O-acetyl-2-deoxy-2-phthalimido-β-D-glucopyranosyl-(1→2)-3,4,6-tri-O-acetyl-α-D-mannopyranosyl)-(1→3)2-O-acetyl-β-D-mannopyranosyl-(1→4)-3,6-di-O-benzyl-2-deoxy-2-phthalimido-β-D-glucopyranosyl-(1→4)-3,6-di-O-benzyl-2-deoxy-2-phthalimido-β-D-glucopyranoside (9)

To a solution of 8 (100 mg, 0.046 mmol) in CH₂Cl₂ (1 mL) at 0° C., ethanethiol (17 μL, 0.244 mmol, 5 eq) and borontrifluoride diethyletherate (1 μL, 20%) were added. After 2h, triethylamine is added. The mixture was concentrated and purified by flash chromatography (hexane:EtOAc, 3:1) to give the title compound (75 mg, 83%).

Rf 0.1 (hexane:EtOAc 1:2); [α]$_D^{20}$=−3.9 (c=0.5, CHCl₃); NMR (500 MHz, CDCl₃) δ 7.94-7.41 (m, 12H, Phth), 7.35-7.22 (m, 10H, Phth, Ph), 7.16 (m, 1H, Ph), 7.07-6.93 (m, 12H, Ph), 6.74 (m, 3H, Ph), 5.72 (dd, J=10.7, 9.1 Hz, 1H, H-3E), 5.36 (d, J=8.5 Hz, 1H, H-1E), 5.25 (d, J=8.1 Hz, 1H, H-1B), 5.18-5.10 (m, 3H, H-4D, H-4E, H-2C), 4.96-4.91 (m, 2H, H-1D, H-1A), 4.91-4.81 (m, 3H, 2×CH₂ Bn, H-3D), 4.68 (d, J=12.4 Hz, 1H, CH₂Ph), 4.60 (d, J=12.1 Hz, 1H, CH₂Ph), 4.54 (s, 1H, H-1D), 4.53-4.46 (m, 3H, 3×CH₂ Bn), 4.43-4.34 (m, 4H, 3×CH₂ Bn, H-2E), 4.29 (dd, J=12.3, 4.8 Hz, 1H, H-6E), 4.27-4.13 (m, 5H, H-2B, H-3B, H-4A, H-2D, H-2A), 4.13-4.06 (m, 3H, H-6E, H-3A, H-4B), 3.85-3.77 (m, 4H, H-5E, H-5D, H-6 Da, H-6Db), 3.75 (t, J=9.5 Hz, 1H, H-4C), 3.68 (dd, J=11.8, 3.4 Hz, 1H, H-6Ca), 3.62 (dd, J=11.6, 1.7 Hz, 1H, H-6Ba), 3.57-3.50 (m, 3H, H-6Aa, H-6Bb, H-6Cb), 3.42 (dd, J=11.1, 3.8 Hz, 1H, H-6Ab), 3.34 (dd, J=9.4, 3.5 Hz, 1H, H-3C), 3.31-3.26 (m, 1H, H-5A), 3.22-3.16 (m, 1H, H-5B), 2.98 (dt, J=8.9, 4.1 Hz, 1H, H-5C), 2.11 (2×s, J=1.3 Hz, 6H, 2×CH₃ Ac), 2.06-2.00 (3×s, 9H, 3×CH₃ Ac), 1.98 (s, 3H, CH₃ Ac), 1.86 (s, 3H, CH₃ Ac); $^{13}$C NMR (CDCl₃) δ:170.9, 170.8, 170.7, 170.3, 170.2, 169.5, 169.5, 168.6, 167.7, 138.7, 138.5, 138.4, 137.8, 137.3, 134.5, 133.5, 131.8, 131.4, 128.7, 128.4, 128.3, 128.2, 128.2, 128.1, 127.9, 127.6, 127.6, 127.5, 127.4, 126.9, 123.8, 123.7, 123.3, 123.2, 98.4(C-1D), 97.7(C-1C), 97.2 (C-1E), 97.2(C-1A), 97.1(C-1B), 77.6, 77.5, 76.7, 75.4, 74.6, 74.6, 74.5, 74.5, 74.4, 73.4, 72.9, 72.0, 70.7, 70.6, 70.5, 69.9, 69.1, 69.0, 68.5, 68.2, 65.5, 62.5, 62.1, 62.1, 56.5, 55.8, 54.4, 21.0, 20.9, 20.8, 20.7, 20.7, 20.5; HRMS (ESI): m/z: calcd C₁₀₃H₁₀₅N₃O₃₆Na: 1982.6376 [M+Na]⁺, found 1982.6331.

Benzyl [(3,4,6-tri-O-acetyl-2-deoxy-2phthalimido-β-D-glucopyranosyl-(1→2)-3,4,6-tri-O-acetyl-α-D-mannopyranosyl)-(1→6)]-[(3,4,6-tri-O-acetyl-2-deoxy-2phthalimido-β-D-glucopyranosyl-(1→2)-3,4,6-tri-O-acetyl-α-D-mannopyranosyl)-(1→3)]-2-O-acetyl-β-D-mannopyranosyl-(1→4)-3,6-di-O-benzyl-2-deoxy-2-phthalimido-β-D-glucopyranosyl-(1→4)-3,6-di-O-benzyl-2-deoxy-2-phthalimido-β-D-glucopyranoside (11)

A solution of 9 (45 mg, 0.023 mmol) and 10 (30 mg, 0.034 mmol, 1.2 eq, synthesized according to Unverzagt, C.; Eller, S.; Mezzato, S.; Schuberth, R. *Chem. Eur. J.* 2007, 14, 1304-1311) in dry CH₂Cl₂ (6 mL) with molecular sieves was stirred at room temperature for 1 h. This mixture was cooled to −40° C., TMSOTf (1 μL, 0.007 mmol, 25%) was added and the reaction stirred at this temperature until TLC showed complete conversion of the starting material (1h). The reaction was quenched by adding triethylamine (5 μL), filtered through a plug of celite and concentrated. The crude residue was purified by flash chromatography and preparative plate gave the title compound (45 mg, 74%).

Rf 0.28 (hexane:acetone 1:1); $[α]_D^{20}$=−2.8 (c=0.5, CHCl₃); $^{1}$H NMR (500 MHz, CDCl₃) δ 7.88-7.55 (m, 15H, Phth), 7.40 (m, J=7.1 Hz, 1H Phth), 7.33-7.20 (m, 9H, Ph), 7.14 (m, J=5.3, 2.8 Hz, 1H, Ph), 7.06-6.97 (m, 3H, Ph), 6.98-6.88 (m, 6H, Ph), 6.84 (m, J=7.3 Hz, 2H, Ph), 6.81-6.67 (m, 4H, Ph), 5.69 (dd, J=10.8, 9.1 Hz, 1H, H-1E), 5.61 (dd, J=10.8, 9.2 Hz, 1H, H-1E'), 5.40 (d, J=8.5 Hz, 1H, H-1E), 5.22-5.14 (m, 4H, H-4D, H-4E, H-1B, H-1E'), 5.14-5.05 (m, 3H, H-4D', H-2C, H-4E'), 4.94 (dd, J=10.2, 3.4 Hz, 1H, H-3D'), 4.90-4.86 (m, 2H, H-1D, H-1A), 4.83 (dd, J=10.2, 3.2 Hz, 1H, H-3D), 4.78 (d, J=12.9 Hz, 1H, CH₂ Bn), 4.72 (d, J=12.7 Hz, 1H, CH₂ Bn), 4.68-4.60 (m, 2H, CH₂ Bn), 4.53 (s, 1H, H-1C), 4.52-4.36 (m, 7H, 5×CH₂ Bn, H-2E, H-1D'), 4.36-4.25 (m, 4H, H-2E',H-6aE CH₂ Bn anomeric, H-4D), 4.23-4.14 (m, 3H, H-3B, H-4A, H-6aE'), 4.14-4.00 (m, 6H, H-2A, H-2B, H-2D', H-3A, H-4B, H-6bE), 3.90-3.83 (m, 2H, H-5E, H-6aD), 3.84-3.70 (m, 7H, H-6bE', H-4C, H-5D, H-6bD, H-6aD', H-6bD', H-6aC), 3.67 (d, J=9.9 Hz, 1H, H-5D), 3.62-3.45 (m, 3H, H-6aB, H-6bB, H-6aA), 3.36-3.27 (m, 4H, H-6BA, H-6BC, H-3C, H-5E'), 3.24 (d, J=8.0 Hz, 1H, H-5A), 3.15 (d, J 9.3 Hz, 1H, H-5B), 3.10 (dt, J=8.4, 3.9 Hz, 1H, H-5C), 2.13 (s, 3H, CH₃ Ac), 2.09 (s, 3H, CH₃ Ac), 2.02 (3×s, 9H, 3×CH₃ Ac), 2.01-1.97 (m, 15H, 5×CH₃ Ac), 1.93 (s, 3H, CH₃ Ac), 1.85 (d, J=2.3 Hz, 6H, CH₃ Ac); $^{13}$C NMR (CDCl₃) δ:171.0, 170.9, 170.8, 170.8, 170.7, 170.4, 170.3, 170.2, 169.5, 169.4, 168.3, 167.7, 167.5, 138.8, 138.7, 138.4, 138.0, 137.2, 134.5, 134.1, 133.8, 133.5, 131.8, 131.7, 131.5, 131.4, 128.7, 128.3, 128.2, 128.1, 128.1, 128.0, 127.9, 127.6, 127.5, 127.3, 126.9, 123.7, 123.7, 123.6, 123.2, 99.0(C-1D), 98.1 (C-1C), 97.8(C-1D'), 97.2(C-1E), 97.2, 97.1, 97.0, (C-1A, C-1B, C-1E') 78.2, 78.1, 76.7, 75.8, 74.5, 74.4, 74.4, 74.3, 73.3, 73.2, 72.8, 71.8, 71.7, 70.7, 70.6, 70.5, 70.4, 70.0, 69.3, 69.1, 68.9, 68.5, 68.1, 68.1, 67.3, 65.7, 65.4, 62.5, 62.4, 61.8, 61.6, 56.5, 55.7, 54.5, 20.9, 20.9, 20.8, 20.7, 20.7, 20.5; HRMS (ESI): m/z: calcd C₁₃₅H₁₄₀N₄O₅₃Na: 2687.8275 [M+Na]⁺, found 2687.8379.

Benzyl [(2-amino-2-deoxy-β-D-glucopyranosyl-(1→2)-α-D-mannopyranosyl)-(1→6)]-(2-amino-2-deoxy-β-D-glucopyranosyl-(1→2)-α-D-mannopyranosyl-(1→3))-β-D-mannopyranosyl-(1→4)-2-amino-3,6-di-O-benzyl-2-deoxy-β-D-glucopyranosyl-(1→4)-2-amino-3,6-di-O-benzyl-2-deoxy-β-D-glucopyranoside (12)

To a solution of heptasaccharide 11 (32 mg, 12 μmol) in MeOH:CH₂Cl₂ 2:1, NaOMe (30 μL, 0.5M, 1.25 eq) was added. After stirring 1h at room temperature, MeOH (400 μL) and ethylenediamine (300 μL) were added and the mixture heated for 3 cycles of 30 min at 120° C. in a microwave. The mixture was concentrated to dryness using toluene and ethanol. The crude residue was purified by Sephadex LH-2 column (MeOH:DCM 2:1) to give the titled compound (17 mg, 83%).

$^{1}$H NMR (500 MHz, MeOD) δ 7.52 (d, J=7.1 Hz, 2H, Ph), 7.46-7.25 (m, 21H, Ph), 7.21 (dd, J=4.7, 2.0 Hz, 2H, Ph), 5.22 (dd, J=6.8, 4.8 Hz, 2H, CH₂Bn, H-1 Man), 5.17 (d, J=11.5 Hz, 1H, CH₂Bn), 4.98 (d, J=1.9 Hz, 1H, H-1 Man), 4.70-4.56 (m, 5H, 4 CH₂Bn, H-1 Man), 4.50 (s, 2H, CH₂Bn), 4.47 (d, J=8.2 Hz, 1H, H-1 GlcN), 4.43 (d, J=7.8 Hz, 1H, H-1 GlcN), 4.39 (d, J=7.9 Hz, 1H, H-1 GlcN), 4.30 (d, J=8.1 Hz, 1H, H-1 GlcN), 4.25-4.12 (m, 3H), 4.08 (t, J=9.2 Hz, 1H, H-4 GlcN), 4.02-3.96 (m, 1H, H-6 Glc), 3.96-3.76 (m, 12H), 3.76-3.61 (m, 10H), 3.58 (m, 2H), 3.52 (m, 1H), 3.48-3.42 (m, 1H), 3.41-3.32 (m, 5H), 3.31-3.19 (m, 4H), 2.83 (td, J=10.7, 8.1 Hz, 2H, H-2 GlcN), 2.77 (d, J=8.4 Hz, 1H, H-2, GlcN), 2.67 (dd, J=9.7, 8.0 Hz, 1H, H-2 GlcN); $^{13}$C NMR from HSQC experiment (126 MHz, MeOD) δ 128.48, 127.90, 127.93, 127.38, 127.89, 100.48, 74.34, 74.41, 97.67, 70.66, 74.24, 72.70, 99.85, 70.73, 74.33, 72.71, 72.90, 101.50, 101.71, 101.96, 101.48, 77.11, 74.70, 70.40, 76.35, 77.63, 70.20, 66.17, 61.22, 73.63, 70.36, 66.15, 68.17, 61.02, 68.29, 66.25, 60.84, 67.52, 72.89, 68.48, 75.01, 82.05, 82.63, 82.33, 76.99, 70.04, 75.54, 75.27, 76.85, 56.82, 56.18, 56.16, 56.22.

Benzyl [(2-acetamido-2-deoxy-β-D-glucopyranosyl-(1→2)-α-D-mannopyranosyl)-(1→6)]-[2-acetamido-2-deoxy-β-D-glucopyranosyl-(1→2)-α-D-mannopyranosyl-(1→3)]-β-D-mannopyranosyl-(1→4)-2-acetamido-3,6-di-O-benzyl-2-deoxy-β-D-glucopyranosyl-(1→4)-2-acetamido-3,6-di-O-benzyl-2-deoxy-β-D-glucopyranoside ($^{13}$C₈) 13 ($^{13}$C₈-G0(Bn₅))

To a solution of heptasaccharide 12 (100 mg, 62.5 μmol) in dry MeOH (2 mL) at 0° C., acetic anhydride $^{13}$C₄ (42 μL, 444 μmol) and NaOMe 0.5M (0.8 mL) were added. After 2 h at 0° C. the mixture was concentrated and purified by HPLC Sepadex LH-20 (MeOH) to give the titled compound (80 mg, 72%). $^{1}$H NMR (500 MHz, MeOD) δ 7.40-7.21 (m, 22H, arom), 7.21-7.14 (m, 3H, arom), 5.07 (d, J=1.9 Hz, 1H, H-1D), 4.99 (dd, J=16.3, 12.0 Hz, 2H, 2 CH₂Bn), 4.82 (d, J=12.5 Hz, 1H, CH₂Bn), 4.79 (d, J=1.8 Hz, 1H, H-1D'), 4.75 (d, J=12.1 Hz, 1H, CH₂Bn), 4.70-4.66 (m, 2H, H-1C, H-1B), 4.66-4.54 (m, 4H, CH₂Bn), 4.46 (dd, J=13.9, 8.2 Hz, 4H, H-1A, H-1E, 2 CH₂Bn), 4.31 (d, J=8.4 Hz, 1H, H-1E), 4.11 (d, J=3.1 Hz, 1H, H-2C), 4.08 (dd, J=3.4, 1.8 Hz, 1H, H-2D), 3.99 (t, J=8.5 Hz, 2H, H-4A, H-4B), 3.96-3.86 (m, 3H, H-2A, H-6Ca, H-6 Da), 3.86-3.75 (m, 9H, H-6Ea, H-2B, H-4C, H-6Aa, H-6Ab, H-3D, H-3D', H-2D', H-5D), 3.75-3.53 (m, 14H, H-6E'a, H-6E'b, H-6Eb, H-6D'a, H-6Ba, H-3B, H-2E', H-2E, H-6Db, H-6D'b, H-6Cb, H-6Bb, H-5D', H-3A), 3.53-3.41 (m, 6H, H-4D', H-4D, H-5A, H-3E, H-3E', H-3C), 3.37-3.24 (m, 4H, H-4E', H-4E, H-5B, H-5E), 3.20-3.13 (m, 2H, H-3E', H-5C), 2.11 (t, J=5.7 Hz, 3H, Ac), 1.95 (dd, J=18.2, 6.1 Hz, 3H, Ac), 1.88-1.83 (m, 3H, Ac), 1.70 (dd, J=18.1, 5.9 Hz, 3H, Ac); $^{13}$C NMR from HSQC experiment (126 MHz, MeOD): 127.9, 127.8, 127.7, 127.4, 100.5(C-1E'), 100.1(C-1A, C-1B, C-1C, C-1E), 99.6(C-1D), 97.2(C-1D'), 81.5, 80.8, 80.4, 77.6, 77.1, 76.6, 76.1, 75.9, 74.9, 74.9, 74.0, 73.9, 73.8, 73.5, 73.1, 73.0, 72.9, 70.5, 70.3, 70.3, 70.2, 70.2, 68.5, 68.4, 67.8, 65.8, 61.9, 61.7, 61.5, 61.0, 55.8, 55.8, 54.5, 22.1, 22.1, 21.6.

[(2-acetamido-2-deoxy-β-D-glucopyranosyl-(1→2)-α-D-mannopyranosyl)-(1→6)]-[2-acetamido-2-deoxy-β-D-glucopyranosyl-(1→2)-α-D-mannopyranosyl-(1→3)]-β-D-mannopyranosyl-(1→4)-2-acetamido-2-deoxy-β-D-glucopyranosyl-(1→4)-2-acetamido-2-deoxy-α,β-D-glucopyranose ($^{13}$C$_8$) (14) ($^{13}$C$_8$-G0(Bn$_5$))

Heptasaccharide 13 (13 mg, 7.3 µmol) was dissolved in 1 mL of MeOH and passed through the hydrogenator using a 10% Pd/C cartridge and MeOH as solvent with a flow rate of 1 mL/min, at 50° C. using full hydrogen conditions. The resulting mixture was concentrated, redissolved in water and purified on a graphite cartridge to give the title compound (7 mg, 72%).

$^1$H NMR (500 MHz, D$_2$O) δ 5.20 (d, J=2.5 Hz, 0.6H, H-1A$_{\alpha\text{-}GlcNAc}$), 5.13 (d, J=1.8 Hz, 1H, H-1D$_{\alpha\text{-}1,3\text{-}Man}$), 4.93 (d, J=1.8 Hz, 1H, H-1D'$_{\alpha\text{-}1,6\text{-}Man}$), 4.71 (d, J=8.0 Hz, 0.4H, H-1A$_{\beta\text{-}GlcNAc}$), 4.62 (dd, J=7.8, 4.4 Hz, 1H, H-1B$_{\beta\text{-}GlcNAc}$), 4.57 (d, J=8.4 Hz, 2H, H-1E$_{\beta\text{-}GlcNAc}$, H-1E'$_{\beta\text{-}GlcNAc}$), 4.26 (d, J=2.5 Hz, 1H, H-2C), 4.20 (dd, J=3.4, 1.6 Hz, 1H, H-2D), 4.12 (dd, J=3.4, 1.7 Hz, 1H, H-2D'), 4.04-3.85 (m, 10H), 3.85-3.39 (m, 30H), 2.25-2.13 (m, 6H, 2Ac), 1.98-1.88 (m, 6H, 2Ac). $^{13}$C NMR (126 MHz, D$_2$O) δ 101.4 (C-1B$_{\beta\text{-}GlcNAc}$), 100.4 (C-1C$_{\beta\text{-}1,4\text{-}Man}$), 99.6 (C-1D$_{\alpha\text{-}1,3\text{-}Man}$, C-1E$_{\beta\text{-}GlcNAc}$, C-1E'$_{\beta\text{-}GlcNAc}$), 97.0(C-1D'$_{\alpha\text{-}1,6\text{-}Man}$), 94.8(C-1A$_{\beta\text{-}GlcNAc}$), 90.4(C-1A$_{\alpha\text{-}GlcNAc}$), 80.4, 79.6, 79.5, 79.2, 76.4, 76.3, 75.8, 75.8, 74.6, 74.4, 74.3, 73.5, 73.4, 73.3, 72.8, 72.5, 72.0, 70.2, 70.0, 69.9, 69.6, 69.4, 69.4, 69.2, 67.3, 67.3, 65.8, 65.7, 61.7, 61.6, 60.6, 60.1, 60.0, 59.9, 56.1, 55.3, 54.9, 53.6; HRMS (ESI): m/z calculated for C$_{42}$$^{13}$C$_8$H$_{84}$N$_4$O$_{36}$Na: 1347.5031 [M+Na]$^+$, found 1347.5131.

Synthesis of a Triantennary Complex N-Glycan Core

Figure 4A:
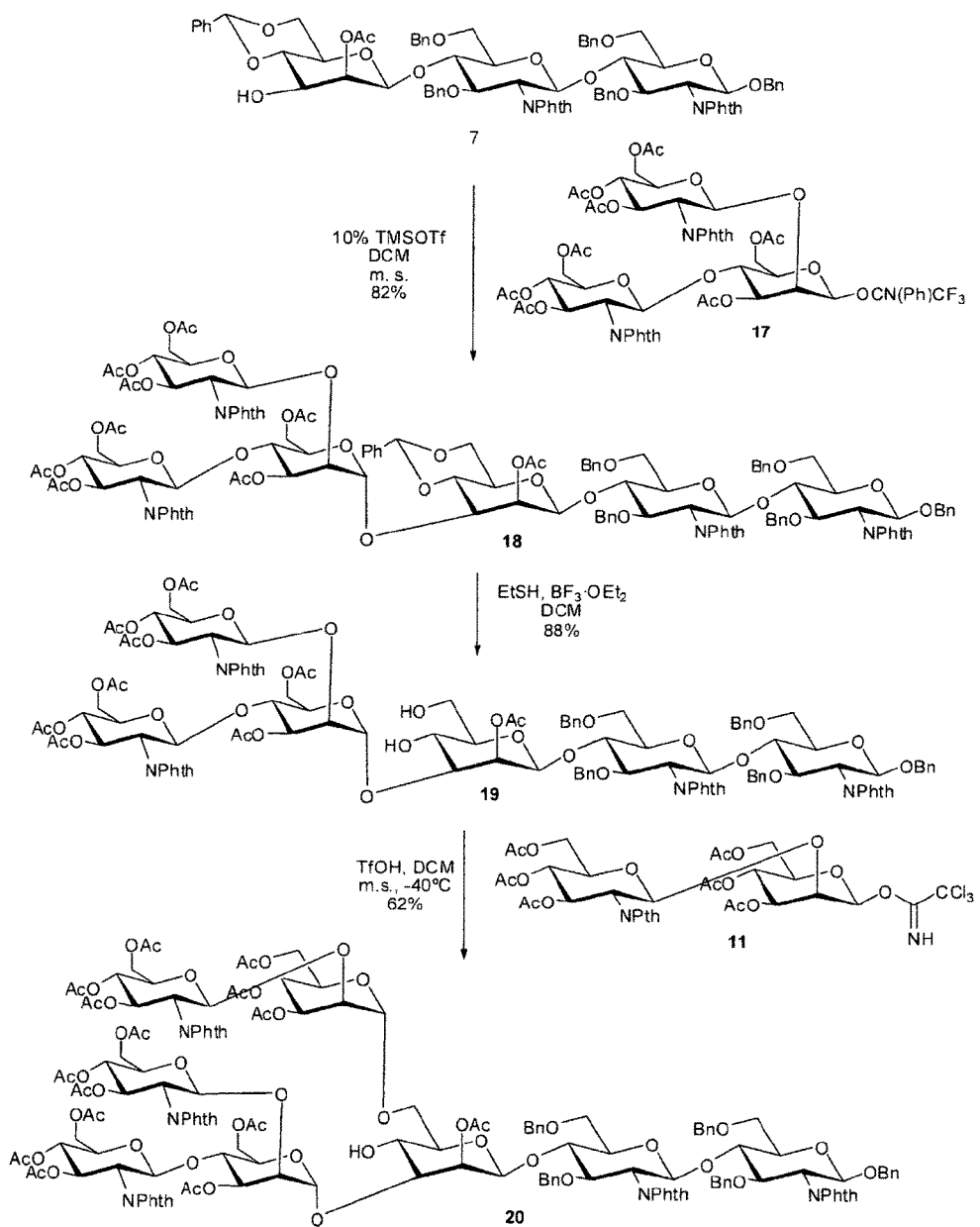
FIG. 4. The synthesis of isotopically labelled tri-antennary [(2-acetamido-β-D-glucopyranosyl)-(1→2)-α-D-mannopyrannosyl]-(1→6)-[di-(2-acetamido-β-D-glucopyranosyl)-(1→2)-(1→4)-α-D-mannopyrannosyl]-(1→3)-β-D-mannopyranosyl-(1→4)-2-acetamido-3,6-di-O-benzyl-2-deoxy-β-D-glucopyranosyl-(1→4)-2-acetamido-1,3,6-tri-O-benzyl-2-deoxy-β-D-glucopyranoside, wherein each acetyl group is $^{13}C_2$-isotopically-labelled.
Figure 4B:
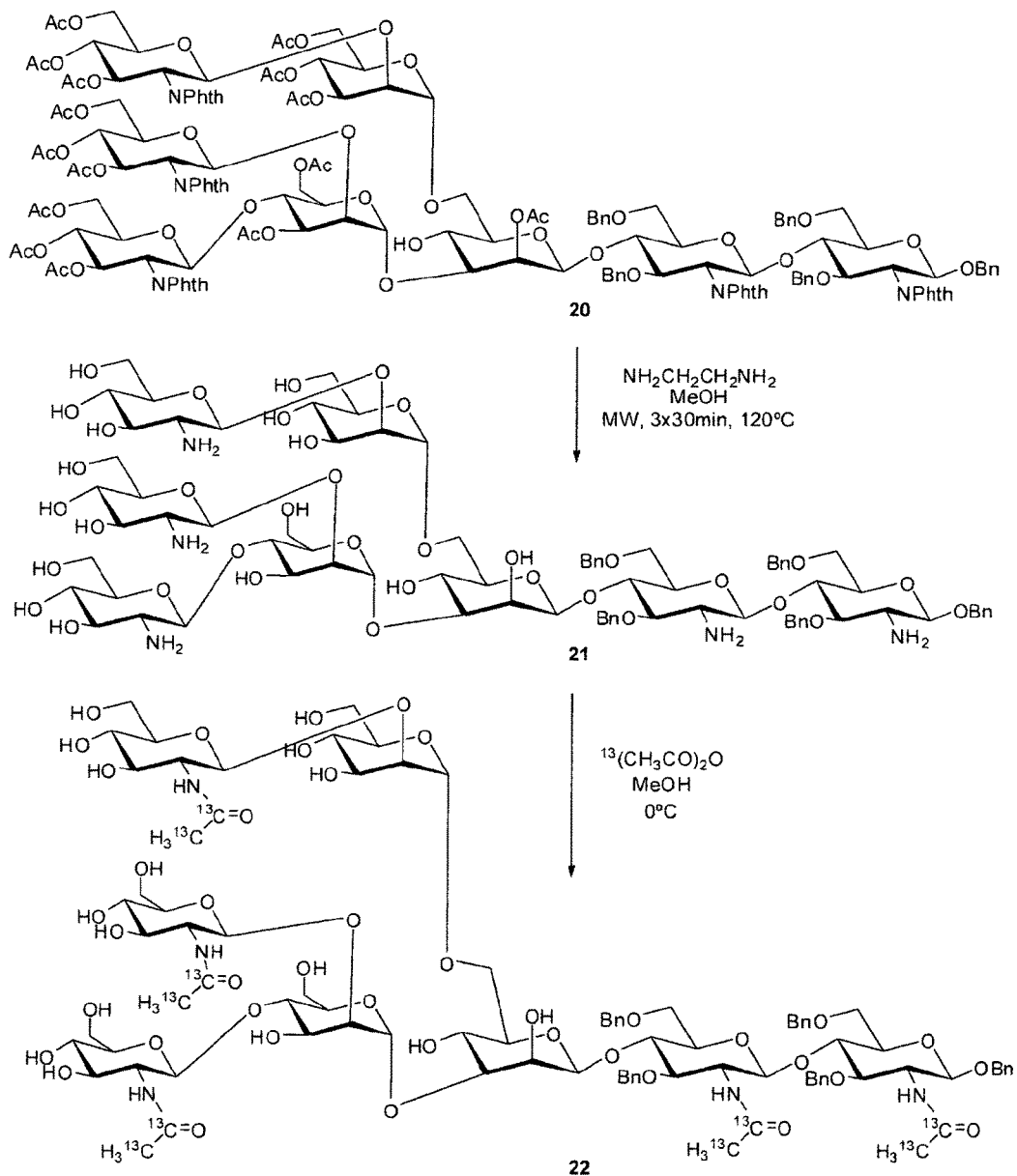

The following synthesis is numbered with respect to the corresponding chemicals structures shown in FIG. 4.

Benzyl [di-(O-3,4,6-tri-O-acetyl-2-deoxy-2-phtalimido-β-D-glucopyranosyl)-(1→2)-(1→4)-3,6-di-O-acetyl-α-D-mannopyrannosyl]-(1→3)-2-O-acetyl-4,6-O-benzylidene-β-D-mannopyranosyl-(1→4)-3,6-di-O-benzyl-2-deoxy-2-phtalimido-β-D-glucopiranosyl-(1→4)-3,6-di-O-benzyl-2-deoxy-2-phtalimido-β-D-glucopyranoside (18)

A solution of acceptor 7 (0.18 g, 0.13 mmol) and donor 17 (0.21 g, 0.16 mmol, 1.2 eq) in dry DCM (2 mL), with molecular sieves was stirred at room temperature for 1 h. TMSOTf (2 µL, 13 µmol, 10%) was added and the reaction was stirred for 1h at room temperature. The reaction was quenched by the addition of Et$_3$N (25 µL), filtered through a plug of celite and the filtrate concentrated. The crude residue was purified by flash column chromatography (Hexane:EtOAc 2:3), to give the titled compound (0.27 g, 82%). [α]$^{20}_D$: −24.0 (c 1.05, CH$_3$C$_1$). $^1$H NMR (500 MHz, CDCl$_3$): 7.90-7.65 (m, 17H, H-arom), 7.54 (m, 2H, H-arom), 7.42-7.26 (m, 13H, H-arom), 7.06-6.96 (m, 11H, H-arom), 6.79 (m, 3H, H-arom), 5.76 (dd, J=9.0, 10.7 Hz, 1H, H-3E'), 5.44 (m, 3H, H-1E', H-3E, CHPh), 5.27 (d, J=7.8 Hz, 1H, H-1A), 5.18 (m, 2H, H-2C, H-4E'), 4.96 (d, J 8.5 Hz, 1H, H-1B), 4.83 (m, 6H, H-4E, 2×CH$_2$Bn, H-3D, H-1D, H-1E), 4.71, 4.65 (d, J=12.0 Hz, 1H, CH$_2$ Bn), 4.52 (m, 4H, H-1C, 3×CH$_2$Bn), 4.39 (m, 3H, 3×CH$_2$Bn), 4.29-4.07 (m, 13H, H-2E', 2×H-6E', H-2A, H-2B, H-3A, H-3B, H-4A, H-4B, H-6Ca, H-5E', H-2E, H-6 Da), 3.98 (m, 3H, H-5D, H-6Ea, H-2D), 3.82 (t, J=10.3 Hz, 1H, H-4D), 3.73 (t, J=8.5 Hz, 1H, H-4C), 3.75-3.39 (m, 8H, 2×H-6A, H-6Eb, 2×H-6B, H-3C, H-6Cb, H-6Db), 3.32 (m, 1H, H-5B), 3.19 (m, 1H, H-5A), 2.99 (m, 1H, H-5C), 2.26, 2.12 (s, 3H, CH$_3$ Ac), 2.08 (m, 3H, H-5E), 2.04, 2.03, 2.02, 1.84, 1.83, 1.72, 1.54 (s, 3H, CH$_3$ Ac). $^{13}$C NMR (126 MHz, CDCl$_3$): 170.8, 170.5, 170.4, 170.2, 170.1, 170.0, 169.5, 169.2, 167.3 138.7, 138.6, 138.4, 137.8, 137.3, 137.2, 134.3, 134.0, 133.5, 131.7, 131.4, 128.9, 128.7, 128.5, 128.2, 128.1, 127.0, 127.7, 127.6, 127.5, 127.4, 127.2, 126.9, 126.8, 123.8, 123.4, 102.3, 98.1 (C-1C), 97.6 (C-1D), 97.1 (C-1A, C-1B), 95.8 (C-1E), 94.8 (C-1E'), 78.8, 77.8, 76.6, 75.9, 75.1, 74.5, 74.3, 74.2, 73.3, 72.8, 72.7, 71.8, 71.0, 70.8, 70.5, 70.4, 68.6, 68.5, 68.4, 68.1, 67.4, 66.0, 63.6, 61.6, 61.1, 56.5, 55.7, 54.8, 54.0, 20.9, 20.7, 20.6, 20.4, 20.2.

Benzyl [di-(O-3,4,6-tri-O-acetyl-2-deoxy-2-phtalimido-β-D-glucopyranosyl)-(1→2)-(1-4)-3,6-di-O-acetyl-α-D-mannopyrannosyl]-(1→3)-2-O-acetyl-β-D-mannopyranosyl-(1→4)-3,6-di-O-benzyl-2-deoxy-2-phtalimido-β-D-glucopiranosyl-(1→4)-3,6-di-O-benzyl-2-deoxy-2-phtalimido-β-D-glucopyranoside (19)

EtSH (31 µL, 0.25 mmol, 5 eq) and BF$_3$.OEt$_2$ (2 µL, 10 µmol, 20%) were added at 0° C. to a solution of hexasaccharide 18 (0.14 g, 0.05 mmol) in DCM (2 mL). The reaction mixture was stirred at room temperature until complete conversion (2 hour). Then, it was quenched with Et$_3$N, concentrated and purified by flash column chromatography (Hexane:EtOAc 1:3), obtaining the titled compound (0.12 g, 88%).

[α]$^{20}_D$: +1.9 (c 0.93, CDCl$_3$). $^1$H NMR (500 MHz, CDCl$_3$): 7.90-7.66 (m, 15H, H-arom), 7.32-7.24 (m, 12H, H-arom), 7.17 (m, 1H, H-arom), 7.02-6.98 (m, 10H, H-arom), 6.76 (m, 3H, H-arom), 5.78 (dd, J=9.1, 10.7 Hz, 1H, H-3E), 5.73 (m, dd, J=9.1, 10.8 Hz, 1H, H-3E'), 5.48 (d, J=7.8 Hz, 1H, H-1E'), 5.27 (m, 2H, H-1E, H-1A), 5.22 (t, J=9.8 Hz, 1H, H-4E'), 5.15 (d, J=3.4 Hz, 1H, H-2C), 5.10 (t, J=9.7 Hz, 1H, H-4E), 5.05 (dd, J=3.0, 8.5 Hz, 1H, H-3D), 4.96 (d, 1H, J=8.2 Hz, H-1B), 4.86 (m, 3H, CH$_2$Bn, H-1D), 4.70 (d, J=12.0 Hz, 1H, 1×CH$_2$Bn), 4.58 (d, J=12.0 Hz, 1H, 1×CH$_2$Bn), 4.52 (m, 4H, H-1C, 3×CH$_2$Bn), 4.45 (m, 1H, H-6E'a), 4.39 (m, 3H, 3×CH$_2$Bn), 4.34-4.04 (m, 15H, H-2E, H-2E', 2×H-6E, H-6E'b, H-2A, H-2B, H-3A, H-3B, H-4A, H-4B, H-2D, H-5E', H-6 Da, H-4D), 3.82 (m, 1H, H-5E), 3.78 (m, 1H, H-5D), 3.69 (m, 2H, H-4C, H-6Ca), 3.62-3.48 (m, 5H, H-6Aa, H-6Ba, H-6Cb, H-6Ab, H-6Db), 3.44 (dd, J=3.9, 11.3 Hz, 1H, H-6Bb), 3.31 (m, 2H, H-5B, H-3C), 3.20 (m, 1H, H-5A), 2.94 (m, 1H, H-5C), 2.19, 2.15, 2.11, 2.07, 2.04, 2.02, 1.88, 1.85 (s, 3H, CH$_3$ Ac). $^{13}$C NMR (126 MHz, CDCl$_3$): 170.7, 170.2, 170.1, 170.0, 169.5, 167.6, 138.6, 138.5, 138.3, 137.8, 137.2, 134.4, 134.3, 131.6, 131.3, 128.6, 128.2, 128.1, 128.0, 127.9, 127.8, 127.5, 127.4, 127.3, 127.2, 126.8, 123.7, 123.1, 98.1 (C-1D), 97.4 ($C_{1E}$, C-1C), 97.1 (C-1A, C-1B), 95.9 (C-1E'), 77.2, 76.5, 75.9, 75.3, 75.2, 74.5, 74.4, 74.3, 73.1, 72.8, 71.8, 71.3, 70.7, 70.5, 70.4, 68.9, 68.8, 68.5, 68.3, 68.1, 67.1, 62.7, 62.0, 61.1, 56.5, 55.7, 54.8, 54.4, 20.8, 20.7, 20.6, 20.4.

Benzyl [di-(O-3,4,6-tri-O-acetyl-2-deoxy-2-phtalimido-β-D-glucopyranosyl)-(1→2)-(1→4)-3,6-di-O-acetyl-α-D-mannopyrannosyl]-(1→3)-[O-3,4,6-tri-O-acetyl-2-deoxy-2-phthalimido-β-D-glucopyranosyl-(1→2)-3,4,6-tri-O-acetyl-α-D-mannopyranosyl]-(1→6)-2-O-acetyl-β-D-mannopyranosyl-(1→4)-3,6-di-O-benzyl-2-deoxy-2-phtalimido-β-D-glucopiranosyl-(1→4)-3,6-di-O-benzyl-2-deoxy-2-phtalimido-β-D-glucopyranoside (20)

A suspension of acceptor 19 (75 mg, 0.03 mmol), donor 11 (41 mg, 0.05 mmol, 1.5 eq, synthesized according to Unverzagt, C.; Eller, S.; Mezzato, S.; Schuberth, R. *Chem. Eur. J.* 2007, 14, 1304-1311) and molecular sieves in dry DCM (9.8 mL) was stirred at room temperature for 1h. The mixture was cooled to −40° C. and TfOH (1 μL, 0.01 μmol, 33%) was added. The reaction mixture was stirred at −40° C. until donor had disappeared (1h). Then, the reaction was quenched with $Et_3N$, filtered over a plug of celite and concentrated. The residue was purified by flash column chromatography, obtaining the titled compound (60 mg, 62%).

$[\alpha]^{20}_D$: +2.1 (c 0.53, $CH_3C_1$). $^1H$ NMR (500 MHz, $CDCl_3$): 7.88-7.61 (m, 19H, H-arom), 7.30-7.23 (m, 11H, H-arom), 7.18, 7.04 (m, 1H, H-arom), 7.01-6.93 (m, 7H, H-arom), 6.85, 6.75 (m, 3H, H-arom), 5.79 (dd, J=9.0, 10.7 Hz, 1H, H-$_3$v), 5.70 (m, 2H, H-3E, H-3E"), 5.45 (d, J=8.2 Hz, 1H, H-1E'), 5.33 (d, J=8.4 Hz, 1H, H-1E), 5.24-5.09 (m, 7H, H-1E", H-1A, H-4E', H-4D', H-2C, H-4E, H-4E"), 4.98. (m, 2H, H-3D, H-3D'), 4.94 (d, J=8.5 Hz, 1H, H-1B), 4.83 (d, J=12.0 Hz, 1H, 1×$CH_2Bn$), 4.78 (d, J=1.8 Hz, 1H, H-1D), 4.71 (m, 2H, 2×$CH_2Bn$), 4.59 (d, J=12.0 Hz, 1H, 1×$CH_2Bn$), 4.51-3.98 (m, 27H, H-1C, 6×$CH_2Bn$, 2×H-6E', H-1D', H-2E", H-2E, 2×H-6E, H-2E', H-6E"a, H-2D, H-2D', H-2B, H-3B, H-4B, H-2A, H-3A, H-4A, H-5E', H-6 Da, H-4D), 3.87 (m, 2H, H-6E"b, H-5E), 3.81-3.69 (m, 6H, H-5D, H-6D'a, H-4C, H-6Ca, H6Db, H5D'), 3.59-3.45 (m, 5H, 2×H-6Aa, H-6Ba, H-6D'b, H-5E"), 3.39 (dd, J=4.0, 11.5 Hz, 1H, H-6Bb), 3.33 (dd, J=5.0, 10.3 Hz, 1H, H-6Cb), 3.26 (m, 2H, H-5B, H-3C), 3.17 (m, 1H, H-5A), 3.01 (m, 1H H-5C), 2.15, 2.09, 2.09, 2.05, 2.04, 2.01, 2.01, 2.00, 1.95, 1.89, 1.88, 1.87, 1.85, 1.85 (s, 3H, $CH_3$ Ac). $^{13}C$ NMR (126 MHz, $CDCl_3$): 170.8, 170.7, 170.6, 170.5, 170.3, 170.2, 170.1, 170.0, 169.9, 169.4, 169.3, 169.2, 167.6, 167.4, 138.8, 138.6, 138.3, 138.0, 137.2, 134.3, 133.4, 131.7, 131.3, 128.5, 128.2, 128.1, 128.0, 127.9, 127.8, 127.7, 127.4, 127.2, 126.8, 123.7, 123.5, 123.0, 98.6 (C-1D), 97.7 (C-1C, C-1D'), 97.3 (C-1E), 97.2 (C-1E"), 97.1 (C-1A, C-1B), 95.9 (C-1E'), 77.7, 76.5, 75.8, 75.0, 74.5, 74.3, 73.0, 72.8, 72.4, 71.7, 71.2, 70.7, 70.6, 70.4, 70.2, 70.0, 69.6, 69.0, 68.9, 68.8, 68.6, 68.3, 68.1, 65.5, 62.7, 62.4, 61.9, 61.7, 61.5, 61.2, 56.5, 55.7, 54.9, 54.4, 20.7, 20.6, 20.5, 20.4, 20.3.

[(2-acetamido-β-D-glucopyranosyl)-(1→2)-α-D-mannopyrannosyl]-(1→6)-[di-(2-acetamido-β-D-glucopyranosyl)-(1→2)-(1→4)-α-D-mannopyrannosyl]-(1→3)-β-D-mannopyranosyl-(1→4)-2-acetamido-3,6-di-O-benzyl-2-deoxy-β-D-glucopyranosyl-(1→4)-2-acetamido-1,3,6-tri-O-benzyl-2-deoxy-β-D-glucopyranoside ($^{13}C_{10}$) (22)

To a solution of compound 20 (43 mg, 14.1 μmol) in MeOH:DCM 2:1 (300:150 μL), NaOMe (42 μL, 21.2 μL, 1.5 eq) was added. After stirring 1 h at room temperature, MeOH (300 μL) and ethylenediamine (300 μL) were added and the mixture heated for 3 cycles of 30 min at 120° C. in a microwave. The mixture was concentrated to dryness using toluene and ethanol. The crude residue was purified by Sephadex LH-20 column (MeOH) to give compound 21. Compound 21 was dissolved in MeOH (200 μL) at 0° C. and acetic anhydride $^{13}C_a$ was added. After 2 h, EtOH was added and the mixture concentrated and purified by Sephadex LH-20 column (MeOH) to give the titled compound (11 mg, 40%, 2 steps).

$^1H$ NMR (500 MHz, MeOD): 7.41-7.27 (m, 22H, H-arom), 7.19 (m, 3H, H-arom), 5.03 (m, 3H, H-1D, 2×$CH_2Bn$), 4.85 (d, J=12.0 Hz, 1H, 1×$CH_2Bn$), 4.80 (d, J=1.9 Hz, 1H, H-1D'), 4.77 (d, J=12.0 Hz, 1H, 1×$CH_2Bn$), 4.68-4.57 (m, 6H, H-1C, H-1B, 4×$CH_2Bn$), 5.50 (m, 2H, H-1E", H-1A), 4.46 (s, 2H, 2×$CH_2Bn$), 4.43 (d, J=8.3 Hz, 1H, H-1E), 4.32 (d, J=8.3 Hz, 1H, H-1E'), 4.13 (m, 1H, H-2D), 4.08 (m, 2H, H-3D, H-2C), 4.02 (m, 2H, H-4A, H-4B), 3.95-3.58 (m, 30H, H-2A, 2×H-6C, 2×H-6E, 2×H-6E", 2×H-6E', 2×H-6D, 2×H-6D', H-5D, H-2D', H-2B, H-4C, H-3D', 2×H-6B, 2×H-6A, H-2E, H-4D, H-3B, H-2B, H-3A, H-2E', H-5D', H-4D'), 3.52-3.43 (m, 5H, H-5A, H-3E, H-3E', H-3E", H-3C), 3.36 (m, 3H, H-5E", H-4E', H-4E"), 3.33 (m, 2H, H-5B, H-4E), 3.26 (m, 1H, H-5E), 3.18 (m, 2H, H-5C), 2.14 (m, 4.5H, $^{13}CH_3$ Ac), 1.97 (dd, J=6.4, 17.8 Hz, 3H, $^{13}CH_3$ Ac), 1.89 (m, 4.5H, $^{13}CH_3$ Ac), 1.72 (dd, J=6.4, 17.8 Hz, 3H, $^{13}CH_3$ Ac). $^{13C}$ NMR (126 MHz, MeOD, HSQC): 128.2-126.6, 131.6 (C-1E"), 100.5 (C-1E, C-1E"), 100.2 (C-1A), 100.0 (C-1C, C-1B), 99.6 (C-1D), 97.1 (C-1D'), 82.0, 81.0, 80.4, 78.1, 77.7, 76.5, 75.6, 75.2, 74.7, 73.9, 73.1, 72.2, 70.3, 68.3, 67.6, 65.8, 61.2, 55.7, 54.6, 22.3 ($^{13}CH_3$).

Enzymatic Elongation

[β-D-galactopyranosyl-(1→4)-2-acetamido-2-deoxy-β-D-glucopyranosyl-(1→2)-α-D-mannopyranosyl)-(1→6)]-[β-D-galactopyranosyl-(1→4)-2-acetamido-2-deoxy-β-D-glucopyranosyl-(1→2)-α-D-mannopyranosyl-(1→3)]-β-D-mannopyranosyl-(1→4)-2-acetamido-2-deoxy-β-D-glucopyranosyl-(1→4)-2-acetamido-2-deoxy-α,β-D-glucopyranose (15)

A solution (1 mL) of 14 (2.126 mg, 1.6 μmol), Uridine 5'-diphospho-α-D-galactose disodium salt UDP-Gal (2.280 mg, 3.74 μmol, 2.4 eq), bovine serum albumin BSA (1 mg), 200 mU of bovine milk β-1,4-galactosyltransferase 2.4.4.22, 9.2 U of alkaline phosphatase 3.1.3.1. and $MnCl_2$ (10 mM) in 770 μL Hepes buffer (50 mM, pH=7.4) was incubated at 37° C. for 18h. The resulting mixture was heated at 95° C. for 5 min to precipitate the enzyme. After centrifugation, the supernatant was purified through a graphite cartridge to give the title compound (2.09, 78%).

$^1H$ NMR (500 MHz, $D_2O$) δ 5.12 (d, J=2.7 Hz, 0.6H, H-$1_{\alpha\text{-}GlcNAc}$), 5.05 (d, J=1.4 Hz, 1H, H-$1_{\alpha\text{-}1,3\text{-}Man}$), 4.86 (d, J=1.6 Hz, 1H, H-$1_{\alpha\text{-}GlcNAc}$), 4.66-4.59 (m, 0.4H, H-$1_{\beta\text{-}GlcNAc}$), 4.53 (dd, J=15.9, 7.9 Hz, 3H, H-$1_{\beta\text{-}GlcNAc}$), 4.40 (dd, J=7.8, 3.1 Hz, 2H, H-$1_{\beta\text{-}Gal}$), 4.18 (d, J=2.7 Hz, 1H), 4.12 (dd, J=3.3, 1.6 Hz, 1H), 4.08-4.00 (m, 1H), 3.95-3.36 (m, 60H), 2.17-2.04 (m, 6H, Ac), 1.93-1.78 (m, 6H, Ac). $^{13}C$ NMR selected peaks from HSQC experiment (126 MHz, $D_2O$) δ=102.9 (C-$1_{\beta\text{-}Gal}$) 101.3 (H-$1_{\beta\text{-}GlcNAc}$), 100.4 (C-$1_{\beta\text{-}Man}$), 99.6 (C-$1_{\alpha\text{-}1,3\text{-}Man}$), 99.5 (C-$1_{\beta\text{-}GlcNAc}$), 97.1 (C-$1_{\alpha\text{-}1,6\text{-}Man}$), 94.8 (C-$1_{\beta\text{-}GlcNAc}$), 90.4 (C-$1_{\alpha\text{-}GlcNAc}$).

[(2-acetamido-2-deoxy-β-D-glucopyranosyl-(1→2)-α-D-mannopyranosyl)-(1→6)]-[2-acetamido-2-deoxy-β-D-glucopyranosyl-(1→2)-α-D-mannopyranosyl-(1→3)]-β-D-mannopyranosyl-(1→4)-2-acetamido-2-deoxy-β-D-glucopyranosyl-(1→4)-[α-L-fucopyranosyl-(1→6)]-2-acetamido-2-deoxy-α,β-D-glucopyranose (16)

A solution (1 mL) of 14 (3.030, mg, 2.28 μmol), Guanosine 5'-diphospho-β-L-fucose disodium salt GDP-Fuc (1.760 mg, 2.77 μmol, 1.2 eq), bovine serum albumin BSA (1 mg), a core α-1,6-fucosyltransferase (50 μL, 0.66 mg/mL) and MnCl$_2$ (20 mM) in 770 μL MES buffer (80 mM, pH=6.5) was incubated at room temperature for 18h. The resulting mixture was heated at 95° C. for 5 min to precipitate the enzyme. After centrifugation the supernatant was purified through a graphite cartridge to give the title compound (2.73 mg, 82%).

$^1$H NMR (500 MHz, D$_2$O) δ 5.11 (d, J=3.2 Hz, 0.6H, H-1$_{α\text{-}GlcNAc}$), 5.04 (d, J=1.8 Hz, 1H, H-1$_{α\text{-}1,3\text{-}man}$), 4.88-4.79 (m, 2H, H-1$_{α\text{-}1,6\text{-}Man}$, H-1$_{α\text{-}Fuc}$), 4.64-4.55 (m, 0.4H+1H, H-1$_{β\text{-}1,6\text{-}Man}$), 4.48 (d, J=8.4 Hz, 2H, H-1$_{β\text{-}GlcNAc}$), 4.18 (d, J=2.4 Hz, 1H), 4.11 (dd, J=3.3, 1.6 Hz, 1H), 4.09-3.98 (m, 2H), 3.98-3.75 (m, 11H), 3.75-3.31 (m, 33H), 2.25-2.04 (m, 6H, Ac), 1.95-1.78 (m, 6H, Ac), 1.14 (dd, J=6.6, 4.8 Hz, 3H, CH$_3$ Fuc). $^{13}$C NMR selected from HSQC experiment (126 MHz, D$_2$O) δ=101.0 (C-1$_{β\text{-}GlcNAc}$), 100.3 (C-1$_{βMan}$), 99.6 (C-1$_{β\text{-}GlcNAc}$), 99.5 (C-1$_{α\text{-}1,3\text{-}Man}$), 99.5 (C-1$_{α\text{-}Fuc}$), 97.0(C-1$_{α\text{-}1,6\text{-}Man}$), 94.8 (C-1$_{β\text{-}GlcNAc}$), 90.4 (C-1$_{α\text{-}GlcNAc}$, 15.4 (CH$_3$ Fuc).

[β-D-galactopyranosyl-(1→4)-2-acetamido-2-deoxy-β-D-glucopyranosyl-(1→2)-α-D-mannopyranosyl)-(1→6)]-[β-D-galactopyranosyl-(1→4)-2-acetamido-2-deoxy-β-D-glucopyranosyl-(1→2)-α-D-mannopyranosyl-(1→3)]-β-D-mannopyranosyl-(1→4)-2-acetamido-2-deoxy-β-D-glucopyranosyl-(1→4)-[α-L-fucopyranosyl-(1→6)]-2-acetamido-2-deoxy-α,β-D-glucopyranose (17)

A solution (0.5 mL) of 16 (1.836 mg, 1.6 μmol), Uridine 5'-diphospho-α-D-galactose disodium salt UDP-Gal (2.210 mg, 3.62 μmol, 2.9 eq), bovine serum albumin BSA (1 mg), 200 mU of bovine milk β-1,4-galactosyltransferase 2.4.4.22, 9.2 U of alkaline phosphatase 3.1.3.1. and MnCl$_2$ (10 mM) in 450 μL Hepes buffer (50 mM, pH=7.4) was incubated at 37° C. for 18h. The resulting mixture was heated at 95° C. for 5 min to precipitate the enzyme. After centrifugation the supernatant was purified through a graphite cartridge, to give the title compound (1.80 mg, 80%).

$^1$H NMR (500 MHz, D$_2$O) δ 5.11 (d, J=3.1 Hz, 0.6H, H-1$_{α\text{-}GlcNAc}$), 5.05 (d, J=1.5 Hz, 1H, H-1$_{α\text{-}1,3\text{-}Man}$), 4.85 (s, 1H, H-1$_{α\text{-}1,6\text{-}Man}$), 4.82 (t, J=3.7 Hz, 1H, H-1$_{α\text{-}Fuc}$), 4.62 (d, J=7.9 Hz, 0.4H, H-1$_{β\text{-}GlcNAc}$), 4.59 (d, J=7.7 Hz, 1H, H-1$_{β\text{-}GlcNAc}$), 4.51 (d, J=7.7 Hz, 2H, H-1$_{β\text{-}GlcNAc}$), 4.40 (dd, J=7.8, 2.7 Hz, 2H, H-1$_{β\text{-}Gal}$) 4.18 (s, 1H), 4.12 (d, J=3.3 Hz, 1H), 4.08-4.00 (m, 2H), 3.97-3.39 (m, 54H), 2.18-2.07 (m, 6H), 1.92-1.81 (m, 6H, Ac), 1.14 (dd, J=6.6, 5.0 Hz, 3H, CH$_3$ Fuc).$^{13}$C NMR peaks selected from HSQC experiment (126 MHz, D$_2$O) δ=102.9 (H-1$_{β\text{-}Gal}$), 101.0 (H-1$_{β\text{-}GlcNAc}$), 100.4 (H-1$_{β\text{-}Man}$), 99.5 (H-1$_{β\text{-}GlcNAc}$), 99.5 (H-1$_{β\text{-}1,3\text{-}Man}$), 99.3 (H-1$_{α\text{-}Fuc}$), 96.8 (H-1$_{α\text{-}1,6\text{-}Man}$), 94.8 (H-1$_{β\text{-}GlcNAc}$), 90.4 (C-1$_{α\text{-}GlcNAc}$), 15.5 (CH$_3$, Fuc).

Preparation of Asymmetric Mono-Galactosylated Glycan Standards

Galactosylation of $^{13}$C$_8$-G0(Bn$_5$)

The partially deprotected $^{13}$C$_8$-G0(Bn$_5$) standard 13 (1.1 mg) was treated with β-1,4-galactosyltransferase (200 mU) and uridine diphosphate galactose (UDP-Gal, 1.25 equivalents) in HEPES buffer 50 mM at pH 7.4, containing MnCl$_2$ 2 mM and BSA. After 1h of reaction at 37° C. the proteic fraction was precipitated by heating at 95° C. for 5 minutes and removed by filtration. This solution was directly analysed by UPLC-MS showing a 23% and 26% conversion to $^{13}$C$_8$-G1$^6$(Bn$_5$) and $^{13}$C$_8$-G1$^3$(Bn$_5$) respectively.

This reaction could be scaled up to the use of 10 mg of $^{13}$C$_9$-G0(Bn$_5$) as acceptor.

The reaction crude after protein precipitation from the enzymatic elongation of 10 mg of $^{13}$C$_8$-G0(Bn$_5$) was evaporated and then the different compounds were purified by HPLC in a C$_{18}$ semi-preparative column in reverse phase water/ACN to yield the compounds $^{13}$C$_8$-G1$^3$(Bn$_5$) (2.4 mg), $^{13}$C$_8$-G1$^6$(Bn$_5$) (2.2 mg) and $^{13}$C$_8$-G2 (Bn$_5$) (2.0 mg) in pure form (wherein G1$^3$ and G1$^6$ denote the respective mono-galactosylated compounds and G2 the bis-galactosylated compound).

Both isomeric mono-galactosylated compounds were subjected to hydrogenolysis in MeOH using 1 atm of H$_2$ gas in an H-Cube flow reactor with a 10% Pd/C cartridge, obtaining the $^{13}$C-labeled N-glycans $^{13}$C$_8$-G1$^3$ (1.2 mg) and $^{13}$C$_8$-G1$^6$ (1.1 mg) in pure form.

Fucosylation of $^{13}$C$_8$-G1$^6$

The compound $^{13}$C$_8$-G1$^6$ (1.1 mg) was treated with a core α-1,6-fucosyltransferase and guanosine diphosphate fucose (GDP-Fuc, 1.10 equivalents) in MES buffer 50 mM at pH 6.5, containing MgCl$_2$ 2 mM. After 18h of reaction at 30° C. the proteic fraction was precipitated by heating at 95° C. for 5 minutes and filtered off. The glycan $^{13}$C$_8$-G1$^6$F was purified with a graphitized carbon cartridge.

Galactosylation of $^{13}$C$_8$-G0(Bn$_5$)

The partially deprotected $^{13}$C$_8$-G0(Bn$_5$) standard (20 μg) was treated with β-1,4-galactosyltransferase (200 mU) and uridine diphosphate galactose (UDP-Gal, 6.0 equivalents) in HEPES buffer 50 mM at pH 7.4, containing MnCl$_2$ 2 mM and BSA. After 1h of reaction at 37° C. the proteic fraction was precipitated by heating at 95° C. for 5 minutes and filtered off.

This solution was directly analysed by UPLC-MS' showing complete conversion to $^{13}$C$_8$-G2(Bn$_5$).

The bis-galactosylated compound $^{13}$C$_8$-G2(Bn$_5$) (20 ug) was treated with β-1,4-galactosidase from *A. oryzae* (15 mU) in phosphate/citrate buffer 50 mM at pH 4.5 for 18h at 30° C. and the reaction was quenched by the addition of MeOH (20 μL). This solution was directly analysed by UPLC-MS showing conversions of 10% and 46% to the mono-galactosylated compounds $^{13}$C$_8$-G1$^6$(Bn$_5$) and $^{13}$C$_8$-G1$^3$(Bn$_5$) respectively.

Preparation of Asymmetric α-2,3-Sialylated Glycan Standards

Silylation of $^{13}$C$_8$-G2(Bn$_5$)

The reaction was performed at analytical scale from the previously prepared bis-galactosylated biantennary $^{13}$C$_8$-G2 (Bn$_5$) (10 nmol). This compound was treated with 10 mU of α-2,3-sialyltransferase from *P multocida* and cytidine monophosphate N-acetylneuraminic acid (CMP-NeuNAc, 4 equivalents) in Tris.HCl buffer 100 mM at pH 8.0, containing 20 mM MgCl$_2$ at 37° C. for 30 minutes. The reaction was quenched by the addition of MeOH (20 µL). This solution was directly analysed by UPLC-MS showing a 46% conversion to the mono-sialylated compound $^{13}C_8$-G2A1(Bn$_5$), separated into two isomeric peaks (these being the corresponding 3- and 6-mono-silylated products), and a 32% conversion to the bis-sialylated compound $^{13}C_8$-G2A2 (Bn$_5$).

The reaction was performed at preparative scale from the previously prepared bis-galactosylated biantennary $^{13}C_8$-G2 (Bn$_5$). A solution (100 µL) of $^{13}C_8$-G2Bn$_5$ (1.0 mg, 0.48 µmol), Cytidine-5'-monophospho-N-acetylneuraminic acid sodium salt CMP-NeuAc (0.72 mg, 0.96 µmol, 2 eq), 100mU of α-2,3-Sialyltransferase from Pasteurella multocida 2.4.99.4 and MgCl$_2$ (100 mM) in 500 µL Tris-HCl buffer (1M, pH=8) was incubated at 37° C. for 30 min. MeOH (500 µL) was added to the resulting mixture to precipitate the enzyme. After centrifugation, the supernatant was purified by HPLC in a C18 semipreparative column in reverse phase water/ACN to give three new isotopically-labelled glycan standards, the two $^{13}C_8$-G2A1(Bn$_5$) compounds and $^{13}C_8$-G2A2(Bn$_5$).

Synthesis of $^{13}C_8$-G1A1$^3$Bn$_5$

A solution (100 µL) of $^{13}C_8$-G1$^3$(Bn$_5$) (1.0 mg, 0.52 µmol), Cytidine-5'-monophospho-N-acetylneuraminic acid sodium salt CMP-NeuAc (0.78 mg, 1.04 µmol, 2 eq), 100mU of α-2,3-Sialyltransferase from Pasteurella multocida 2.4.99.4 and MgCl$_2$ (100 mM) in 500 µL Tris-HCl buffer (1M, pH=8) was incubated at 37° C. for 30 min. MeOH (500 µL) was added to the resulting mixture to precipitate the enzyme. After centrifugation, the supernatant was purified by HPLC in a C$_{18}$ semipreparative column in reverse phase water/ACN obtaining compound $^{13}C_8$-G1A1$^3$(Bn$_5$) (0.68 mg, 59% Yield).

Preparation of α-2,6-Silylated Glycan Standards

The reaction was performed at analytical scale from the previously prepared bis-galactosylated biantennary $^{13}C_8$-G2 (Bn$_5$) (5 nmol). This compound was treated with 0.25mU of human α-2,6-sialyltransferase and cytidine monophosphate N-acetylneuraminic acid (CMP-NeuNAc, 1-4 equivalents) in cacodylate buffer 50 mM at pH 6.1, containing 2 mM MnCl$_2$ at 37° C. for 2-4 hours. The reaction was quenched by the addition of MeOH (20 µL). This solution was directly analysed by UPLC-MS and the results are presented in Table 3.

Preparation of Truncated N-Glycan Standards $^{13}C_8$-G0(Bn$_5$) (3 mg) was treated with 100 mU of N-acetyl glucosaminidase from Conavalia ensiformis in ammonium acetate buffer 50 mM at pH 4.5 at r.t. for 6h. The reaction was quenched by the addition of MeOH (20 µL). This solution was directly analysed by UPLC-MS obtaining conversions of 20%, 26% and 25% of $^{13}C_6$-MGn$^3$(Bn$_5$), $^{13}C_6$-MGn$^6$(Bn$_5$) and $^{13}C_4$-Man3(Bn$_5$) respectively. After semipreparative HPLC purification the pure compounds $^{13}C_6$-MGn$^3$(Bn$_5$) (2.2 mg), $^{13}C_6$-MGn$^6$(Bn$_5$) (2.0 mg) and $^{13}C_4$-Man3(Bn$_5$) (1.7 mg) were obtained.

The three isolated compounds were subjected to hydrogenolysis in MeOH using 1 atm of H2 gas in an H-Cube flow reactor with a 10% Pd/C cartridge, obtaining the $^{13}$C-labeled N-glycans $^{13}C_6$-MGn$^3$ (1.2 mg) and $^{13}C_6$-MGn$^6$ (1.1 mg) and $^{13}C_4$-Man3 (0.7 mg) in pure form.

Fucosylation of $^{13}C_6$-MGn$^3$

The compound $^{13}C_6$-MGn$^3$ (1.2 mg) was treated with a core α-1,6-fucosyltransferase and guanosine diphosphate fucose (GDP-Fuc, 1.10 equivalents) in MES buffer 50 mM at pH 6.5, containing MgCl$_2$ 2 mM. After 18h of reaction at 30° C. the proteic fraction was precipitated by heating at 95° C. for 5 minutes and filtered off. The glycan $^{13}C_6$-MGn$^3$F was purified with a graphitized carbon cartridge.

Galactosylation of Partially-Protected Triantennary Core 22

A solution (24 µL) of triantennary 22 (120 µg, 0.06 µmol), Uridine 5'-diphospho-α-D-galactose disodium salt UDP-Gal (55 µg, 0.09 µmol, 1.5 eq), 24mU of bovine milk β-1,4-galactosyltransferase 2.4.4.22 and MnCl$_2$ (10 mM) in 300 µL HEPES buffer (50 mM, pH=7.4) was incubated at 37° C. for 1 h. The resulting mixture was heated at 95° C. for 5 min to precipitate the enzyme. After centrifugation, the supernatant was directly analysed by UPLC-MS. All seven possible galactosylated products were detected (tris, all three bis and all three mono), in addition to the non-galactosylated starting material.

REFERENCES

All publications, patents and patent applications cited herein or filed with this application, including references filed as part of an Information Disclosure Statement, are incorporated by reference in their entirety.

J. A. Atwood III, L. Cheng, G. Alvarez-Manilla, N. L. Warren, W. S. York, R. Orlando, Journal of proteome research 2007, 7, 367-374.

O. Blixt, N. Razi, Method in Enzymology 2006, 415, 137-153.

J. C. Botelho, J. A. Atwood III, L. Cheng, G. Alvaez-Manilla, W. S. York, R. Orlando, International Journal of Mass Spectrometry 2008, 278, 137-142.

M. J. Bowman, J. Zaia, Analytical chemistry 2007, 79, 5777-5784.

M. J. Bowman, J. Zaia, Analytical chemistry 2010, 82, 3023-3031.

M. A. Breidenbach, K. K. Palaniappan, A. A. Pitcher, C. R. Bertozzi, Molecular & Cellular Proteomics 11.6, 2012.

A. M. Hitchcock, C. E. Costello, J Zaia, Biochemistry 2006, 45, 2350-2361

J. Hsu, S. J. Chang, A. H. Franz, American Society for Mass Spectrometry 2006, 17, 194-204.

P. Kang, Y. Mechref, Z. Kyselova, J. A. Goetz, M. V. Novotny, Analytical chemistry 2007, 79, 6064-6073.

R. Lawrence, S. K. Olson, R. E. Steele, L. Wang, R. Warrior, R. D. Cummings, J. D., Esko Journal of biological chemistry 2008, 283, 33674-33684.

G. Ridlova, J. C. Mortimer, S. L. Maslen, P. Dupree, e. Stephens, Rapid Communications in Mass Spectrometry 2008, 22, 2723-2730.

T. W. D. F. Rising, C. D. Heidecke, J. W. B. Moir, Z. Ling, A. J. Fairbanks, Chemistry—A European Journal 2008, 14, 6444-6464.

N. Ruiz, S. S. Ferreira, D. Padro, N.-C. Reichardt, M. Martín-Lomas, Carbohydrate Research 2011, 246, 1581-1591.

S. Serna, J. Etxebarria, N. Ruiz, M. Martín-Lomas, N.-C. Reichardt, Chemistry—A European Journal 2010, 16, 13163-13175.

B. Xia, C. L. Feasley, G. P. Sachdev, D. F. Smith, R. D. Cummings, Analytical biochemistry 2009, 387, 162-170.

J. Yuan, N. Hashii, N. Kawasaki, S. Itoh, T. Kawanishi, T. Hayakawa, journal of chromatography A 2005, 1067, 145-152.

H. Zhang, X.-J. Li, D. B. Martin, R. Aebersold, Nature biotechnology 2003, 21, 660-6.

G. Zou, H. Ochiai, W. Huang, Q. Yang, C. Li, L.-X. Wang, Journal of the American Chemical Society 2011, 133, 18975-18991.

The invention claimed is:

1. A glycan comprising the motif:

wherein each Ac* is isotopically-labelled.

2. The glycan of claim 1, wherein each Ac* is selected from —($^{13}$C═O)$^{13}$CH$_3$, —(C═O)$^{13}$CH$_3$, —($^{13}$C═O)CH$_3$, —(C═O)CD$_3$, —($^{13}$C═O)$^{13}$CD$_3$, —(C═O)$^{13}$CD$_3$, —($^{13}$C═O)CD$_3$, —($^{14}$C═O)$^{14}$CH$_3$, —(C═O)$^{14}$CH$_3$, —($^{14}$C═O)CH$_3$, —(C═$^{17}$O) CH$_3$, —($^{13}$C═$^{17}$O) CH$_3$, —(C═$^{17}$O)$^{13}$CH$_3$, —($^{13}$C═$^{17}$O)$^{13}$CH$_3$, —(C═$^{18}$O)CH$_3$, —($^{13}$C═$^{18}$O) CH$_3$, —(C═$^{18}$O)$^{13}$CH$_3$, —($^{13}$C═$^{18}$O)$^{13}$CH$_3$.

3. The glycan according to claim 2, wherein the glycan comprises one or more further monosaccharide units.

4. A kit for identifying a glycan in a sample, the kit comprising:
   (a) a tagged standard, the tagged standard comprising an isotopically-labelled glycans according to claim 1

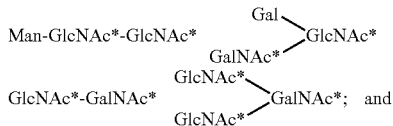

(b) instructions for doping a sample suspected of containing a glycan with the tagged standard to obtain a doped sample and analysing the doped sample using mass spectrometry.

5. The kit of claim 4, wherein the instructions include mass spectrometry data for the tagged standard.

6. The kit of claim 4, wherein the instructions include the step of comparing the ion peaks associated with the tagged standard with the additional ion peaks in the mass spectrum.

7. A method for the synthesis of an isotopically-labelled glycan as claimed in claim 1 for use as a mass spectrometry internal standard, the method comprising:
   acylating an oligosaccharide core structure with an isotopically-labelled acylating agent, wherein the oligosaccharide core structure is optionally protected with one or more protecting groups, to obtain an isotopically-labelled oligosaccharide core structure; and
   enzymatically derivatising the resultant isotopically-labelled oligosaccharide to obtain the isotopically-labelled glycan.

8. The method of claim 7, wherein the enzymatic derivatisation comprises an enzymatic hydrolysis step to remove a terminal sugar unit.

9. The method of claim 7, wherein the enzymatic derivatisation comprises an enzymatic elongation step with a glycosyltransferase and a suitable sugar donor, optionally wherein the enzymatic elongation step incorporates a sugar unit that is itself isotopically-labelled.

10. The method of claim 7, wherein the isotopically-labelled oligosaccharide core structure is protected with one or more protecting groups during enzymatic derivatisation.

11. The method of claim 10, wherein the isotopically-labelled oligosaccharide core structure is protected with one or more optionally substituted benzyl groups.

12. The method of claim 7, wherein the oligosaccharide core structure comprises a disaccharide motif, the disaccharide motif comprising a first monosaccharide unit and a second monosaccharide unit, wherein at least one of the first monosaccharide unit and/or second monosaccharide unit comprises an amino group and acylation occurs at the amino group(s).

13. The method according to claim 7, wherein the isotopically-labelled acylating agent is isotopically-labelled acetic anhydride.

14. The method according claim 13, wherein the isotopically-labelled acetylating agent is selected from:
($^{13}$CH$_3$$^{13}$C═O)$_2$, ($^{13}$CH$_3$C═O)$_2$, (CH$_3$$^{13}$C═O)$_2$, (CD$_3$C═O)$_2$, ($^{13}$CD$_3$$^{13}$C═O)$_2$, ($^{13}$CD$_3$C═O)$_2$ or (CD$_3$$^{13}$C═O)$_2$.

15. The method of claim 7, wherein the method further comprises forming an oxazoline at a free anomeric position of an acetyl-hexosamine unit in the isotopically-labelled oligosaccharide.

16. The method of claim 7, wherein the method further comprises glycosylating a peptide, lipid or protein to obtain an isotopically-labelled glycopeptide, peptidoglycan, glycolipid, glycoprotein comprising the isotopically-labelled oligosaccharide.

17. A method comprising:
   (i) obtaining a sample suspected of containing a glycan associated with a disease or disorder from a patient;
   (ii) selecting a tagged standard that comprises an isotopically-labelled glycan as claimed in claim 1

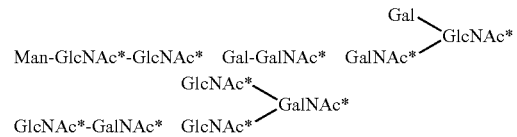

and corresponds to a glycan associated with the disease or disorder;
   (iii) adding the tagged standard to the sample to obtain a doped sample;
   (iv) analyzing the doped sample using mass spectrometry to obtain ion peaks;
   (v) comparing the identity and intensity of the ion peaks associated with the tagged standard with the additional ion peaks in the spectrum of the doped sample to identify, and optionally to quantify, the presence of one or more glycans in the sample;
   (vi) using the presence of said one or more glycans to diagnose the disease or disorder.

18. The method of claim 17, wherein the medical disease or disorder is selected from cancer, a cardiovascular disorder, an inflammatory skin disease, diabetes mellitus, a gastrointestinal disorder, a liver disorder, anaemia, an immunological disease or disorder, autoimmune disease, arthritis, including rheumatoid arthritis, an infectious disease, nephropathy, a neurological disorder, a pulmonary disorder or a congenital disorder of glycosylation.

* * * * *